US012582637B2

(12) United States Patent
Hakonarson et al.

(10) Patent No.: US 12,582,637 B2
(45) Date of Patent: Mar. 24, 2026

(54) TOPICAL FORMULATION FOR INTRADERMAL APPLICATION AND USES THEREOF

(71) Applicant: Arctic Therapeutics hf, Reykjavik (IS)

(72) Inventors: Hakon Hakonarson, Malvern, PA (US); Charlly Kao, Philadelphia, PA (US); Edward T. Kisak, San Diego, CA (US); John M. Newsam, La Jolla, CA (US); Avadhesh S. Kushwaha, San Diego, CA (US)

(73) Assignee: ARCTIC THERAPEUTICS HF, Reykjavik (IS)

( * ) Notice: Subject to any disclaimer, the term of this patent is extended or adjusted under 35 U.S.C. 154(b) by 798 days.

(21) Appl. No.: 17/271,829

(22) PCT Filed: Aug. 29, 2019

(86) PCT No.: PCT/US2019/048735
§ 371 (c)(1),
(2) Date: Feb. 26, 2021

(87) PCT Pub. No.: WO2020/047205
PCT Pub. Date: Mar. 5, 2020

(65) Prior Publication Data
US 2021/0251973 A1     Aug. 19, 2021

Related U.S. Application Data

(60) Provisional application No. 62/725,653, filed on Aug. 31, 2018.

(51) Int. Cl.
| | |
|---|---|
| *A61K 31/445* | (2006.01) |
| *A61K 9/00* | (2006.01) |
| *A61K 47/10* | (2017.01) |
| *A61K 47/14* | (2017.01) |
| *A61K 47/38* | (2006.01) |
| *A61P 17/00* | (2006.01) |
| *A61P 17/06* | (2006.01) |
| *A61P 17/10* | (2006.01) |

(52) U.S. Cl.
CPC .......... *A61K 31/445* (2013.01); *A61K 9/0014* (2013.01); *A61K 47/10* (2013.01); *A61K 47/14* (2013.01); *A61K 47/38* (2013.01); *A61P 17/00* (2018.01); *A61P 17/06* (2018.01); *A61P 17/10* (2018.01)

(58) Field of Classification Search
CPC .... A61K 31/445; A61K 9/0014; A61K 47/10; A61K 47/14; A61K 47/38; A61P 17/00; A61P 17/06; A61P 17/10; A61P 29/00
See application file for complete search history.

(56) References Cited

U.S. PATENT DOCUMENTS

| | | | |
|---|---|---|---|
| 6,024,980 A | 2/2000 | Hoy | |
| 8,277,762 B2 | 10/2012 | Newsam | |
| 8,840,922 B2 | 9/2014 | Kawakami | |
| 9,155,711 B2 | 10/2015 | Choi | |
| 9,186,345 B2 | 11/2015 | Snorrason | |
| 9,730,919 B2 | 8/2017 | Snorrason, I | |
| 2007/0287733 A1 | 12/2007 | Snorrason | |
| 2013/0280783 A1 | 10/2013 | Culbertson | |
| 2015/0352058 A1* | 12/2015 | Mo ...................... A61K 9/7061 |
| | | | 514/319 |

FOREIGN PATENT DOCUMENTS

| | | | |
|---|---|---|---|
| EP | 3338768 | | 6/2018 |
| IN | 2012MU01218 | * | 1/2014 |
| JP | H11315016 | | 11/1999 |
| JP | 2014517061 | | 7/2014 |
| WO | 2006040688 | | 4/2006 |
| WO | 2016209982 | | 12/2016 |
| WO | 2017099246 | | 6/2017 |
| WO | 2017118622 | | 7/2017 |

OTHER PUBLICATIONS

Lachenmeier, Safety evaluation of topical applications of ethanol on the skin and inside the oral cavity (Journal of Occupational Medicine and Toxicology, 3:26). (Year: 2008).*
Opinion on Diethyleneglycol monoethylether (European Commission ) (Year: 2008).*
Lane, Skin Penetration Enhancers, (International Journal of Pharmaceutics, 447, 12-21). (Year: 2013).*
Jang et al. (Toxicol. Res. 31:2, 105-136). (Year: 2015).*
Coupland et al. Their Use in Personal Care Products (Lipids, Lipid Technologies and Applications, 15). (Year: 1997).*
Kim et al., 2011, "Effects of vehicles on the percutaneous absorption of donepezil hydrochloride across the excised hairless mouse skin" Journal Drug Development and Industrial Pharmacy, 37:1125-1130.

\* cited by examiner

*Primary Examiner* — Joseph K Mckane
*Assistant Examiner* — Meghan C Heasley
(74) *Attorney, Agent, or Firm* — Troutman Pepper Locke LLP

(57) ABSTRACT

The invention provides compositions comprising a topical formulation of donepezil and methods of use thereof for intradermal applications.

20 Claims, 17 Drawing Sheets

Figure 25B
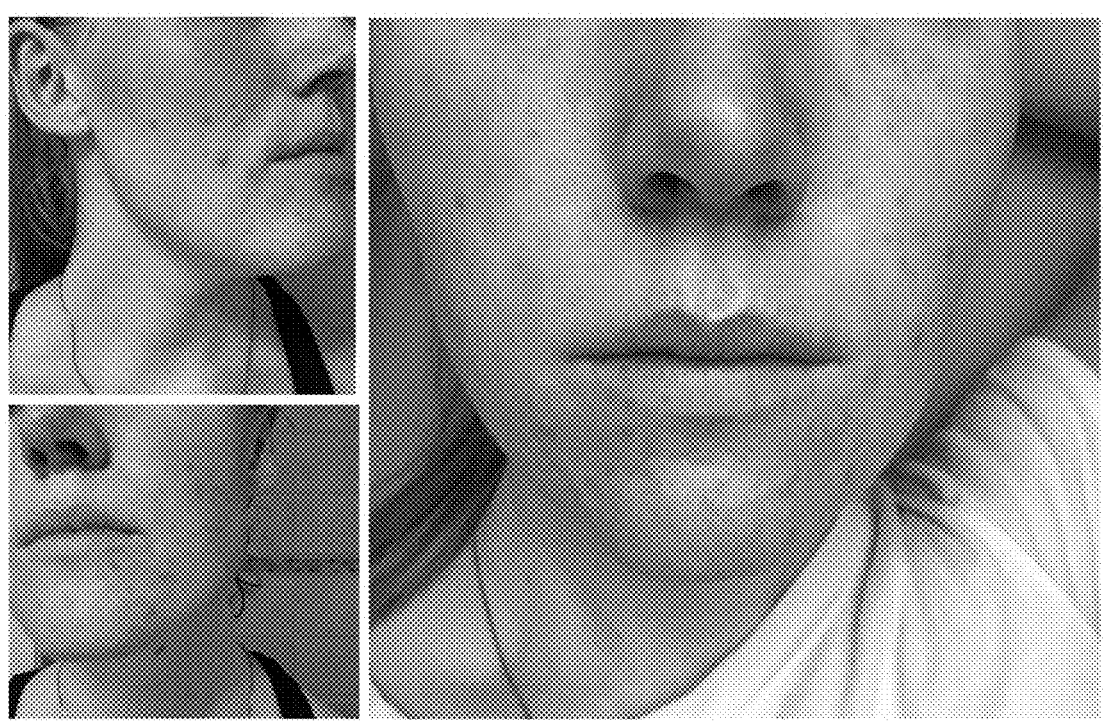
Figure 25C
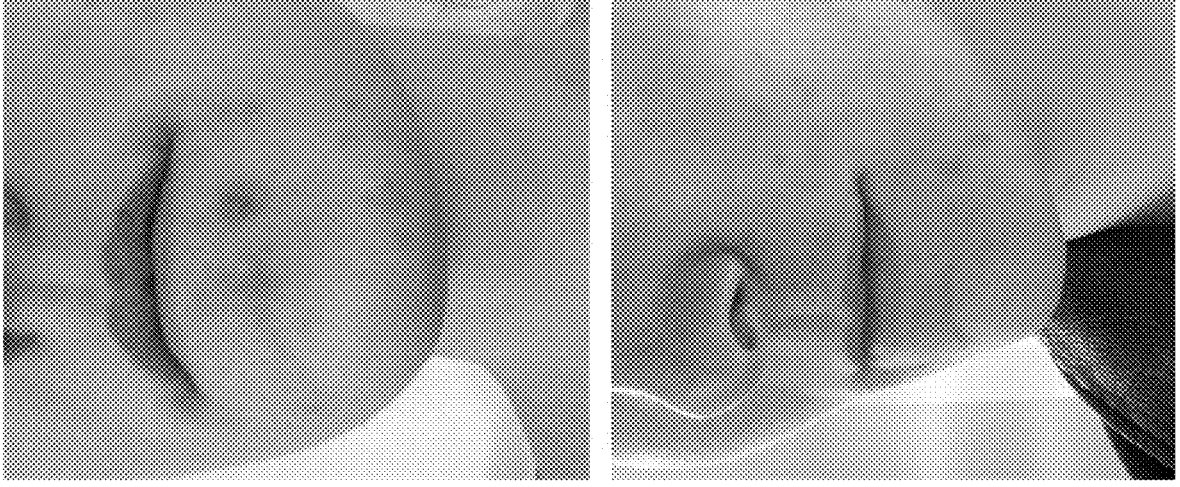
Figure 25 (cont.)

TOPICAL FORMULATION FOR INTRADERMAL APPLICATION AND USES THEREOF

CROSS-REFERENCE TO RELATED APPLICATIONS

This application is a 35 U.S.C. § 371 national phase application from International Application PCT/US2019/048735, filed Aug. 29, 2019, which claims priority to U.S. Provisional Application No. 62/725,653, filed Aug. 31, 2018, the disclosures of which are hereby incorporated by reference in their entireties.

BACKGROUND OF THE INVENTION

Acetylcholine is a classical neurotransmitter that has increasingly been recognized to occur in a large variety of cells outside the central nervous system (CNS). Acetylcholine has been shown to be produced in fibroblasts, melanocytes, endothelial cells and cells of the immune system. Acetylcholine can alter a variety of cellular functions where it acts on cells through its two classes of receptors, nicotinic acetylcholine receptors and muscarinic receptors. The nicotinic acetylcholine receptor is a ligand-gated ion channel formed by five subunits: alpha 3, alpha 5, beta 2 and beta 4 subunits, and by alpha 7 subunits that can form functional nicotinic receptors of their own. The presence of these structures, i.e. in keratocytes, can be shown by histochemical methods, i.e. antibodies to alpha 3 or alpha 7 subunits.

Donepezil hydrochloride is a reversible inhibitor of the enzyme acetylcholinesterase, known chemically as (+)-2,3-dihydro-5,6-dimethoxy-2-[[1 (phenylmethyl)-4-piperidinyl] methyl]-1H-inden-1-one hydrochloride. Donepezil hydrochloride is commonly referred to in the pharmacological literature as E2020. It has an empirical formula of $C24H29NO3HCl$ and a molecular weight of 415.96. Donepezil hydrochloride is a white crystalline powder and is freely soluble in chloroform, soluble in water and in glacial acetic acid, slightly soluble in ethanol and in acetonitrile and practically insoluble in ethyl acetate and in n-hexane.

Donepezil hydrochloride has been approved for human treatment as Aricept®, for the treatment of Alzheimer's disease. It is an orally administered drug. Attempts have been made to formulate donepezil to be delivered transdermally. The goal of such formulations is to accomplish rapid transdermal delivery for systemic application to treat Alzheimer's disease and dementia and related psychotic diseases. This route has benefit due to concerns about patient compliance with the orally administered version. Some of the transdermal embodiments include patch formats with the transdermal formulation attached or embedded therein. Choi et al. U.S. Pat. No. 9,155,711 and Kawakami et al. U.S. Pat. No. 8,840,922 represent transdermal formulations. For example, Choi discusses treatment of Alzheimer's and a transdermal drug delivery system that not only shows high skin penetration rate but also continuously maintains a therapeutically effective blood concentration for at least 24 hours. Further, the art per Kawakami, teaches donepezil for treatment of Alzheimer's via transdermal delivery using absorption promoters selected from lauryl alcohol, triethyl citrate, isopropyl myristate, cetyl lactate, oleyl alcohol, Sorbitan monooleate, polyethyleneglycol monostearate, lauromacrogol, N-methyl-2-pyrrolidone, and triacetin. However, there lacks a teaching that donepezil can and should be delivered intradermally.

Further complicating the use of donepezil for topical applications is that it has been known that one common adverse effect observed during human clinical trials of Aricept (donepezil HCl) is the negative side effect of eczema and pruritis.

More recent teachings have shown that donepezil hydrochloride and donepezil can be applied directly onto the skin to treat a number of skin ailments. See, for example, Snorrason et al. U.S. Pat. Nos. 9,186,345, and 9,730,919.

While there exists some teaching in the art that donepezil and its salt could be used to treat or ameliorate dermatologic diseases, a topical formulation to achieve intradermal delivery is not known and is fraught with complications. Skin has evolved to impede the flux of exogenous molecules by providing an excellent barrier to molecular delivery, particularly molecules such as pharmaceutical agents. Only a small number of drug molecules are available in a transdermal mode of administration; for example, less than thirty (30) drug molecules are available in transdermal patch. The challenge of delivering a drug molecule through the main barrier to ingress, the outermost layer of the epidermis called the stratum corneum, and maintaining an intradermal concentration of the drug is yet more daunting.

Several so-called physical methods are described for delivering an active agent through the stratum corneum. Such methods remove the stratum corneum by ablation, or cause damage to or puncture the stratum corneum. Physical methods include electrically assisted techniques such as iontophoresis or electroporation, ultrasonication, and hypodermic needles or microneedle arrays. A preferred alternative to physical methods are so called passive methods. Rather than inflicting damage by a physical device, passive methods employ chemical or molecular means to enhance stratum corneum permeability. The most appealing passive methods entail use of molecular penetration enhancers, or MPEs, molecules which interact with the structure of the stratum corneum at the molecular level to facilitate molecule ingress by one or more of several mechanisms, for example, by disrupting the lipid bilayers of the stratum corneum.

Over 300 substances have been identified as MPEs but only a very small subset have been successfully incorporated into commercial formulations. There are several reasons. First, many potent MPEs are skin irritants and are hence impractical and contrary to the goal of treating skin diseases. Second, there is a substantial regulatory barrier to incorporating a new excipient into a topical or transdermal formulation, as the burden of establishing the safety of such an excipient may rival that directed to a new drug molecule. Third, the best-performing MPE systems are rarely individual MPEs, but rather cocktails of more than one MPE. Fourth, high-performing MPE systems are usually more or less molecule-specific. An MPE system that performs well for one drug molecule will usually perform much less well for a different drug molecule. Fifth, it is not in general possible to predict which MPE system will work best for a given drug molecule, in a given base formulation chassis, and in a given formulation format. For each molecule for which topical or transdermal delivery has appeal, therefore, there is a huge need for an effective MPE system. Where, additionally, there is an additional requirement to maintain a therapeutically-effective dermal concentration of the molecule, the need is yet greater still.

Therefore, even with the knowledge of dermatologic applications for donepezil and donepezil hydrochloride, there remains a need to develop a formulation that enables the greatest permeation and retention of the compounds in the dermal layers of the skin.

SUMMARY OF THE INVENTION

Aspects of the present invention include compositions formulated for topical administration to deliver donepezil intradermally to a subject (i.e., for intradermal retention of the drug), In another aspect, the present invention relates to compositions prepared for topical administration to deliver donepezil intradermally, comprising (i) donepezil or a pharmaceutically acceptable salt thereof, (ii) 2-(2ethoxyethoxy) ethan-1-ol, (iii) a fatty acid ester, and (iv) a monohydric alcohol. In various embodiments, the compositions further comprise at least one low molecular weight polyethylene glycol. In some embodiments, the compositions comprise at least two monohyrdric alcohols. In some embodiments, the compositions comprise at least two glycols from the group consisting of: di-, oligo- or poly-ethylene glycols that have at least one terminal alkoxy group in place of a terminal hydroxyl group. In some embodiments, the compositions deliver an intradermal concentration of donepezil relative to the amount of donepezil provided transdermally that is at least twice that provided by a composition of donepezil in a solvent. In some embodiments, the compositions comprise donepezil, ethanol, 2-(2ethoxyethoxy) ethan-1-ol, and iso-propyl palmitate.

In another aspect of the invention, the compositions comprise donepezil HCl, water, cetyl alcohol, 2-(2-ethoxy-ethoxy) ethan-1-ol, a mixture of caprylic and capric (C10) triglyceride, and isopropyl palmitate.

In another aspect, the present invention includes methods of treating plaque psoriasis (psoriasis vulgaris) in a mammal in need thereof, the method comprising topically administering to a psoriasis plaque on the mammal the compositions described herein, wherein (1) the composition is in a form selected from the group consisting of a gel, a cream or an ointment; and (2) the concentration of donepezil or donepezil HCl is 0.05% to 2% by weight of the composition. In some embodiments, the composition is topically administered to the psoriasis plaque twice daily for a duration of two to six weeks.

In another aspect, the present invention includes methods of treating atopic dermatitis in a mammal in need thereof, the method comprising topically administering to skin of the mammal the compositions described herein, wherein (1) the composition is in a form selected from the group consisting of a gel, a cream or an ointment; and (2) the concentration of donepezil or donepezil HCl is 0.05% to 2% by weight of the composition.

In another aspect, the present invention includes methods of treating acne in a mammal in need thereof, the method comprising topically administering to skin of the mammal the compositions described herein, wherein (1) the composition is in a form selected from the group consisting of a gel, a cream or an ointment; and (2) the concentration of donepezil or donepezil HCl is 0.05% to 2% by weight of the composition.

BRIED DESCRIPTION OF THE DRAWINGS

Figure 17:
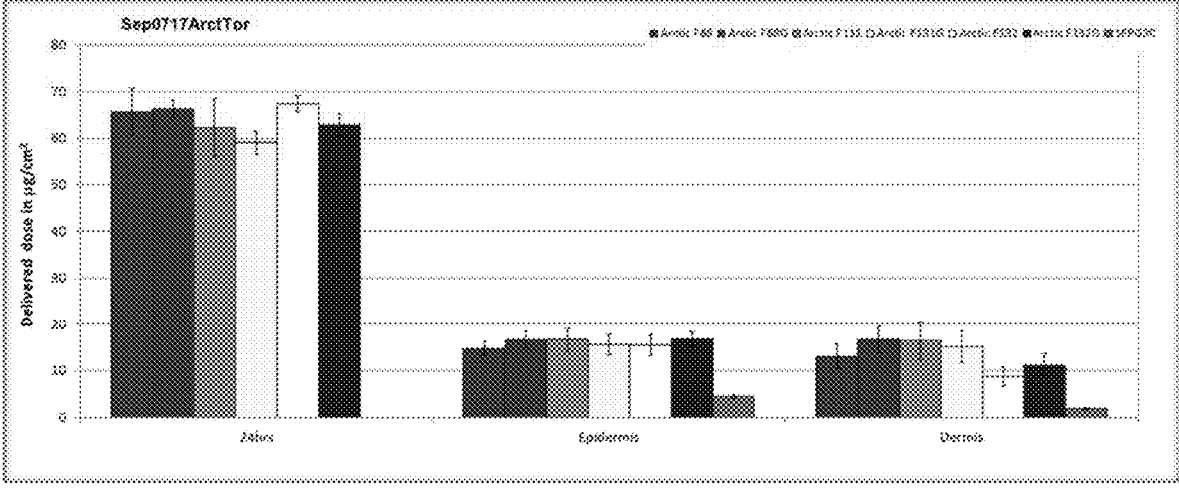

FIG. 17 shows bar graphs that represent data obtained from screening Donepezil base in an ethanol/propylene glycol/Transcutol chassis with isopropyl palmitate. The flux study was done using cadaver skin as the substrate. Formulations with a "G" at the end were gelled versions of their equivalent formulation.

Figure 18:
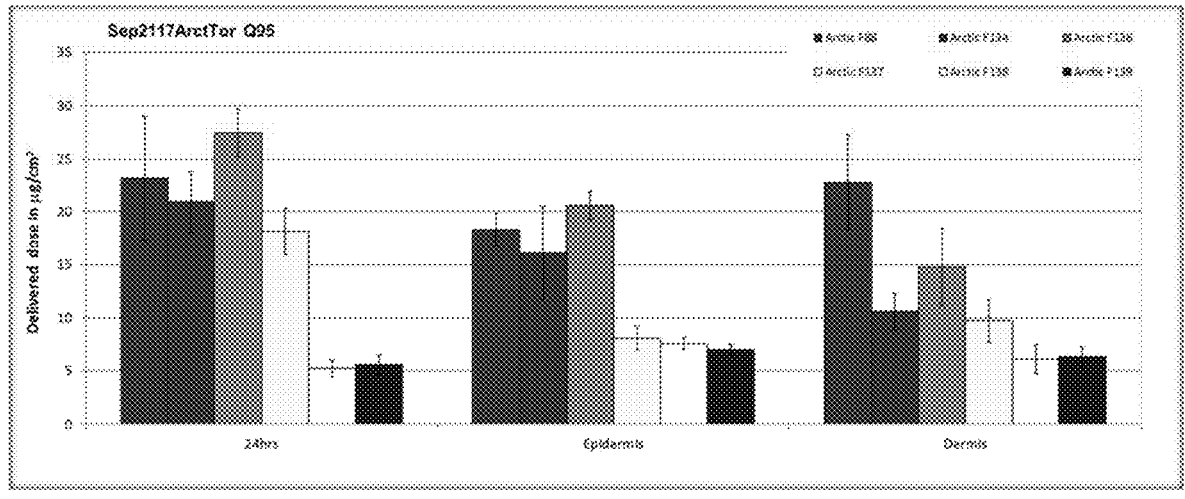

FIG. 18 shows bar graphs that represent data obtained from screening Donepezil base and donepezil HCl in an ethanol/propylene glycol/Transcutol chassis with isopropyl palmitate.

Figure 19:
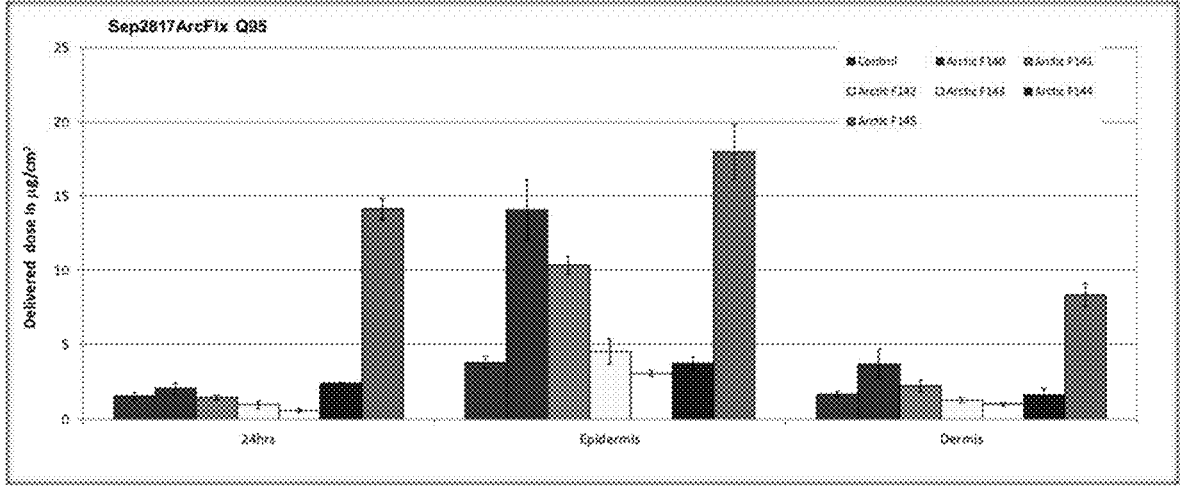

FIG. 19 shows bar graphs that represent data obtained from screening Donepezil base and donepezil HCl in an ethanol/Transcutol chassis with isopropyl palmitate. In order to slow down flux and shift the accumulated amount more into the dermal tissue, PEGs were added to the formulation.

Figure 20:
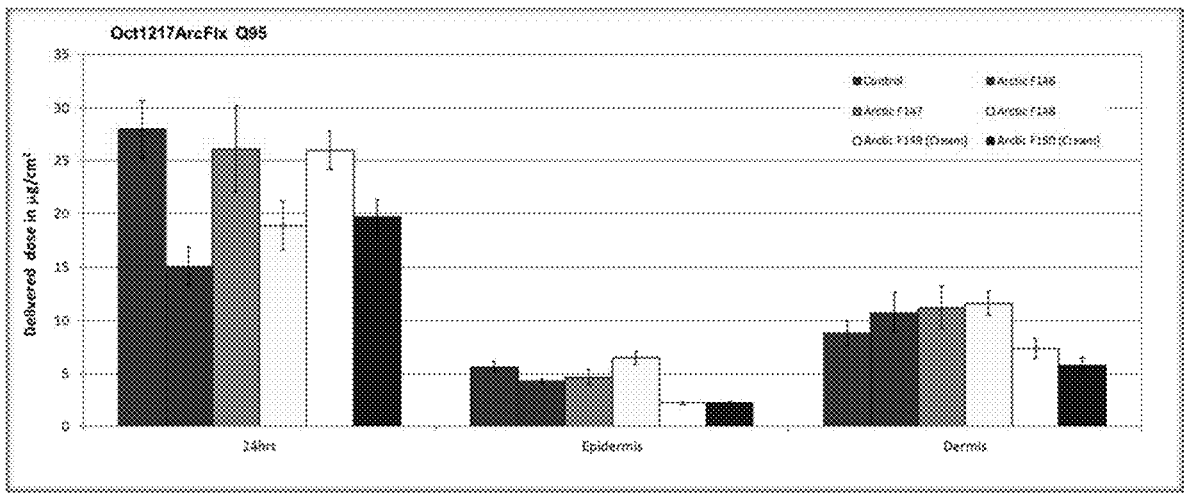

FIG. 20 shows bar graphs that represent data obtained from screening Donepezil base and donepezil HCl in an ethanol/Transcutol chassis with isopropyl palmitate and PEGs. Cream formulations (F149 and F150) were likewise tested.

Figure 21:
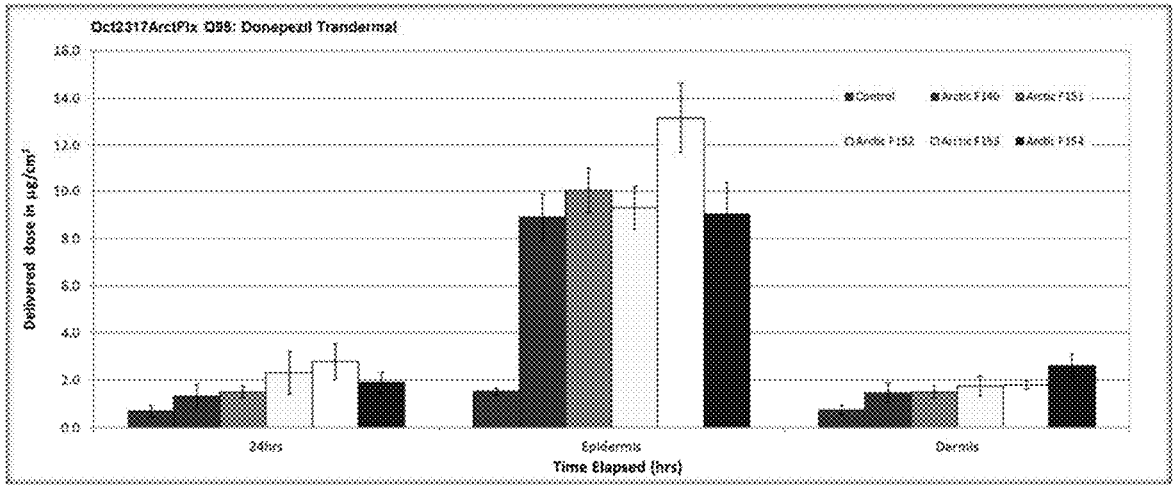

FIG. 21 shows bar graphs that represent data obtained from screening Donepezil base gel in an ethanol/Transcutol chassis with isopropyl palmitate and PEGs with a focus on optimizing the PEG/ethanol mixtures.

Figure 22:
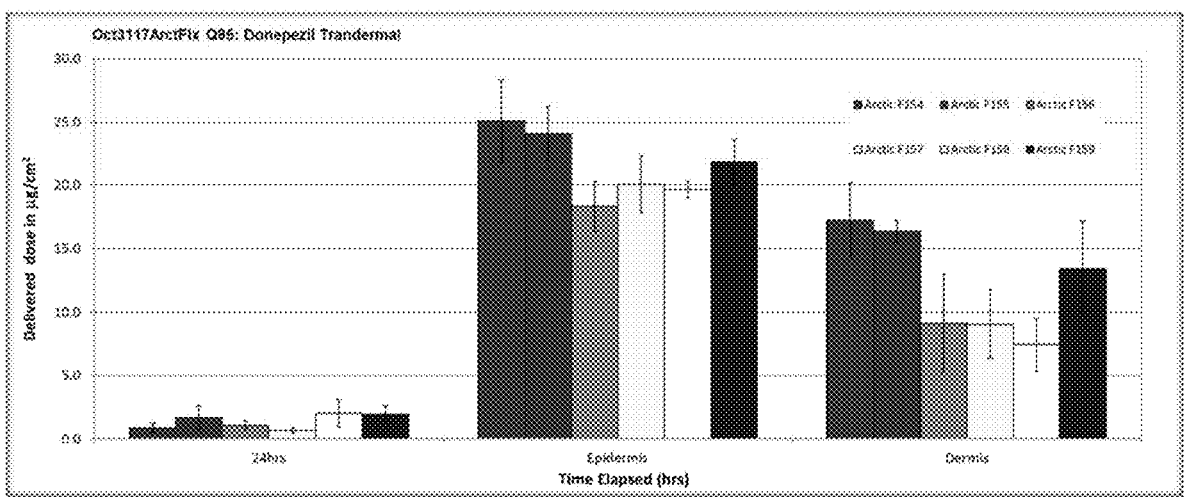

FIG. 22 shows bar graphs that represent data obtained from screening Donepezil base gel in an ethanol/Transcutol chassis with isopropyl palmitate and PEGs. Further optimizing the PEG/ethanol mixtures.

Figure 23:
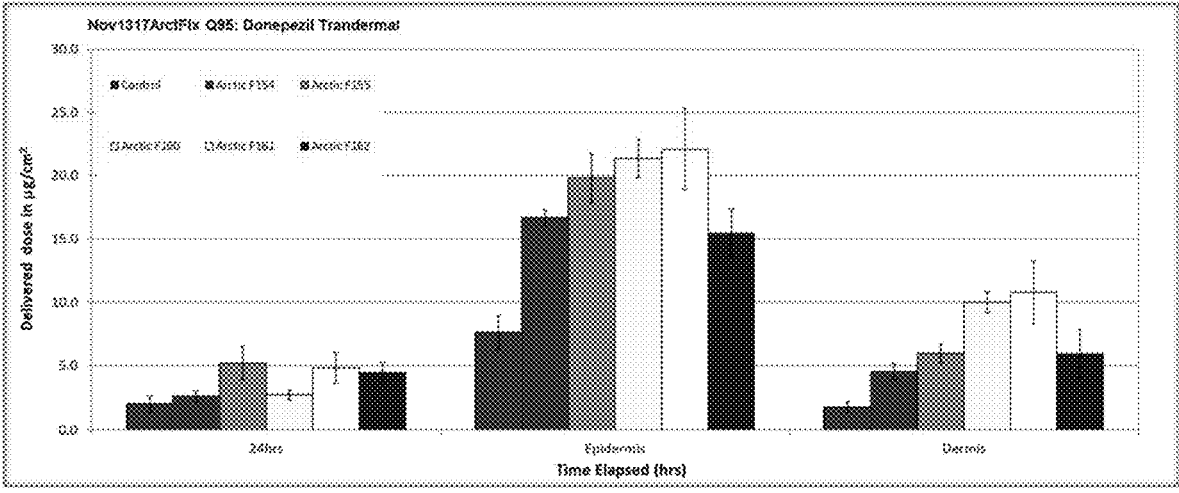

FIG. 23 shows bar graphs that represent data obtained from the final testing of the donepezil base gel in an ethanol/PEG/Transcutol with isopropyl palmitate mixture. F162 is a cream formulation using donepezil HCl.

Figure 24:
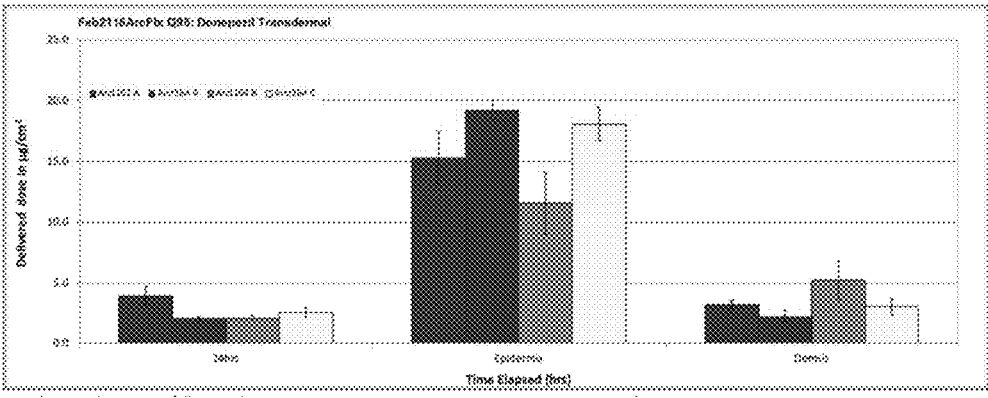

FIG. 24 shows bar graphs that represent data obtained from formulations Arct162A (or Arct162), Arct164A, Arct164B, and Arct164C.

Figures 25, 25A:

FIG. 25, comprising FIG. 25A through FIG. 25C, shows results from a ten day therapy with the F162 cream formulation, including b.i.d. application in one male and two female patients with pustulopapular acne. FIG. 25A shows a photo image panel of a 26 years old male with grade 3 acne on his left shoulder and back resistant to other therapies, including accutane (top panels before therapy with F162 and bottom panels following 10 day therapy with F162). FIG. 25B shows a photo image panel of 26 years of female with grade 3 acne resistant to other therapies, including accutane. FIG. 25C shows a photo image panel of a 28 years old females with grade 3 acne resistant to other therapies, including accutane.

Figure 26:
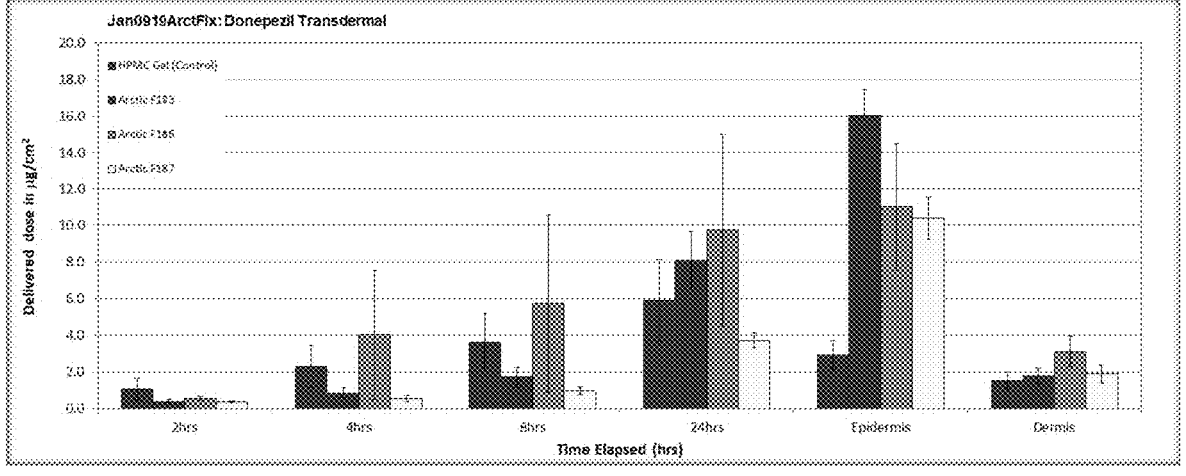

FIG. 26 depicts results for Donepezil Transdermal analysis of Jan0919ArcFlx.

Figure 27:
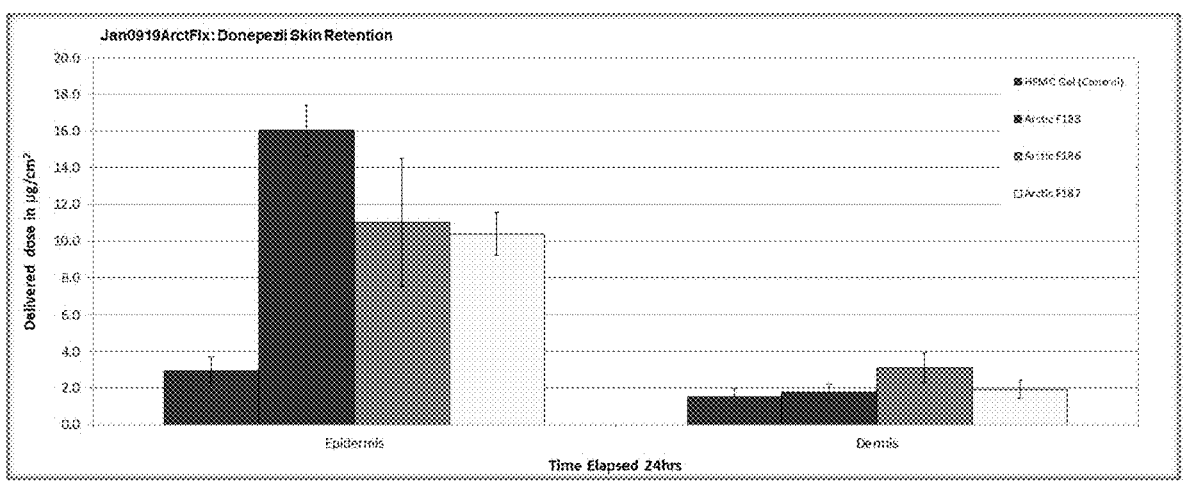

FIG. 27 depicts results for Donepezil Skin Retention analysis of Jan0919ArcFlx.

Figure 28:
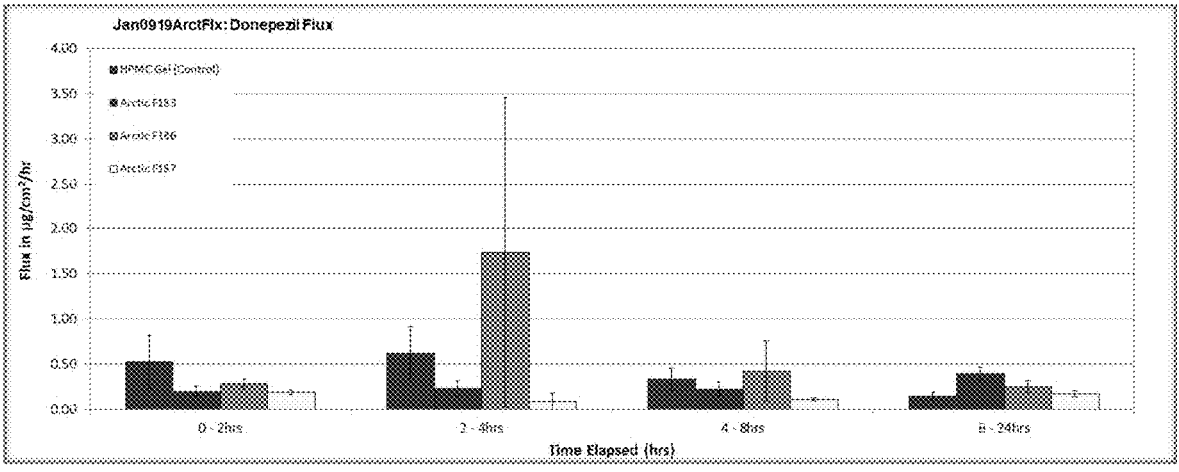

FIG. 28 depicts results for Donepezil Flux analysis of Jan0919ArcFlx.

Figure 29:
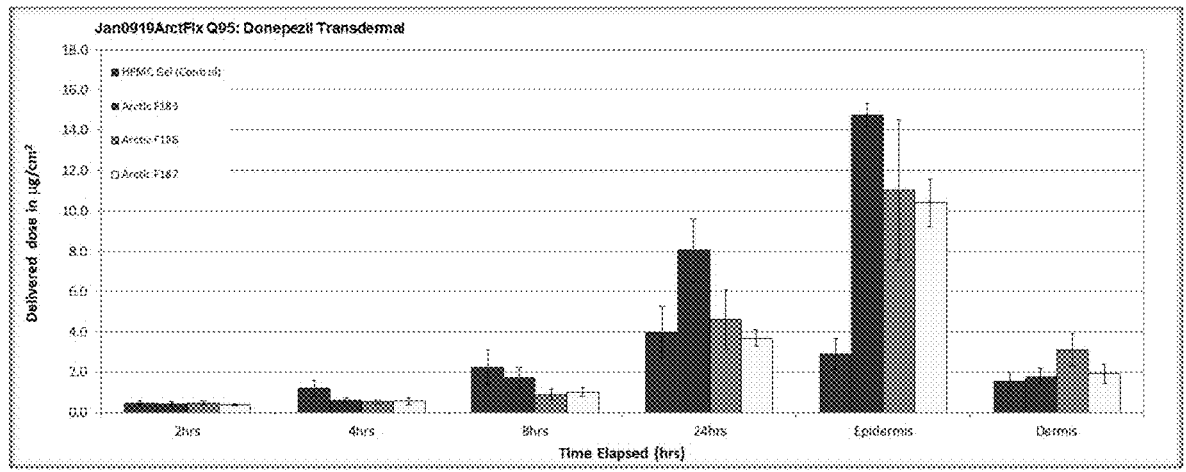

FIG. 29 depicts results for Donepezil Transdermal analysis of Jan0919ArcFlx Q95.

Figure 30:
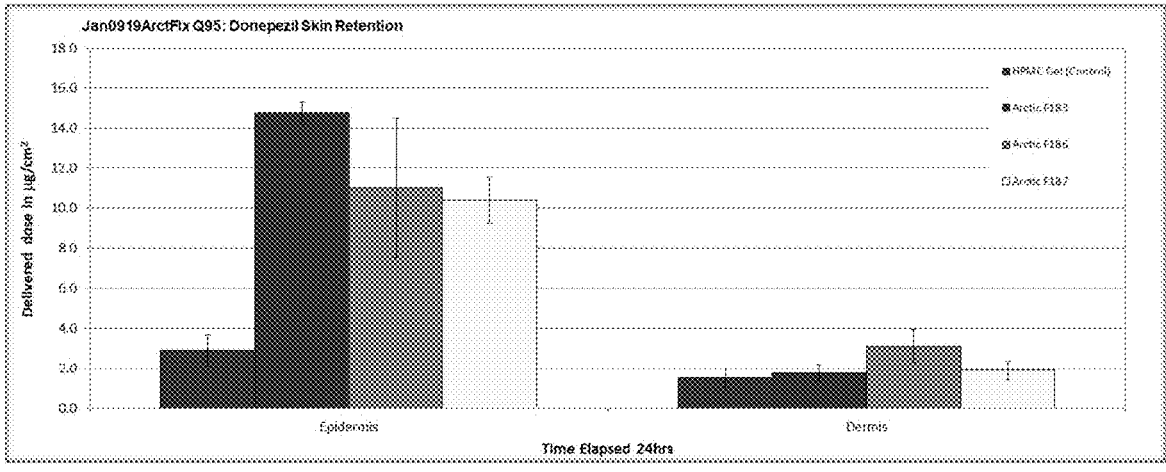

FIG. 30 depicts results for Donepezil Skin Retention analysis of Jan0919ArcFlx Q95.

Figure 31:
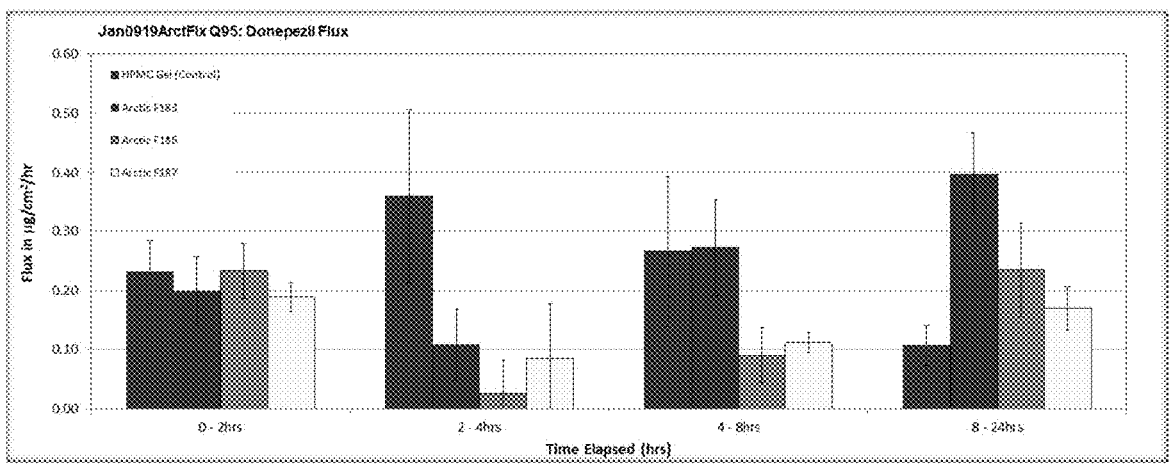

FIG. 31 depicts results for Donepezil Flux analysis of Jan0919ArcFlx Q95.

DETAILED DESCRIPTION

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

In describing and claiming the present invention, the following terminology will be used.

The singular forms "a," "an," and "the" include plural referents unless the context clearly dictates otherwise. Thus, for example, reference to "a penetration enhancer" includes reference to one or more of such penetration enhancers.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein. For example, in one embodiment, the degree of flexibility can be within about ±10% of the numerical value. In another embodiment, the degree of flexibility can be within about ±5% of the numerical value. In a further embodiment, the degree of flexibility can be within about ±2%, ±1%, or ±0.05%, of the numerical value.

As used herein, the term "active agent" indicates a compound or mixture of compounds, that when added to a composition, tend to produce a particular therapeutic effect, which herein is donepezil or its salt form.

As used herein, the term "comparative formulation" is a formulation that is compositionally identical with the exception that amounts (wt %) of the first compound and second compound are each replaced with the same amount (wt %) of water.

As used herein, the term "intradermal" means residing in the dermal compartment of the skin.

The term "intradermal administration" is used to mean administration from the skin exterior into the dermal compartment of the skin such that the concentration of the administered agent in the dermal compartment, relative to the concentration of such agent in the other skin compartments or provided transdermally, is substantially greater than for a comparator formulation. Intradermal administration of an active agent is highly desirable when its mode of action entails interaction with targets in the dermal tissue. As the active agent reaches the dermal compartment by diffusion through the stratum corneum and the epidermis, intradermal administration necessarily entails establishing a concentration of the active agent in the epidermal tissue. Similarly, intradermal administration does not exclude a small percentage of active agent permeating all the way through the skin.

The term "molecular penetration enhancer or MPE" is used herein to refer to an agent that improves the transport of molecules such as an active agent (e.g., a medicine) into or through the skin. Various conditions may occur at different sites in the body either in the skin or below creating a need to target delivery of compounds. For example, a psoriasis treatment may benefit from delivery of therapeutic drug levels in the deeper tissue. A "penetration enhancer" may be used to assist in the delivery of an active agent directly to the skin or underlying tissue or indirectly to the site of the disease through systemic distribution. A penetration enhancer may be a pure substance or may comprise a mixture of different chemical entities. In this specification the terms "penetration enhancer," "chemical penetration enhancer," "molecular penetration enhancer," and "MPE" are used interchangeably.

As used herein, the term "skin contact region" refers to an area wherein the topical formulation contacts the skin.

The term "subject" as used herein includes all members of the animal kingdom, including mammals, and most typically, refers to humans.

The term "topical administration" is used in its conventional sense to mean delivery of a substance, such as a therapeutically active agent, into the skin or a localized exterior region of the body, to include skin (intact, diseased, ulcerous, or broken) as well as mucosal surfaces that are usually at least partially exposed to air such as lips, genital and anal mucosa, and nasal and oral mucosa. Topical administration of a drug may often be advantageously applied in, for example, the treatment of various skin disorders or conditions.

As used herein the term "topical formulation" refers to a formulation that may be applied to an exterior region of the body, including to the skin as well as to mucosal surfaces, including genital, anal, nasal and oral mucosa, to the ear, the eye, or the lips. Topical formulations may, for example, be used to confer therapeutic benefit to a patient or cosmetic benefits to a consumer. Topical formulations can be used for both topical and transdermal administration of substances.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilizing (i.e. not worsening) the state of disease, delaying or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. In addition to being useful as methods of treatment, the methods described herein may be useful for the prevention or prophylaxis of disease.

The term "water" as an ingredient in the compositions of the compositions of the present disclosure refers to pharmaceutically-acceptable water.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 mm to 2.0 mm" should be interpreted to include not only the explicitly recited values of about 0.01 mm to about 2.0 mm, but also include individual values and sub-ranges within the indicated range. Thus, included in this numerical range are individual values such as 0.5 mm, 0.7 mm, and 1.5 mm, and sub-ranges such as from 0.5 mm to 1.7 mm, 0.7 mm to 1.5 mm, and from 1.0 mm to 1.5 mm, etc. Furthermore, such an interpretation should apply regardless of the breadth of the range or the characteristics being described. Additionally, it is noted that all percentages are in weight, unless specified otherwise.

The present disclosure is drawn to various formulations and methods in the area of topical and intradermal delivery of donepezil and donepezil hydrochloride. MPEs can be used to improve the administration and increase penetration of the active agent donepezil and donepezil hydrochloride into and residing therein.

Aspects of the present invention include compositions formulated for topical administration to deliver donepezil intradermally to a subject (with retention in the dermis), comprising (i) donepezil or a pharmaceutically acceptable salt thereof, (ii) 2-(2-ethoxyethoxy) ethan-1-ol, (iii) a fatty acid ester, and (iv) a monohydric alcohol. In various embodiments, the compositions further comprise at least one low molecular weight polyethylene glycol. In some embodiments the compositions include at least two monohydric alcohols. While in some embodiments, the compositions include at least two glycols from the group consisting of: di-, oligo- or poly-ethylene glycols that have at least one terminal alkoxy group in place of a terminal hydroxyl group. Preferably, the compositions deliver an intradermal concentration of donepezil relative to the amount of donepezil provided transdermally that is at least 2-3 times that provided by a comparator formulation.

In some embodiments, the compositions comprise donepezil, ethanol, at least two PEG selected from the group consisting of: PEG 400, PEG1450, and PEG600, 2-(2-ethoxyethoxy) ethan-1-ol, and isopropyl palmitate. Such compositions can further comprise hydroxypropyl cellulose, and preferably in an amount of 3%. In some embodiments, compositions comprise donepezil in an amount between 0.5%-1.5% (wt/wt), ethanol in an amount between 30%-40%, PEG 400 in an amount between 16%-26%, one of either PEG1450 or PEG 600 in an amount of 5%, 2-(2-ethoxyethoxy) ethan-1-ol in an amount between 20%-30%, and isopropyl palmitate in an amount of 5%. In some preferred embodiments, donepezil is present in an amount of 1% (wt/wt), ethanol in an amount of 40%, PEG 400 in an amount of 16%, PEG 600 in an amount of 5%, 2-(2-ethoxyethoxy) ethan-1-ol in an amount of 30%, and isopropyl palmitate in an amount of 5%. Whereas, in some preferred embodiments, the donepezil is present in an amount of 1% (wt/wt), ethanol in an amount of 40%, PEG 400 in an amount of 26%, PEG 600 in an amount of 5%, 2-(2-ethoxyethoxy) ethan-1-ol in an amount of 20%, and isopropyl palmitate in an amount of 5%.

In other embodiments, the compositions comprise donepezil HCl, water, cetyl alcohol, at least two PEG selected from the group consisting of: PEG 400, PEG1450, and PEG600, 2-(2-ethoxyethoxy) ethan-1-ol, a mixture of caprylic and capric (C10) triglyceride, isopropyl myristate, and isopropyl palmitate. Such compositions can further comprising propylene glycol in an amount of 7%. In some preferred embodiments the compositions comprise donepezil HCl in an amount of 1% (wt/wt), water in amount of 40.3%, cetyl alcohol in an amount of 10%, isopropyl myristate in an amount of 10%, a mixture of caprylic and capric (C10) triglyceride in an amount of 10%, and isopropyl palmitate in an amount of 7%. Whereas, in some preferred embodiments, donepezil HCl is present in an amount of 1% (wt/wt), water in an amount of 56.9%, cetyl alcohol in an amount of 3%, a mixed caprylic and capric (C10) triglyceride in amount of 5%, and isopropyl palmitate in amount of 7%.

In some embodiments, the donepezil is present in an amount between 0.5%-1.5% (wt/wt). In some embodiments, donepezil is present in an amount of 1% (wt/wt). In some embodiments, the ethanol is present in an amount between 30%-40%. In some embodiments, the ethanol is present in an amount of 40%. In some embodiments, the 2-(2-ethoxyethoxy) ethan-1-ol is present in an amount between 20%-30%. In some embodiments, the 2 (2-ethoxyethoxy) ethan-1-ol is present in an amount of 30%. In some embodiments, the 2 (2-ethoxyethoxy) ethan-1-ol is present in an amount of 20%. In some embodiments, the isopropyl palmitate is present in an amount of 5%. In some embodiments, the water is present in amount of 48.9%. In some embodiments, the water is present in amount of 51%. In some embodiments, the water is present in amount of 49%. In some embodiments, the cetyl alcohol is present in an amount of 11%. In some embodiments, the cetyl alcohol is present in an amount of 9%. In some embodiments, the mixture of caprylic and capric (C10) triglyceride is present in an amount of 5%. In some embodiments, the isopropyl palmitate is present in an amount of 7%.

In another aspect, the present invention includes methods of treating plaque psoriasis (psoriasis vulgaris) in a mammal in need thereof, the method comprising topically administering to a psoriasis plaque on the mammal the compositions described herein, wherein (1) the composition is in a form selected from the group consisting of a gel, a cream, and an ointment; and (2) the concentration of donepezil or donepezil HCl is 0.05% to 2% by weight of the composition. In some embodiments, the composition is topically administered to the psoriasis plaque twice daily for a duration of two to six weeks.

In another aspect, the present invention includes methods of treating atopic dermatitis in a mammal in need thereof, the method comprising topically administering to skin of the mammal the compositions described herein, wherein (1) the composition is in a form selected from the group consisting of a gel, a cream, and an ointment; and (2) the concentration of donepezil or donepezil HCl is 0.05% to 2% by weight of the composition.

In another aspect, the present invention includes methods of treating acne in a mammal in need thereof, the method comprising topically administering to skin of the mammal the compositions described herein, wherein (1) the composition is in a form selected from the group consisting of a gel, a cream, and an ointment; and (2) the concentration of donepezil or donepezil HCl is 0.05% to 2% by weight of the composition.

Active Ingredient

The active agent taught by the present invention is donepezil or a pharmaceutically acceptable salt thereof, such as donepezil hydrochloride (donepezil HCl), or a mixture thereof. The active can be present in the described formulations at an amount that delivers an effective dose of active intradermally. In some embodiments the Active Ingredient is present in a formulation (wt/wt %) of from 0.1% to 10%, 0.1% to 9%, 0.1% to 8%, 0.1% to 7%, 0.1% to 6%, 0.1% to 5%, 0.1% to 4%, 0.1% to 3%, 0.1% to 2%, 0.1% to 1%, 0.5% to 10%, 0.5% to 9%, 0.5% to 8%, 0.5% to 7%, 0.5% to 6%, 0.5% to 5%, 0.5% to 4%, 0.5% to 3%, 0.5% to 2%, 0.5% to 1%, 1% to 10%, 1% to 9%, 1% to 8%, 1% to 7%, 1% to 6%, 1% to 5%, 1% to 4%, 1% to 3%, 1% to 2%, 1.5% to 10%, 1.5% to 9%, 1.5% to 8%, 1.5% to 7%, 1.5% to 6%, 1.5% to 5%, 1.5% to 4%, 1.5% to 3%, 1.5% to 2%, 2% to 10%, 2% to 9%, 2% to 8%, 2% to 7%, 2% to 6%, 2% to 5%, 2% to 4%, or 2% to 3%. In some preferred embodiments, the amount of Active Ingredient in the formulation is 0.1%, 0.3%, 0.5%, 0.8%, 1.0%, 1.2%, 1.4%, 1.6%, 1.8% or 2%; and more preferably 1.0%.

Solvents

The compositions of the present application are based on a hydroalcoholic chassis, and therefore comprise, as the main solvent, a mixture of water and an alcohol. In various embodiments using water as the solvent, the formulations comprise (wt/wt): about 0.1% to about 75%, about 10% to about 65%, about 15% to about 60%, about 20% to about 55% of water, about 25% to about 55%, about 30% to about 55%, about 35% to about 55%, about 40% to about 52%, or about 45% to about 52%. In some embodiments, the amount of water in the formulation is about 0.1%, 0.5%, 10%, 22%, 31%, 47%, 48%, 48.9%, 49%, 50%, 50.1% 50.3%, 50.7%, 58%, 59%, 60%, 62%, 65%, 68%, 73%, or 75%. In other embodiments using alcohol as the solvent, the formulations comprise (wt/wt): about 10% to about 60%, about 15% to about 55%, about 20% to about 50%, or about 30% to 40% of alcohol.

In an embodiment, the water component of the hydroalcoholic chassis is buffered. Alternately or additionally, the water component is adjusted with a pH adjusting agent.

In some embodiments, the alcohol is a lower alkyl alcohol or a mixture of lower alkyl alcohols. In a further embodiment, the alcohol is a monohydric alcohol. In a further embodiment, the alcohol is ethanol, isopropanol, or 2-(2-ethoxyethoxy) ethanol (transcutol), or a mixture thereof. In some embodiments, the amount of 2-(2-ethoxyethoxy) ethanol (transcutol) in the formulation is about 0.1% to 25%; about 2% to 12%; about 5% to 10%; or about 6% to 8%. In some embodiments, the amount of 2-(2-ethoxyethoxy) ethanol (transcutol) in the formulation is about 0.1%, 0.5%, 1%, 2%, 3%, 4%, 5%, 6%, 7%, 8%, 9%, 10%, 12%, 15%, 18%, 23%, or 25%.

In one embodiment the compositions of the present invention are formulated with organic solvents. Examples of organic solvents include acetic acid; acetone; acetonitrile; 1-butanol; 2-butanol; 2-butanone; tert-butyl alcohol; cyclohexane; diethylene glycol; diethyl ether; diglyme (diethylene glycol); dimethyl ether; 1,2-dimethoxy-ethane (glyme or "DME"); dimethylformamide ("DMF"); DMSO; 1,4-dioxane; ethanol; ethyl acetate; ethylene glycol; glycerin; heptane; Hexamethylphosphoramide (HMPA); Hexamethylphosphorous triamide (HMPT); hexane; methanol; methyl t-butyl ether (MTBE); methylene chloride; N-methyl-2-pyrrolidinone ("NMP"); nitromethane; pentane; petroleum ether (ligroine); 1-propanol; 2-propanol; pyridine; tetrahydrofuran ("THF"); toluene; triethylamine; o-xylene; m-xylene; p-xylene. Particularly preferred organic solvents for use in the compositions include substances that are pharmaceutically acceptable for application to the skin. In one embodiment the compositions include at least two organic solvents, while some embodiments have more than two organic solvents. In a further aspect, the formulations may have different volatilities. In a preferred embodiment one of the solvents is highly volatile such that the formulation substantially dries relatively quickly on application to the skin of a subject while the second solvent is less volatile and serves to maintain the donepezil or a salt thereof in a substantially solubilized form in order that the donepezil or a salt thereof can continue to be efficiently delivered into the skin of the subject.

Without being bound by theory, it is a further aspect of the application that the solvent can additionally or alternately function as a molecular penetration enhancer.

MPE

The compositions and formulations for the present invention may include one or more MPEs. Examples of MPEs include, but are not limited to (+/−)-limonene; 1,3-butanediol; alpha-terpineol; alpha-tocopherol; ammonium lauryl sulfate; butylene dioxide; caprylic/capric triglycerides; castor oil; cedar leaf oil; ceteareth-12; ceteareth-15; ceteareth-30; ceteth-10; ceteth-2; ceteth-20; ceteth-23; Choleth-24; coco-caprylate/caprate; cocodiethanolamide; corn oil; cyclomethicone; dichlorodifluoromethane; diethanolamine; diethylene glycol monomethyl ether; diethylsebacate; diisopropanolamine; diisopropyl adipate; diisopropyl dilinoleate; dimethyl isosorbide; dimethyl sulfoxide; dipropylene glycol; ethyl acetate; ethyl oleate; ethylene glycol; fatty acids; glycerin; glycerol; glyceryl isostearate; glyceryl laurate; glyceryl monooleate (Capmul® GMO-50); glyceryl monostearate; glyceryl palmitate; glyceryl rincoleate; glyceryl stearate-laureth 23; hexylene glycol; hydrogenated castor oil; imidurea; isoceteth-20; isopropyl alcohol; isopropyl isostearate; isopropyl myristate; isopropyl palmitate; Labrasol®; lactic acid; lauramine oxide; laureth-2; laureth-23; laureth-4; lauric diethanolamide; lauric/myristic diethanolamide; lauryl acetate; lauryl lactate; levulinic acid; L-menthol; Medium chain triglycerides; methoxy PEG-16; methyl alcohol; methyl gluceth-10; methyl laurate; methyl salicylate; myristyl alcohol; myristyl lactate; octyldodecanol; oleic acid; oleth-10; oleth-2; oleth-20; oleth-5; oleyl alcohol; oleyl oleate; PEG-60 hydrogenated castor oil; PEG-methyl ether; pentadecalactone; polyethylene glycol 400; polyoxyl 40 hydrogenated castor oil; polysorbate 20; polysorbate 40; polysorbate 60; polysorbate 65; polysorbate 80; propylene carbonate; propylene glycol; propylene glycol diacetate; propylene glycol dicaprylate; propylene glycol monolaurate; propylene glycol monopalmitostearate; SD alcohol 408; sodium lactate; sodium laureth-2 sulfate; sodium laureth-3 sulfate; sodium lauryl sulfate; sorbitan isostearate; sorbitan monolaurate; sorbitan monooleate; sorbitan monopalmitate; sorbitan monostearate; sorbitan sesquioleate; sorbitan tristearate; sorbitol; soybean oil; spermaceti; squalene; steareth-10; steareth-100; steareth-2; steareth-20; steareth-21; steareth-40; tocopherol; Transcutol®; trideceth-10; triethanolamine lauryl sulfate; trolamine; and urea.

Preferably the formulations used herein include more than one MPE, and preferably a combination of a monohydric alcohol and a saturated fatty acid. Also, preferably, the MPE used in some embodiments are lauryl lactate, limonene, transcutol, ethyl oleate, isopropyl myristate, isopropyl palmitate, methyl laurate. In the preferred embodiments provided herein preferred MPEs are combinations of transcutol, isopropyl palmitate, and isopropyl myristate; and more preferably a combination of transcutol and isopropyl palmitate. The aforementioned combination are preferred for the donepezil base formulations.

Alcohol

In one preferred aspect, the compositions and formulations provided herein include a monohydric alcohol. Suitable monohydric alcohols include, but are not limited to, ethanol, propanol, propan-2-ol, (isopropanol), butanol, butan-2-ol (isobutanol), pentanol, pentan-2-ol, pentan-3-ol, 3-methyl-2-butanol, hexanol, hexan-2-ol, hexan-3-ol, benzyl alcohol and the like, as well as a mixture thereof.

In another preferred aspect the formulations include a lower alcohol. In certain preferred aspects, the monohydric alcohol is ethanol. In certain preferred aspects the ethanol is present in an amount of up to about 90% w/w. More preferably, ethanol is present in an amount of up to about 60% w/w or up to about 40% w/w In one preferred aspect, the compositions and formulations include a diol. Suitable diols include, but are not limited to, propylene glycol, butanediol, butynediol, pentanediol, hexanediol, octanediol, neopentyl glycol, 2-methyl-1,3-propanediol, diethylene glycol, triethylene glycol, tetraethylene glycol, dipropylene glycol, dibutylene glycol, and the like, as well as a mixture thereof. In one aspect, the formulation comprises up to about 50% of a diol, and preferably up to about 35%. In certain preferred aspects, the diol is a glycol, such as ethylene glycol, propylene glycol, or a mixture thereof. More preferably, the diol is propylene glycol. In some embodiments, the amount of propylene glycol in the formulation is about 0.1% to 25%; about 2% to 12%; about 5% to 10%; or about 6% to 8%. In some embodiments, the amount of propylene glycol in the formulation is about 0.1%, 0.5%, 1%, 2%, 3%, 4%, 5%, 6%, 7%, 8%, 9%, 10%, 12%, 15%, 18%, 23%, or 25%.

In still another aspect, the formulation includes at least two alcohols. Preferably, the formulation includes a monohydric alcohol and a diol. More preferably, the monohydric alcohol is ethanol. More preferably, the diol is propylene glycol. Still more preferably, the monohydric alcohol is ethanol, and the diol is propylene glycol. In especially preferred embodiment the ethanol and propylene glycol are present in approximately equal amounts.

Water

In certain aspects, the compositions include water. Preferably, water is present from about 10% to 95% w/w such as about 10, 15, 20, 25, 30, 35, 40, 45, 50, 55, 60, 65, 70, 75, 80, 85, 90 or 95% w/w. More preferably, the composition includes from about 20% to 60%, about 30 to 60%, about 40 to 60%, about 50 to 60%, about or about 55% to 60% w/w water. In some embodiments, the compositions include about 40%, 45%, 50%, 55%, or 60% w/w water, and preferably 40.3%, 55.5%, 56.9%, or 59.5%. In other preferred embodiments the compositions are anhydrous in nature and contain no water or contain only trace amounts of water. In some embodiments, the amount of water in the formulation is about 0.1% to 75%, about 10% to about 65%, about 15% to about 60%, about 20% to about 55% of water, about 25% to about 55%, about 30% to about 55%, about 35% to about 55%, about 40% to about 52%, or about 45% to about 52%. In some embodiments, the amount of water in the formulation is about 0.1%, 0.5%, 10%, 22%, 31%, 47%, 48%, 48.9%, 49%, 50%, 50.1% 50.3%, 50.7%, 58%, 59%, 60%, 62%, 65%, 68%, 73%, or 75%.

Polyether

In one preferred aspect, the compositions and formulations include a polyethylene glycol ("PEG") a polyether compound with the general formula H—(O—CH2-CH2)n-OH (also known as polyethylene oxide ("PEO") or polyoxyethylene ("POE"), depending on its molecular weight). Most PEGs comprise molecules that are polydisperse, that is with a distribution of molecular weights. Suitable PEGs include those with average molecular weights of approximately 300 daltons (labeled PEG 300), 400 daltons (PEG 400), 600 daltons (PEG 600), or 1450 daltons (PEG 1450). Preferably, the polyether is PEG 400, PEG600, or PEG 1450.

In some embodiments, formulations include PEG400 in wt/wt % of 10%, 15%, 20%, 25%, 30%, or 35%; and preferably 26%. In some embodiments, formulations include PEG600 in wt/wt % of 2%, 4%, 6%, 8%, 10%, or 12%; and preferably 5%. In some embodiments, formulations include PEG1450 in wt/wt % of 2%, 4%, 6%, 8%, 10%, 12%; and preferably 5%. In some preferred embodiments, formulations have combinations of polyethers, preferably PEG400 and PEG600.

Triglyceride

In one preferred aspect, the compositions and formulations include a triglyceride, an ester derived from glycerol and three fatty acids.

In one preferred aspect the triglyceride comprises one or more fatty acids that contain 16, 18, or 20 carbon atoms. In another preferred aspect the triglyceride is a fully saturated triglyceride. In a particularly preferred aspect the triglyceride is glycerol triester with caprylic and capric acids, termed caprylic/capric triglyceride (CAS 65381 Sep. 1; Crodamol™ GTCC from Croda (Edison NJ)). Preferably, formulation include caprylic/capric triglyceride in wt/wt % of 4%, 5%, 6%, 7%, or 8%, and more preferably 5%.

Fatty Alcohol

In one preferred aspect, the compositions and formulations include a fatty alcohol. Suitable fatty alcohols include tert-butyl alcohol; tert-amyl alcohol; 3-methyl-3-pentanol; ethchlorvynol; loctanol (capryl alcohol); pelargonic alcohol (1-nonanol); 1-decanol (decyl alcohol, capric alcohol); undecyl alcohol (1-undecanol, undecanol, hendecanol); lauryl alcohol (dodecanol, 1-dodecanol); tridecyl alcohol (1-tridecanol, tridecanol, isotridecanol); myristyl alcohol (1-tetradecanol); pentadecyl alcohol (1 pentadecanol, pentadecanol); cetyl alcohol (1-hexadecanol); palmitoleyl alcohol (cis-9-hexadecen-1-ol); heptadecyl alcohol (1-n-heptadecanol, heptadecanol); stearyl alcohol (1-octadecanol); oleyl alcohol (1octadecenol); nonadecyl alcohol (1-nonadecanol); arachidyl alcohol (1-eicosanol); heneicosyl alcohol (1heneicosanol); behenyl alcohol (1-docosanol); erucyl alcohol (cis-13-docosen-1-ol); lignoceryl alcohol (1tetracosanol); ceryl alcohol (1-hexacosanol); 1-heptacosanol; montanyl alcohol, cluytyl alcohol, or loctacosanol; 1-nonacosanol; myricyl alcohol, melissyl alcohol, or 1-triacontanol; 1-dotriacontanol (lacceryl alcohol); geddyl alcohol (1-tetratriacontanol); and cetearyl alcohol.

Preferred embodiments include the fatty alcohol cetyl alcohol, and preferably in wt/wt % of 2%, 3%, 4%, 5%, 6%, 7%, 8%, 9%, 10%, or 11%; and more preferably 3%, 5%, 9%, 10%, or 11%.

Thickening Agent

In one preferred aspect, the viscosity of the compositions and formulations is adjusted by incorporation of a thickening agent. Exemplary thickening agents include alginic acid, sodium alginate, cellulose polymers, carbomer polymers (carbopols), carbomer derivatives, cellulose derivatives (such as carboxymethyl cellulose, ethylcellulose, hydroxyethyl cellulose and hydroxypropyl cellulose), hydroxypropyl methyl cellulose (HPMC), polyvinyl alcohol, poloxamers (Pluronics®), polysaccharides (such as chitosan or the like), natural gums (such as acacia (arabic), tragacanth, xanthan and guar gums), gelatin, bentonite, bee wax, magnesium aluminum silicate (Veegum®) and the like, as well as mixtures thereof.

The nature of the thickener and the thickener concentration is chosen so as to produce a formulation of the desired viscosity, as is familiar to one skilled in the art. In certain preferred aspects, the thickening agent is hydroxypropyl cellulose ("HPC") of which a commercial example is 'HY119' hydroxypropyl cellulose NF (CAS number (Spectrum Chemical, Gardena CA), or HPMC (Methocel E4M). Preferably, formulations include the thickening agents HY119 or HPMC, the HY119 present in wt/wt % of 2%, 3%, 4%, or 5%, and preferably 3%, and the HPMC present in wt/wt % of 0.3%, 0.4%, 0.5%, 0.6% or 0.7%, and preferably 0.5%. In another preferred aspect the inclusion of a thickener in the formulation results in a gel or a light gel.

Emollients

Emollients can optionally be added to the formulations of the invention so that the formulations can maintain or increase the moisture content of the stratum corneum when the composition is applied to the skin. Emollients may be added to the formulations in addition to the other components described herein, which may also aid in maintaining or improving the skin condition of the user.

In one aspect, added emollients are included in the compositions of the invention at a concentration between about 0.1 and 20% w/w. In another aspect, the added emollient can be present in the composition at a concentration between about 0.5% and 10% w/w. In still another aspect, the emollient concentration can be between about 1% and 5% w/w.

In some embodiments, the emollient is a bee wax. In some embodiments, the amount of bee wax in the formulation is about 0.1% to about 25%; about 0.5% to about 20%; about 1% to about 15%; about 1% to about 12%; about 1% to about 10%; about 1% to about 9%; about 1% to about 8%; about 2% to about 8%; about 3% to about 8%; about 4% to about 8%; or about 4% to about 7%. In some embodiments, the amount of bee wax in the formulation is about 0.1%, 0.5%, 1%, 2%, 3%, 4%, 4.8%, 4.9%, 5%, 5.1%, 5.2%, 6%, 7%, 8%, 9%, 10%, 11%, 12%, 13%, 14%, 15%, 16%, 17%, 18%, 19%, or 20%.

Emollients are generally separated into two broad classes based on their function. The first class of emollients functions by forming an occlusive barrier to prevent water evaporation from the stratum corneum. The second class of emollients penetrate into the stratum corneum and physically bind water to prevent evaporation. The first class of emollients is subdivided into compounds which are waxes at room temperature and compounds which are liquid oils. The second class of emollients includes those which are water soluble and are often referred to as humectants.

Suitable emollients may be selected from any of the classes known in the art. A general list of useful emollients appears, for example, in U.S. Pat. No. 4,478,853 and in EP patent application 0 522 624A1 as well as in the CTFA Cosmetic Ingredient Handbook published by The Cosmetic, Toiletry, and Fragrance Association, Washington D.C. (1992) under the listings "Skin Conditioning agents", "emollients", "humectants", "miscellaneous" and "occlusive."

The addition of one or more emollients may affect the viscosity and stability of the compositions of the present invention. In some embodiments, a single emollient may be added to the composition. In other embodiments, two or more emollients may be added to the composition. While any of a variety of emollients may be added to the formulations of the present invention, some embodiments will include wax and oil type emollients either alone or combined with water soluble emollients. In some embodiments of the invention, emollient systems can be comprised of humectants in addition to occlusive wax and oil emollients in concentrations that achieve a moisturizing effect and which maintain and improve the condition of the skin upon repeated use. Emollients may be non-comedogenic and chosen to avoid skin irritation or sensitization reactions.

Fatty Acids

In one aspect the formulations and compositions of the present invention may include an ester of a fatty acid or a triglyceride, an ester derived from glycerol and three fatty acids. Examples of unsaturated fatty acids include, but are not limited to: α-linolenic acid (C18:3); stearidonic acid (C18:4); eicosapentaenoic acid (C20:5); docosahexaenoic acid (C22:6); linoleic acid (C18:2); linolelaidic acid (C18:2); γ-linolenic acid (C18:3); dihomo-γ-linolenic acid (C20:3); arachidonic acid (C20:4); docosatetraenoic acid (C22:4); palmitoleic acid (C16:1); vaccenic acid (C18:1); paullinic acid (C20:1); oleic acid (C18:1); elaidic acid (C18:1); gondoic acid (C20:1); erucic acid (C22:1); nervonic acid (C24:1); and mead acid (C20:3).

Examples of saturated fatty acids include, but are not limited to: caproic acid (C6:0); enanthic acid (C7:0); caprylic acid (C8:0); pelargonic acid (C9:0); capric acid (C10:0); undecylic acid (C11:0); lauric acid (C12:0); tridecylic acid (C13:0); myristic acid (C14:0); pentadecylic acid (C15:0); palmitic acid (C16:0); margaric acid (C17:0); stearic acid (C18:0); nonadecylic acid (C19:0); arachidic acid (C20:0); heneicosylic acid (C21:0); and behenic acid (C22:0).

Fatty Acid Esters

In one aspect the formulations and compositions of the present invention may include a fatty acid ester.

The fatty acid esters of the present invention result from the combination of an unsaturated fatty acid or a saturated fatty acid with a monohydric alcohol. In certain preferred aspects, the fatty acid is lauric acid (C12:0), myristic acid (C14:0), or palmitic acid (C16:0). In certain preferred aspects, the monohydric alcohol is isopropyl alcohol. In certain preferred aspects, the fatty acid ester is isopropyl palmitate or isopropyl myristate.

Preferably, formulations include the fatty acid esters isopropyl palmitate or isopropyl myristate, the isopropyl palmitate present in wt/wt % of 2%, 3%, 4%, 5%, 6%, 7%, 8%, 9%, or 10%, and more preferably 7%, and the isopropyl myristate present in wt/wt % 5%, 6%, 7%, 8%, 9%, 10%, 11%, 12% or 13%, and more preferably 10%. In some preferred embodiments, the fatty acid esters included in the formulation are a combination of isopropyl palmitate and isopropyl myristate.

Solubilizing Agent

In one aspect the formulations and compositions of the present invention may include a solubilizing agent. Examples of solubilizing agents include, but are not limited to: 2-hydroxypropyl-βcyclodextrin; benzalkonium chloride; benzethonium chloride; cetylpyridinium chloride; Cremophor EL; dimethyl sulfoxide; docusate sodium; ethanol; Gelucire 44/14; Labrasol; Nonoxynol 9; Octoxymol 9; PEG-60 Hydrogenated Castor Oil (HCO-60); Poloxamer 124; Poloxamer 188; Poloxamer 237; Poloxamer 338; Poloxamer 407; Poloxamer; Polyethylene glycol 300 (PEG 300); Polyethylene glycol 400 (PEG 400); Polyoxyl 10 Oleyl Ether; Polyoxyl 20 Cetostearyl Ether; Polyoxyl 35 Castor Oil; Polyoxyl 40 Hydrogenated Castor Oil; Polyoxyl 40 Stearate; Polysorbate 20 (or Tween 20); Polysorbate 40; Polysorbate 60; Polysorbate 80 (or Tween 80); propylene glycol; sodium lauryl sulfate; sodium taurocholate; sorbitan monolaurate (or Span 20); sorbitan monooleate (or Span 80); sorbitan monopalmitate (or Span 40); sorbitan monostearate (or Span 60); sulfobutylether-β-cyclodextrin (Captisol); Transcutol P; Brij L23, Brij L4,, Brij S20, and Tyloxapol. The molecule transcutol and transcutol P are used herein interchangeably, but for any pharmaceutical application the pharma grade Transcutol P is preferred.

Preferably, the formulations include the solubilizing agent Transcutol, Polysorbate 20 (or Tween 20), Tween 80, sorbitan monolaurate (or Span 20), Brij L4, or propylene glycol, or a combination thereof. In the embodiments with Transcutol, preferably the wt/wt % of Transcutol is 6%, 7%, 8%, 9%, 10%, 11%, 12%, 13%, 14%, 15%, 16%, 17%, 18%, 19%, 20%, 21%, or 22%; and more preferably 7%. In the embodiments with Polysorbate 20 (or Tween 20), preferably the wt/wt % of Polysorbate 20 (or Tween 20) is 1.8%, 1.9%, 2.0%, 2.1%, 2.2%, 2.3%, 2.4%, 2.5%, 3.3%, 4.2%, 4.4%, 5.2%, 6.5%, or 8.0%; and more preferably 2.0%, 2.1%, 2.2%, 3.3%, 4.2%, or 4.4%. In the embodiments with Tween 80, preferably the wt/wt % of Tween 80 is 3.0%, 3.05%, 3.1%, 3.15%, 3.2%, or 3.25%; and more preferably 3.11%. In the embodiments with Transcutol, preferably the wt/wt % of sorbitan monolaurate (or Span 20) is 2.5%, 2.6%, 2.7%, 2.8%, 2.9%, 3.0%, 3.1%, 3.2%, 3.3%, 3.4%, 3.5%, 3.6%, 3.8%, 4.9%, 5.2%, 6.9%, or 8.0%; and more preferably 2.8%, 2.9%, 3.0%, 3.6%, 3.8%, or 4.9%. In the embodiments with Brij L4, preferably the wt/wt % of Brij L4 is 4.0%, 4.1%, 4.2%, 4.3%, 4.4%, 4.5%; and more preferably 4.38%, 4.386% or 4.39%.

Sunscreens

In one aspect the formulations of the present inventions can also contain a sunscreen agent. The sunscreen agent may be included to slow the degradation of the vitamin D in the formulations that results from exposure to ultraviolet light. Sunscreen agents include p-aminobenzoic acid, Padimate O, phenylbenzimidazole sulfonic acid, cinoxate, dioxybenzone, oxybenzone, Homosalate, Menthyl anthranilate, octocrylene, octyl methoxycinnamate, octyl salicylate, sulisobenzone, trolamine salicylate, avobenzone, ecamsule, titanium dioxide and zinc oxide. Other sunscreen agents include 4-Methylbenzylidene camphor, Tinosorb M, Tinosorb S, Tinosorb A2B, Neo Heliopan AP, Mexoryl XL, benzophenone-9, Uvinul T 150, Uvinul A Plus, Uvasorb HEB, Parsol SLX and Amiloxate.

Antioxidant

In one aspect, the formulations can additionally comprise an anti-oxidant. Preferred anti-oxidants for use in the present invention include ascorbic acid, ascorbyl linoleate, ascorbyl dipalmitate, ascorbyl palmitate, ascorbyl tocopherol maleate, butylated hydroxytoluene, butylated hydroxyanisole (BHA), calcium ascorbate, carotenoids, kojic acid and its pharmaceutically acceptable salts, propyl gallate, sodium thiosulfate, thioglycolic acid and its pharmaceutically acceptable salts (e.g., ammonium), tocopherol (including α, β, γ and δ forms), tocopherol acetate, tocophereth-5, tocophereth-12, tocophereth-18, or tocophereth-80.

Preservative

In one aspect, some formulations additionally comprise at least one preservative. Preferred preservatives for use in the present invention include benzalkonium chloride, cetrimonium bromide (aka cetyltrimethylammonium bromide), cetylpyridinium chloride, benzethonium chloride, alkyltrimethylammonium bromide, methyl paraben, ethyl paraben, propyl paraben, butyl paraben, benzyl alcohol, steryl alcohol, benzoic acid, sorbic acid, chloroacetamide, trichlorocarban, thimerosal, imidurea, bronopol, chlorhexidine, 4-chlorocresol, 4-chloroxylenol, dichlorophene and hexachlorophene. Especially preferred are cetylpyridinium chloride, methyl paraben and propyl paraben, or mixtures thereof.

Chelating Agent

In one aspect the formulation additional comprises at least one chelating agent. A suitable chelating agent includes ethylenediaminetetraacetic acid ("EDTA").

pH

In still another aspect, the formulation is acidic. In certain aspects, the formulation has a pH of below about 7.5, 6.5, 5.5, 4.5, 3.5, or 2.5. In certain other aspects, the pH of the formulation may range from about 1.5 to 7, about 2 to 7, about 3 to 7, about 4 to 7, or about 5 to 7. In still other aspects, the pH of the formulation may range from about 1.5 to 5.5, about 2.5 to 5.5, about 3.5 to 5.5, or about 4.5 to 5.5. The formulation may include a pH adjusting agent to maintain its acidic pH. Preferably, the formulation has a pH value between about 4 and 7.

In yet another aspect, the formulation is basic. In certain aspects, the formulation has a pH of above about 7, 8, 9, 10, 11, or 12. In certain other aspects, the pH of the formulation may range from about 7 to 12.5, about 7 to 11.5, about 7 to 10.5, about 7 to 9.5, or about 7 to 8.5. In still other aspects, the pH of the formulation may range from about 9 to 12.5, about 9 to 11.5, about 9 to 10.5, or about 8.5 to 10. The formulation may include a pH adjusting agent to maintain its basic pH. Preferably, the formulation has a pH value between about 7 and 10.

In still yet another aspect, the formulation is neutral. In certain aspects, the formulation has a pH of about 7. In certain other aspects, the formulation has a pH from about 6 to about 8.5, from about 5.5 to 8, about 6 to 8, about 6.5 to 8.5, or from about 6.5 to 7.5. The formulation may include a pH adjusting agent to maintain its neutral pH. Preferably, the formulation has a pH value between about 6 and 8.5. In one embodiment the pH adjusting agent is an acid, such as, hydrochloric acid or acetic acid. In another embodiment, the pH adjusting agent is a base, such as sodium hydroxide. In a further embodiment the pH adjusting agent is a buffer, such as, a phosphate butter or a citrate buffer.

In yet another aspect the formulation is comprised mostly or entirely of organic molecules and, as such, pH in the conventional sense may not be a meaningful concept.

Preferable embodiments include formulations of donepezil having the following components with the wt/wt % (formulation F160):

Donepezil preferably 1.0%
Ethanol preferably 40.0%
PEG 400 preferably 26.0%
PEG 600 preferably 5.0%
Transcutol preferably 20.0%
Isopropyl palmitate preferably 5.0%
HY 119 preferably 3.0%

Preferable embodiments include formulations of donepezil hydrochloride having the following components with the wt/wt % (formulation F162):

Donepezil HCl preferably preferably 1.0%
Water preferably 40.3%
Transcutol preferably 7%
Propylene glycol preferably 7%
Cetyl alcohol preferably 10%
Isopropyl myristate preferably 10%
Capric/Caprylic triglycerides GTCC preferably 10%
Isopropyl palmitate preferably 7%
Brij L4 preferably 4.386%
Tween 80 preferably 3.114%
Xanthum gum preferably 0.2%

Preferable embodiments include formulations of donepezil hydrochloride having the following components with the wt/wt % (formulation F165):

Donepezil HCl preferably 1%
Transcutol preferably 7%
Propylene glycol preferably 7%
Cetyl alcohol preferably 3%
Capric/Caprylic triglycerides GTCC preferably 5%
Isopropyl palmitate preferably 7%
Bee wax preferably 5%
Span 20 preferably 4.9% or 4.8%
Tween 20 preferably 3.3% or 3.2%
Water preferably 56.9%

Preferable embodiments include formulations of donepezil hydrochloride having the following components with the wt/wt % (formulation F164A):

Donepezil HCl preferably 1.0%
Cetyl alcohol preferably 5%
Capric/Caprylic triglycerides GTCC preferably 5%
Isopropyl palmitate preferably 7%
White Wax preferably 7%
Transcutol preferably 7%
Propylene glycol preferably
7% Water preferably 55.5%
Span 20 preferably 2.9%
Tween 20 preferably 2.1%
HPMC preferably 0.5%

Preferable embodiments include formulations of donepezil hydrochloride having the following components with the wt/wt % (formulation F164B):

Donepezil HCl preferably 1.0%
Cetyl alcohol preferably 3%
Capric/Caprylic triglycerides GTCC preferably 5%
Isopropyl palmitate preferably 7%
White Wax preferably 5%
Transcutol preferably 7%
Propylene glycol preferably 7%
Water preferably 59.5%
Span 20 preferably 3%
Tween 20 preferably 2%
HPMC preferably 0.5%

Preferable embodiments include formulations of donepezil hydrochloride having the following components with the wt/wt % (formulation F164C):

Donepezil HCl preferably 1.0%
Cetyl alcohol preferably 5%
Isopropyl palmitate preferably 7%
White Wax preferably 5%
Transcutol preferably 7%
Propylene glycol preferably 7%
Water preferably 55.5%
Span 20 preferably 2.8%
Tween 20 preferably 2.2%
HPMC preferably 0.5%
Mineral oil preferably 5.0%

Preferable embodiments include formulations of donepezil hydrochloride having the following components with the wt/wt % (formulation F183):

Donepezil HCl preferably 1%
Transcutol preferably 7%
Propylene glycol preferably 7%
Cetyl alcohol preferably 11%
Capric/Caprylic triglycerides GTCC preferably 5%
Isopropyl palmitate preferably 7%
Bee wax preferably 5%
Span 20 preferably 4.9% or 4.8%
Tween 20 preferably 3.3% or 3.2%
Water preferably 48.9%

Preferable embodiments include formulations of donepezil hydrochloride having the following components with the wt/wt % (formulation F186):

Donepezil HCl preferably 1%
Transcutol preferably 7%
Propylene glycol preferably 7%
Cetyl alcohol preferably 9%
Capric/Caprylic triglycerides GTCC preferably 5%
Isopropyl palmitate preferably 7%
Bee wax preferably 5%
Span 20 preferably 3.9% or 3.8%
Tween 20 preferably 4.1% or 4.2%
Water preferably 51.9%

Preferable embodiments include formulations of donepezil hydrochloride having the following components with the wt/wt % (formulation F187):

Donepezil HCl preferably 1%
Transcutol preferably 7%
Propylene glycol preferably 7%
Cetyl alcohol preferably 11%
Capric/Caprylic triglycerides GTCC preferably 5%
Isopropyl palmitate preferably 7%
Bee wax preferably 5%
Span 20 preferably 3.7% or 3.6%
Tween 20 preferably 4.3% or 4.4%
Water preferably 49.0%

Thus, the present invention consists of a method of treating skin diseases or problems of a mammal, which may be human, by the topical administration to the site of the disease or problem at least one of the formulations of donepezil or donepezil HCl, described herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Analytical Methods

A high performance liquid chromatography ("HPLC") method was used to assay the concentrations of donepezil and donepezil HCl. The mobile phases, column, and chromatographic conditions were similar for both donepezil HCl and donepezil base. An outline of the method details is provided in Table 1 below.

TABLE 1

Chromatographic parameters for donepezil detection.

| Method Name | Donepezil (AA2017.013) |
|---|---|
| Instrument | 1100-HPLC/UV |
| Column | Poroshell 120 EC-C18 100 × 4.6, 4 μm |
| | Guard EC-C18 5 × 4.6, 2.7 μm |
| Column temp | 40° C. |
| UV Detection | 270 nm |
| Mobile phase A | Water w/0.1% phosphoric acid |
| Mobile phase B | Acetonitrile |
| Flow rate | 1.00 mL/min |
| Gradient | 0 minutes: 90% Mobile phase A |
| | 2 minutes: 90% Mobile phase A |

TABLE 1-continued

Chromatographic parameters for donepezil detection.

| | 7 minutes: 5% Mobile phase A |
|---|---|
| | samples: additional 2 min at 95% |
| | post time: 2 min |
| $V_{inj}$ (μl) | 10 μL |

Example 2: Formulation Preparation

Numerous test article formulations were prepared as listed in Table 2A through Table 2G (the formulations grouped according to the diffusion study they were tested in). Formulations Arctic F1-Arctic F133 are all free-flowing solutions (with the exception of formulations with a "G" at the end which have the addition of hydroxy propyl cellulose). The simple solution formulations were prepared by adding all the ingredients together, including the Active, and sonicating until all the ingredients were dissolved and fully dispersed. Formulations Arctic F134-F165 consisted of cream or gel formulations.

Gel formulations were prepared by first mixing all the ingredients, with the exception of the thickening agent, and sonicating/vortexing until the ingredients were fully dispersed/dissolved. To this solution, the thickening agent was added. The resulting mixture was then allowed to rotate on a rotisserie until the gallant was fully swollen and the formulation fully mixed (typical ~24 hours).

Cream formulations were prepared by separately preparing an oil phase (consisting of the oil soluble ingredients) and a water phase (consisting of water soluble ingredients). The two phases were mixed with an overhead mixer while heating the formulations at 60° C. Any additional cosolvents (e.g. ethanol, Transcutol, and propylene glycol) were then added, and the resulting mixture further mixed until homogeneous.

TABLE 2A

All formulations were free flowing solutions. Corresponding flux studies in which they were ran at listed according to the dated experiment code (e.g. "May 1, 2017ArcTor Q95").

Apr. 6, 2017ArctFlx Q95

| | Formulation name | | | | | | | | | |
|---|---|---|---|---|---|---|---|---|---|---|
| Ingredient | Artic F1 wt/wt % | Artic F2 wt/wt % | Artic F3 wt/wt % | Artic F4 wt/wt % | Artic F5 wt/wt % | Artic F6 wt/wt % | Artic F7 wt/wt % | Artic F8 wt/wt % | Artic F9 wt/wt % | Artic F10 wt/wt % |
| Donepezil HCl | 1.0 | 1.0 | 1.0 | 1.0 | 1.0 | 1.0 | 1.0 | 1.0 | 1.0 | 1.0 |
| Water | 99.0 | | | | | | | | | |
| Transcutol | | 99.0 | | | | | | | | |
| Dimethyl sulfoxide | | | 99.0 | | | | | | | |
| Benzyl alcohol | | | | 99.0 | | | | | | |
| Ethanol | | | | | 99.0 | | | | | |
| Glycerin | | | | | | 99.0 | | | | |
| Hexylene glycol | | | | | | | 99.0 | | | |
| PEG 300 | | | | | | | | 99.0 | | |
| Propylene glycol | | | | | | | | | 99.0 | |
| Lauric diethanolamide | | | | | | | | | | 99.0 |

TABLE 2A-continued

All formulations were free flowing solutions. Corresponding flux studies in which they were ran at listed according to the dated experiment code (e.g. "May 1, 2017ArcTor Q95").

Apr. 13, 2017ArctFlx Q95

Formulation name

| Ingredient | Artic F3 wt/wt % | Artic F11 wt/wt % | Artic F12 wt/wt % | Artic F13 wt/wt % | Artic F14 wt/wt % | Artic F15 wt/wt % | Artic F16 wt/wt % | Artic F17 wt/wt % | Artic F18 wt/wt % | Artic F19 wt/wt % |
|---|---|---|---|---|---|---|---|---|---|---|
| Donepezil HCl | 1.0 | 1.0 | 1.0 | 1.0 | 1.0 | 1.0 | 1.0 | 1.0 | 1.0 | 1.0 |
| Dimethyl sulfoxide | 99.0 | 40.0 | 40.0 | 40.0 | 40.0 | 40.0 | 40.0 | 40.0 | 40.0 | 40.0 |
| Transcutol | | 59.0 | | | | | | | | |
| Water | | | 59.0 | | | | | | | |
| Benzyl alcohol | | | | 59.0 | | | | | | |
| Ethanol | | | | | 59.0 | | | | | |
| Glycerin | | | | | | 59.0 | | | | |
| Hexylene glycol | | | | | | | 59.0 | | | |
| PEG 300 | | | | | | | | 59.0 | | |
| Propylene glycol | | | | | | | | | 59.0 | |
| Lauric diethanolamide | | | | | | | | | | 59.0 |

Apr. 20, 2017ArctTor Q95

Formulation name

| Ingredient | Arctic F14 wt/wt % | Arctic F20 wt/wt % | Arctic F21 wt/wt % | Arctic F22 wt/wt % | Arctic F23 wt/wt % | Arctic F24 wt/wt % | Arctic F25 wt/wt % | Arctic F26 wt/wt % | Arctic F27 wt/wt % | Arctic F28 wt/wt % |
|---|---|---|---|---|---|---|---|---|---|---|
| Donepezil HCl | 1.0 | 1.0 | 1.0 | 1.0 | 1.0 | 1.0 | 1.0 | 1.0 | 1.0 | 1.0 |
| Dimethyl sulfoxide | 40.0 | | | | | | | | 20.0 | 20.0 |
| Ethanol | 59.0 | 40.0 | 40.0 | 40.0 | 40.0 | | | | 79.0 | 59.0 |
| Propylene glycol | | 59.0 | | | | 40.0 | 40.0 | 40.0 | | 20.0 |
| Transcutol | | | 59.0 | | | 59.0 | | | | |
| Benzyl alcohol | | | | 59.0 | | | 59.0 | | | |
| Hexylene glycol | | | | | 59.0 | | | 59.0 | | |

May 1, 2017ArcTor Q95

Formulation name

| Ingredient | Arctic F27 wt/wt % | Arctic F29 wt/wt % | Arctic F30 wt/wt % | Arctic F31 wt/wt % | Arctic F32 wt/wt % | Arctic F33 wt/wt % | Arctic F34 wt/wt % | Arctic F35 wt/wt % | Arctic F36 wt/wt % | Arctic F37 wt/wt % |
|---|---|---|---|---|---|---|---|---|---|---|
| Donepezil HCl | 1.0 | 1.0 | 1.0 | 1.0 | 1.0 | 1.0 | 1.0 | 1.0 | 1.0 | 1.0 |
| Dimethyl sulfoxide | 20.0 | 20.0 | 20.0 | | | | 20.0 | | | |
| Ethanol | 79.0 | 59.0 | 40.0 | 40.0 | | | | | | |
| IPA | | | | | | 84.0 | 64.0 | 54.0 | 44.0 | 35.0 |
| Water | | 20.0 | 39.0 | 20.0 | | | | | | |
| Castor oil | | | | | 99.0 | 15.0 | 15.0 | 15.0 | 20.0 | 20.0 |
| Propylene glycol | | | | 39.0 | | | | | | 44.0 |
| Mineral oil | | | | | | | | 30.0 | | |
| Capric Triglyceride | | | | | | | | | 35.0 | |

US 12,582,637 B2

23    24

TABLE 2B

| | | | | | | | | | | |
|---|---|---|---|---|---|---|---|---|---|---|
| All formulations were free flowing solutions. | | | | | | | | | | |

May 5, 2017ArcTor Q95

Formulation name

| Ingredient | Arctic F20 wt/wt % | Arctic F27 wt/wt % | Arctic F34 wt/wt % | Arctic F38 wt/wt % | Arctic F39 wt/wt % | Arctic F40 wt/wt % | Arctic F41 wt/wt % | Arctic F42 wt/wt % | Arctic F43 wt/wt % | Arctic F44 wt/wt % |
|---|---|---|---|---|---|---|---|---|---|---|
| Donepezil HCl | 1.0 | 1.0 | 1.0 | 1.0 | 1.0 | | | | | |
| Donepezil | | | | | | 1.0 | 1.0 | 1.0 | 1.0 | 1.0 |
| Dimethyl sulfoxide | | 20.0 | 20.0 | | 20.0 | 20.0 | 20.0 | | | 20.0 |
| IPA | | | 64.0 | 40.0 | 34.0 | | 64.0 | | 40.0 | 34.0 |
| Castor oil | | | 15.0 | 15.0 | 15.0 | | 15.0 | | 15.0 | 15.0 |
| Ethanol | 40.0 | 79.0 | | | | 79.0 | | 40.0 | | |
| Propylene glycol | 59.0 | | | 44.0 | | | | 59.0 | 44.0 | |
| Capric Triglyceride | | | | | 30.0 | | | | | 30.0 |

May 11, 2017ArctTor

Formulation name

| Ingredient | Arctic F20 wt/wt % | Arctic F27 wt/wt % | Arctic F34 wt/wt % | Arctic F38 wt/wt % | Arctic F39 wt/wt % | Arctic F40 wt/wt % | Arctic F41 wt/wt % | Arctic F42 wt/wt % | Arctic F43 wt/wt % | Arctic F44 wt/wt % |
|---|---|---|---|---|---|---|---|---|---|---|
| Donepezil HCl | 1.0 | 1.0 | 1.0 | 1.0 | 1.0 | | | | | |
| Donepezil | | | | | | 1.0 | 1.0 | 1.0 | 1.0 | 1.0 |
| Dimethyl sulfoxide | | 20.0 | 20.0 | | 20.0 | 20.0 | 20.0 | | | 20.0 |
| IPA | | | 64.0 | 40.0 | 34.0 | | 64.0 | | 40.0 | 34.0 |
| Castor oil | | | 15.0 | 15.0 | 15.0 | | 15.0 | | 15.0 | 15.0 |
| Ethanol | 40.0 | 79.0 | | | | 79.0 | | 40.0 | | |
| Propylene glycol | 59.0 | | | 44.0 | | | | 59.0 | 44.0 | |
| Capric Triglyceride | | | | | 30.0 | | | | | 30.0 |

May 24, 2017ArcTor Q95

Formulation name

| Ingredient | Arctic F34 wt/wt % | Arctic F52 wt/wt % | Arctic F53 wt/wt % | Arctic F54 wt/wt % | Arctic F55 wt/wt % | Arctic F56 wt/wt % | Arctic F57 wt/wt % | Arctic F58 wt/wt % | Arctic F59 wt/wt % | Arctic F60 wt/wt % |
|---|---|---|---|---|---|---|---|---|---|---|
| Donepezil | 1.0 | 1.0 | 1.0 | 1.0 | 1.0 | 1.0 | 1.0 | 1.0 | 1.0 | 1.0 |
| Ethanol | 40.0 | 40.0 | 40.0 | 40.0 | 40.0 | 40.0 | 40.0 | 40.0 | 40.0 | 40.0 |
| Propylene glycol | 49.0 | 49.0 | 49.0 | 49.0 | 49.0 | 49.0 | 49.0 | 49.0 | 49.0 | 49.0 |
| Propylene glycol | 10.0 | | | | | | | 5.0 | 5.0 | 5.0 |
| Diethyl sebacate | | 10.0 | | | | | | | | |
| Diisopropyl adipate | | | 10.0 | | | | | | | |
| Dimethyl isosorbide | | | | 10.0 | | | | | | |
| Dipropylene glycol | | | | | 10.0 | | | | | |
| Hexylene glycol | | | | | | 10.0 | | | | |
| Isopropyl palmitate | | | | | | | 10.0 | | | |
| Brij L23 | | | | | | | | 5.0 | | |
| Brij S20 | | | | | | | | | 5.0 | |
| Brij L4 | | | | | | | | | | 5.0 |

TABLE 2B-continued

All formulations were free flowing solutions.

Jun. 8, 2017ArctTor Q95

Formulation name

| Ingredient | Arctic 34 wt/wt % | Arctic F61 wt/wt % | Arctic F62 wt/wt % | Arctic F63 wt/wt % | Arctic F64 wt/wt % | Arctic F65 wt/wt % | Arctic F66 wt/wt % | Arctic F67 wt/wt % | Arctic F68 wt/wt % | Arctic F69 wt/wt % | Artic F70 wt/wt % |
|---|---|---|---|---|---|---|---|---|---|---|---|
| Donepezil | 1.0 | 1.0 | 1.0 | 1.0 | 1.0 | 1.0 | 1.0 | 1.0 | 1.0 | 1.0 | 1.0 |
| Ethanol | 40.0 | 40.0 | 40.0 | 40.0 | 40.0 | 40.0 | 40.0 | 40.0 | 40.0 | 40.0 | 40.0 |
| Propylene glycol | 59.0 | 29.0 | 29.0 | 39.0 | 49.0 | 54.0 | 54.0 | 54.0 | 49.0 | 49.0 | 49.0 |
| Transcutol | | 30.0 | | | | | | | | | |
| PEG 400 | | | 30.0 | | | | | | | | |
| Diethyl sebacate | | | | 20.0 | | | | | | | |
| Hexylene glycol | | | | | 10.0 | | | | | | |
| Propylene carbonate | | | | | | 5.0 | | | | | |
| Levulinic acid | | | | | | | 5.0 | | | | |
| Lauryl lactate | | | | | | | | 5.0 | | | |
| Limonene | | | | | | | | | 10.0 | | |
| Lauric diethanolamide | | | | | | | | | | 10.0 | |
| Oleyl alcohol | | | | | | | | | | | 10.0 |

TABLE 2C

All formulations were free flowing solutions.

Jun. 15, 2017ArctTor Q95

Formulation name

| Ingredient | Arctic 34 wt/wt % | Arctic F71 wt/wt % | Arctic F72 wt/wt % | Arctic F73 wt/wt % | Arctic F74 wt/wt % | Arctic F75 wt/wt % | Arctic F76 wt/wt % | Arctic F77 wt/wt % | Arctic F78 wt/wt % | Arctic F79 wt/wt % | Arctic F80 wt/wt % |
|---|---|---|---|---|---|---|---|---|---|---|---|
| Donepezil | 1.0 | 1.0 | 1.0 | 1.0 | 1.0 | 1.0 | 1.0 | 1.0 | 1.0 | 1.0 | 1.0 |
| Ethanol | 40.0 | 40.0 | 40.0 | 40.0 | 40.0 | 40.0 | 40.0 | 40.0 | 40.0 | 40.0 | 40.0 |
| Propylene glycol | 59.0 | 54.0 | 49.0 | 49.0 | 49.0 | 54.0 | 54.0 | 54.0 | 49.0 | 49.0 | 49.0 |
| Cocamide DEA | | 5.0 | | | | | | | | | |
| Oleic acid | | | 10.0 | | | | | | | | |
| PEG-7 methyl ether | | | | 10.0 | | | | | | | |
| Polysorbate 80 | | | | | 10.0 | | | | | | |
| Ethyl Oleate | | | | | | 5.0 | | | | | |
| Methyl Laurate | | | | | | | 5.0 | | | | |
| Methyl Salicylate | | | | | | | | 5.0 | | | |
| Capmul GMO | | | | | | | | | 10.0 | | |
| Isopropyl myristate | | | | | | | | | | 10.0 | |
| Crodamol GTCC | | | | | | | | | | | 10.0 |

TABLE 2C-continued

All formulations were free flowing solutions.

Jun. 28, 2017ArctFlx Q95

Formulation name

| Ingredient | Arctic 61 wt/wt % | Arctic F81 wt/wt % | Arctic F82 wt/wt % | Arctic F83 wt/wt % | Arctic F84 wt/wt % | Arctic F85 wt/wt % | Arctic F86 wt/wt % | Arctic F87 wt/wt % | Arctic F88 wt/wt % | Arctic F89 wt/wt % |
|---|---|---|---|---|---|---|---|---|---|---|
| Donepezil | 1.0 | 1.0 | 1.0 | 1.0 | 1.0 | 1.0 | 1.0 | 1.0 | 1.0 | 1.0 |
| Ethanol | 40.0 | 30.0 | 35.0 | 35.0 | 35.0 | 35.0 | 30.0 | 35.0 | 30.0 | 30.0 |
| Propylene glycol | 29.0 | 29.0 | 29.0 | 29.0 | 29.0 | 29.0 | 29.0 | 29.0 | 29.0 | 29.0 |
| Transcutol | 30.0 | 30.0 | 30.0 | 30.0 | 30.0 | 30.0 | 30.0 | 30.0 | 30.0 | 30.0 |
| Isopropyl myristate | | 10.0 | | | | | | | | |
| Methyl Salicylate | | | 5.0 | | | | | | | |
| Methyl Laurate | | | | 5.0 | | | | | | |
| Ethyl Oleate | | | | | 5.0 | | | | | |
| Lauryl lactate | | | | | | 5.0 | | | | |
| Limonene | | | | | | | 10.0 | | | |
| Brij L4 | | | | | | | | 5.0 | | |
| Isopropyl palmitate | | | | | | | | | 10.0 | |
| Hexylene glycol | | | | | | | | | | 10.0 |

Jul. 12, 2017ArctTor Q95

Formulation name

| Ingredient | Arctic 61 wt/wt % | Arctic F90 wt/wt % | Arctic F91 wt/wt % | Arctic F93 wt/wt % | Arctic F94 wt/wt % | Arctic F95 wt/wt % | Arctic F96 wt/wt % | Arctic F97 wt/wt % | Arctic F98 wt/wt % | Arctic F99 wt/wt % |
|---|---|---|---|---|---|---|---|---|---|---|
| Donepezil | 1.0 | 1.0 | 1.0 | 1.0 | 1.0 | 1.0 | 1.0 | 1.0 | 1.0 | 1.0 |
| Ethanol | 40.0 | 35.0 | 35.0 | 35.0 | 35.0 | 35.0 | 35.0 | 35.0 | 35.0 | 35.0 |
| Propylene glycol | 29.0 | 29.0 | 29.0 | 29.0 | 29.0 | 29.0 | 29.0 | 29.0 | 29.0 | 29.0 |
| Transcutol | 30.0 | 30.0 | 30.0 | 30.0 | 30.0 | 30.0 | 30.0 | 30.0 | 30.0 | 30.0 |
| Menthol | | 5.0 | | | | | | | | |
| Lactic acid | | | 5.0 | | | | | | | |
| Urea | | | | 5.0 | | | | | | |
| Ammonium lauryl sulfate | | | | | 5.0 | | | | | |
| Myristyl alcohol | | | | | | 5.0 | | | | |
| Methyl salicylate | | | | | | | 5.0 | | | |
| Oleyl oleate | | | | | | | | 5.0 | | |
| Propylene glycol monolaurate | | | | | | | | | 5.0 | |
| Benzyl alcohol | | | | | | | | | | 5.0 |

TABLE 2D

| All formulations were free flowing solutions. |
| --- |

Jul. 25, 2017ArctFlx Q95

| | Formulation name | | | | | | | | |
| --- | --- | --- | --- | --- | --- | --- | --- | --- | --- |
| Ingredient | Arctic 61 wt/wt % | Arctic F100 wt/wt % | Arctic F101 wt/wt % | Arctic F102 wt/wt % | Arctic F103 wt/wt % | Arctic F104 wt/wt % | Arctic F105 wt/wt % | Arctic F106 wt/wt % | Arctic F107 wt/wt % |
| Donepezil | 1.0 | 1.0 | 1.0 | 1.0 | 1.0 | 1.0 | 1.0 | 1.0 | 1.0 |
| Ethanol | 40.0 | 35.0 | 35.0 | 35.0 | 35.0 | 35.0 | 35.0 | 35.0 | 35.0 |
| Propylene glycol | 29.0 | 29.0 | 29.0 | 29.0 | 29.0 | 29.0 | 29.0 | 29.0 | 29.0 |
| Transcutol | 30.0 | 30.0 | 30.0 | 30.0 | 30.0 | 30.0 | 30.0 | 30.0 | 30.0 |
| Octyldodecanol | | 5.0 | | | | | | | |
| Diethylene glycol | | | 5.0 | | | | | | |
| Caprol 3GO | | | | 5.0 | | | | | |
| Cremphor EL | | | | | 5.0 | | | | |
| Dimethyl sulfone | | | | | | 5.0 | | | |
| Glyceryl ricinoleate | | | | | | | 5.0 | | |
| Disodium lauryl sulfosuccinate | | | | | | | | 5.0 | |
| Ethyl lactate | | | | | | | | | 5.0 |

Aug. 1, 2017ArctFlx Q95

| | Formulation name | | | | | | | | | |
| --- | --- | --- | --- | --- | --- | --- | --- | --- | --- | --- |
| Ingredient | Arctic 61 wt/wt % | Arctic F108 wt/wt % | Arctic F109 wt/wt % | Arctic F110 wt/wt % | Arctic F111 wt/wt % | Arctic F112 wt/wt % | Arctic F113 wt/wt % | Arctic F114 wt/wt % | Arctic F115 wt/wt % | Arctic F116 wt/wt % |
| Donepezil | 1.0 | 1.0 | 1.0 | 1.0 | 1.0 | 1.0 | 1.0 | 1.0 | 1.0 | 1.0 |
| Ethanol | 40.0 | 35.0 | 35.0 | 35.0 | 30.0 | 35.0 | 35.0 | 35.0 | 35.0 | 29.0 |
| Propylene glycol | 29.0 | 29.0 | 29.0 | 29.0 | 29.0 | 29.0 | 29.0 | 29.0 | 29.0 | 20.0 |
| Transcutol | 30.0 | 30.0 | 30.0 | 30.0 | 30.0 | 30.0 | 30.0 | 30.0 | 30.0 | 30.0 |
| Benzyl alcohol | | 5.0 | | | | | | | | |
| Tween 40 | | | 5.0 | | | | | | | |
| Tween 60 | | | | 5.0 | | | | | | |
| Ceraphyl 41 | | | | | 10.0 | | | | | |
| Propylene carbonate | | | | | | 5.0 | | | | |
| Span 20 | | | | | | | 5.0 | | | |
| POLYGLYCERYL-3 OLEATE | | | | | | | | 5.0 | | |
| Isostearyl Alcohol | | | | | | | | | 5.0 | |
| PEG 400 | | | | | | | | | | 20.0 |

Aug. 10, 2017ArctFlx Q95

| | Formulation name | | | | | | |
| --- | --- | --- | --- | --- | --- | --- | --- |
| Ingredient | Arctic 61 wt/wt % | Arctic F83 wt/wt % | Arctic F84 wt/wt % | Arctic F86 wt/wt % | Arctic F88 wt/wt % | Arctic F95 wt/wt % | Arctic F99 wt/wt % |
| Donepezil | 1.0 | 1.0 | 1.0 | 1.0 | 1.0 | 1.0 | 1.0 |
| Ethanol | 40.0 | 35.0 | 35.0 | 30.0 | 35.0 | 37.0 | 38.0 |
| Propylene glycol | 29.0 | 29.0 | 29.0 | 29.0 | 29.0 | 29.0 | 29.0 |
| Transcutol | 30.0 | 30.0 | 30.0 | 30.0 | 30.0 | 30.0 | 30.0 |
| Methyl Laurate | | 5.0 | | | | | |
| Ethyl oleate | | | 5.0 | | | | |
| limonene | | | | 10.0 | | | |
| Isopropyl palmitate | | | | | 5.0 | | |

TABLE 2D-continued

| All formulations were free flowing solutions. |
| --- |

| Myristyl alcohol | 3.0 |
| Benzyl alcohol | 2.0 |

Aug. 21, 2017ArctFlx

Formulation name

| Ingredient | Arctic 61 wt/wt % | Arctic F83 wt/wt % | Arctic F84 wt/wt % | Arctic F88 wt/wt % | Arctic F117 wt/wt % | Arctic F118 wt/wt % | Arctic F119 wt/wt % | Arctic F120 wt/wt % | Arctic F121 wt/wt % | Arctic F122 wt/wt % |
| --- | --- | --- | --- | --- | --- | --- | --- | --- | --- | --- |
| Donepezil | 1.0 | 1.0 | 1.0 | 1.0 | 1.0 | 1.0 | 1.0 | 1.0 | 1.0 | 1.0 |
| Ethanol | 40.0 | 35.0 | 35.0 | 35.0 | 30.0 | 30.0 | 30.0 | 30.0 | 30.0 | 30.0 |
| Propylene glycol | 29.0 | 29.0 | 29.0 | 29.0 | 29.0 | 29.0 | 29.0 | 29.0 | 29.0 | 29.0 |
| Transcutol | 30.0 | 30.0 | 30.0 | 30.0 | 30.0 | 30.0 | 30.0 | 30.0 | 30.0 | 30.0 |
| Methyl Laurate | | 5.0 | | | 5.0 | | | 5.0 | | |
| Ethyl oleate | | | 5.0 | | | 5.0 | | | 5.0 | |
| Isopropyl palmitate | | | | 5.0 | | | 5.0 | | | 5.0 |
| Brij L4 | | | | | 5.0 | 5.0 | 5.0 | | | |
| Brij S20 | | | | | | | | 5.0 | 5.0 | 5.0 |

TABLE 2E

Arctic F61-Arctic F122 are free flowing solutions. Arctic F88G, F131G and F132G are gelled versions of the solution formulation (prepared with the addition of hydroxypropyl cellulose). Arctic F134-F139 are also gelled formulations.

Aug. 24, 2017ArctFlx

Formulation name

| Ingredient | Arctic 61 wt/wt % | Arctic F83 wt/wt % | Arctic F84 wt/wt % | Arctic F88 wt/wt % | Arctic F123 wt/wt % | Arctic F124 wt/wt % | Arctic F125 wt/wt % | Arctic F126 wt/wt % | Arctic F127 wt/wt % | Arctic F128 wt/wt % |
| --- | --- | --- | --- | --- | --- | --- | --- | --- | --- | --- |
| Donepezil | 1.0 | 1.0 | 1.0 | 1.0 | 1.0 | 1.0 | 1.0 | 1.0 | 1.0 | 1.0 |
| Ethanol | 40.0 | 35.0 | 35.0 | 35.0 | 31.0 | 31.0 | 31.0 | 30.0 | 30.0 | 30.0 |
| Propylene glycol | 29.0 | 29.0 | 29.0 | 29.0 | 29.0 | 29.0 | 29.0 | 29.0 | 29.0 | 29.0 |
| Transcutol | 30.0 | 30.0 | 30.0 | 30.0 | 30.0 | 30.0 | 30.0 | 30.0 | 30.0 | 30.0 |
| Methyl Laurate | | 5.0 | | | 5.0 | | | 5.0 | | 5.0 |
| Ethyl oleate | | | 5.0 | | | 5.0 | | 5.0 | 5.0 | |
| Isopropyl palmitate | | | | 5.0 | | | 5.0 | | 5.0 | 5.0 |
| Cocamide DEA | | | | | 4.0 | 4.0 | 4.0 | | | |

Aug. 30, 2017ArctFlx Q95

Formulation name

| Ingredient | Arctic F88 wt/wt % | Arctic F129 wt/wt % | Arctic F130 wt/wt % | Arctic F131 wt/wt % | Arctic F132 wt/wt % | Arctic F133 wt/wt % |
| --- | --- | --- | --- | --- | --- | --- |
| Donepezil | 1.0 | 1.0 | 1.0 | 1.0 | 1.0 | 1.0 |
| Ethanol | 35.0 | 30.0 | 30.0 | 32.0 | 30.0 | 30.0 |
| Propylene glycol | 29.0 | 29.0 | 29.0 | 29.0 | 29.0 | 29.0 |
| Transcutol | 30.0 | 30.0 | 30.0 | 30.0 | 30.0 | 30.0 |
| Isopropyl palmitate | 5.0 | 5.0 | 5.0 | 5.0 | 5.0 | 5.0 |
| Isopropyl myristate | | 5.0 | | | | |

TABLE 2E-continued

Arctic F61-Arctic F122 are free flowing solutions. Arctic F88G, F131G and F132G are gelled versions of the solution formulation (prepared with the addition of hydroxypropyl cellulose). Arctic F134-F139 are also gelled formulations.

| | | | | | |
|---|---|---|---|---|---|
| Diisopropyl adipate | | 5.0 | | | |
| Lauryl lactate | | | 3.0 | | |
| Cetyl alcohol | | | | 5.0 | |
| Limonene | | | | | 5.0 |

Sep. 7, 2017ArctTor

| | Formulation name | | | | | |
|---|---|---|---|---|---|---|
| Ingredient | Arctic F88 wt/wt % | Arctic F88G wt/wt % | Arctic F131 wt/wt % | Arctic F131G wt/wt % | Arctic F132 wt/wt % | Arctic F132G wt/wt % |
| Donepezil | 1.0 | 1.0 | 1.0 | 1.0 | 1.0 | 1.0 |
| Ethanol | 35.0 | 33.0 | 32.0 | 30.0 | 30.0 | 28.0 |
| Propylene glycol | 29.0 | 29.0 | 29.0 | 29.0 | 29.0 | 29.0 |
| Transcutol | 30.0 | 30.0 | 30.0 | 30.0 | 30.0 | 30.0 |
| Isopropyl palmitate | 5.0 | 5.0 | 5.0 | 5.0 | 5.0 | 5.0 |
| Lauryl lactate | | | 3.0 | 3.0 | | |
| Cetyl alcohol | | | | | 5.0 | 5.0 |
| HY119 | | 2.0 | | 2.0 | | 2.0 |

Sep. 21, 2017ArctTor Q95

| | Formulation name | | | | | |
|---|---|---|---|---|---|---|
| Ingredient | Arctic F88 wt/wt % | Arctic F134 wt/wt % | Arctic F136 wt/wt % | Arctic F137 wt/wt % | Arctic F138 wt/wt % | Arctic F139 wt/wt % |
| Donepezil | 1.0 | 0.3 | 1.0 | 1.0 | | 1.0 |
| Donepezil HCL | | | | | 1.0 | 1.0 |
| Ethanol | 34.0 | 32.8 | 32.0 | 30.5 | 32.0 | 32.0 |
| Propylene glycol | 28.2 | 29.0 | 29.0 | 27.6 | 29.0 | 29.0 |
| Transcutol | 29.1 | 30.0 | 10.0 | 9.5 | 30.0 | 10.0 |
| Isopropyl palmitate | 4.9 | 5.0 | | 4.8 | 5.0 | |
| HPC | 2.9 | 3.0 | 3.0 | 2.9 | 3.0 | 3.0 |
| Diisopropyl adipate | | | 5.0 | | | 5.0 |
| Water | | | 20.0 | | | 20.0 |
| GTCC | | | | 19.0 | | |
| Brij L4 | | | | 4.8 | | |

TABLE 2F

Arctic F140-F150 consisted of gels (F140-143 and F146-F148) and creams (F144, F145, F149 and F150). HPMC = hydroxypropyl methyl cellulose (Methocel E4M), PVP 40 = polyvinylpyrrolidone 40 (Povidone 5 40), and HY119 = hydroxypropyl cellulose (Spectrum HY119).

Sep. 28, 2017ArcFlx Q95

| | Formulation name | | | | | | |
|---|---|---|---|---|---|---|---|
| Ingredient | Control wt/wt % | Arctic F140 wt/wt % | Arctic F141 wt/wt % | Arctic F142 wt/wt % | Arctic F143 wt/wt % | Arctic F144 wt/wt % | Arctic F145 wt/wt % |
| Donepezil | | 1.0 | 1.0 | | | 1.0 | |
| Donepezil HCL | 1.0 | | | 1.0 | 1.0 | | 1.0 |
| HPMC | 3.0 | | | | | | |
| PVP 40 | 1.0 | | | | | | |
| Water | 95.0 | | | | | | |
| Ethanol | | 30.0 | 14.0 | 30.0 | 14.0 | | |
| PEG 400 | | 31.0 | 40.0 | 31.0 | 40.0 | | |

TABLE 2F-continued

Arctic F140-F150 consisted of gels (F140-143 and F146-F148) and creams (F144, F145, F149 and F150). HPMC = hydroxypropyl methyl cellulose (Methocel E4M), PVP 40 = polyvinylpyrrolidone 40 (Povidone 5 40), and HY119 = hydroxypropyl cellulose (Spectrum HY119).

| Ingredient | | | | | | |
|---|---|---|---|---|---|
| PEG 1450 | 10.0 | 30.0 | 10.0 | 30.0 | | |
| Transcutol | 20.0 | 10.0 | 20.0 | 10.0 | | |
| Isopropyl palmitate | 5.0 | 5.0 | 5.0 | 5.0 | | |
| HY119 | 3.0 | | 3.0 | | | |
| Cetyl alcohol | | | | | 8.0 | 8.0 |
| Isopropyl myristate | | | | | 5.0 | 5.0 |
| GTCC | | | | | 7.0 | 7.0 |
| Isopropyl palmitate | | | | | 7.0 | 7.0 |
| Transcutol | | | | | 7.0 | 7.0 |
| Propylene glycol | | | | | 7.0 | 7.0 |
| Brij L4 | | | | | 3.0 | 3.0 |
| Tween 80 | | | | | 3.0 | 3.0 |
| Water | | | | | 51.8 | 51.8 |
| Xanthum gum | | | | | 0.3 | 0.3 |

Oct. 12, 2017ArcFlx Q95

| | | Formulation name | | | | |
|---|---|---|---|---|---|---|
| Ingredient | Control wt/wt % | Arctic F146 wt/wt % | Arctic F147 wt/wt % | Arctic F148 wt/wt % | Arctic F149 wt/wt % | Arctic F150 wt/wt % |
| Donepezil | | 1.0 | 1.0 | 1.0 | | |
| Donepezil HCL | 1.0 | | | | 1.0 | 1.0 |
| HPMC | 3.0 | | | | | |
| PVP 40 | 1.0 | | | | | |
| Water | 95.0 | | | | 40.0 | 30.0 |
| Ethanol | | 36.0 | 36.0 | 31.0 | | |
| Propylene glycol | | | 11.0 | | 7.0 | 7.0 |
| PEG 400 | | 31.0 | 20.0 | 20.0 | | |
| PEG 1450 | | 5.0 | 5.0 | | | |
| PEG 600 | | | | 10.0 | | |
| Transcutol | | 20.0 | 20.0 | 30.0 | 7.0 | 7.0 |
| Isopropyl palmitate | | 5.0 | 5.0 | 5.0 | 7.0 | 7.0 |
| HY119 | | 2.0 | 2.0 | 3.0 | 0.5 | 0.5 |
| Cetyl alcohol | | | | | 10.0 | 12.0 |
| Isopropyl myristate | | | | | 10.0 | 15.0 |
| GTCC | | | | | 10.0 | 13.0 |
| Brij L4 | | | | | 3.8 | 3.8 |
| Tween 80 | | | | | 3.8 | 3.8 |

TABLE 2G

Arctic F151-F161 consist of gels (F151-F161) and creams (F162). HPMC = hydroxypropyl methyl cellulose (Methocel E4M), PVP 40 = polyvinylpyrrolidone 40 (Povidone 40), and HY119 = hydroxypropyl 5 cellulose (Spectrum HY119).

Oct. 23, 2017ArctFlx Q95

| | | Formulation name | | | | |
|---|---|---|---|---|---|---|
| Ingredient | Control wt/wt % | Arctic F140 wt/wt % | Arctic F151 wt/wt % | Arctic F152 wt/wt % | Arctic F153 wt/wt % | Arctic F154 wt/wt % |
| HPMC | 3.0 | | | | | |
| PVP 40 | 1.0 | | | | | |
| Donepezil HCL | 1.0 | | | | | |
| Water | 95.0 | | | | | |
| Donepezil | | 1.0 | 1.0 | 1.0 | 1.0 | 1.0 |
| Ethanol | | 30.0 | 40.0 | 30.0 | 30.0 | 40.0 |
| PEG 400 | | 31.0 | 21.0 | 26.0 | 21.0 | 26.0 |
| PEG 1450 | | 10.0 | 10.0 | 5.0 | 10.0 | 5.0 |
| Transcutol | | 20.0 | 20.0 | 30.0 | 30.0 | 20.0 |
| Isopropyl palmitate | | 5.0 | 5.0 | 5.0 | 5.0 | 5.0 |
| HY119 | | 3.0 | 3.0 | 3.0 | 3.0 | 3.0 |

TABLE 2G-continued

Arctic F151-F161 consist of gels (F151-F161) and creams (F162).
HPMC = hydroxypropyl methyl cellulose (Methocel E4M),
PVP 40 = polyvinylpyrrolidone 40 (Povidone 40), and
HY119 = hydroxypropyl 5 cellulose (Spectrum HY119).

Oct. 31, 2017ArctFlx Q95

| | Formulation name | | | | | |
|---|---|---|---|---|---|---|
| Ingredient | Arctic F154 wt/wt % | Arctic F155 wt/wt % | Arctic F156 wt/wt % | Arctic F157 wt/wt % | Arctic F158 wt/wt % | Arctic F159 wt/wt % |
| Donepezil | 1.0 | 1.0 | 1.0 | 1.0 | 1.0 | 1.0 |
| Ethanol | 40.0 | 40.0 | 35.0 | 30.0 | 37.5 | 40.0 |
| PEG 400 | 26.0 | 16.0 | 16.0 | 16.0 | 11.0 | 26.0 |
| PEG 1450 | 5.0 | 5.0 | 5.0 | 5.0 | 5.0 | |
| Transcutol | 20.0 | 30.0 | 35.0 | 40.0 | 37.5 | 25.0 |
| Isopropyl palmitate | 5.0 | 5.0 | 5.0 | 5.0 | 5.0 | 5.0 |
| HY119 | 3.0 | 3.0 | 3.0 | 3.0 | 3.0 | 3.0 |

Nov. 13, 2017ArctFlx Q95

| | | Formulation name | | | | |
|---|---|---|---|---|---|---|
| | Control | Arctic F154 | Arctic F155 | Arctic F160 | Arctic F161 | Arctic F162 |
| Specific gravity | 1 | 1 | 1 | 1 | 1 | 1 |
| Dosing (ul): | 10 | 10 | 10 | 10 | 10 | 10 |
| wt % Donepezil | 1.0 | 1.0 | 1.0 | 1.0 | 1.0 | 1.0 |
| Ingredient | wt/wt % | wt/wt % | wt/wt % | wt/wt % | wt/wt % | wt/wt % |
| Donepezil HCL | 1.0 | | | | | 1.0 |
| Donepezil | | 1.0 | 1.0 | 1.0 | 1.0 | |
| PVP 40 | 1.0 | | | | | |
| HPMC | 3.0 | | | | | |
| Water | 95.0 | | | | | 40.3 |
| Ethanol | | 40.0 | 40.0 | 40.0 | 40.0 | |
| PEG 400 | | 26.0 | 16.0 | 26.0 | 16.0 | |
| PEG 1450 | | 5.0 | 5.0 | | | |
| PEG 600 | | | | 5.0 | 5.0 | |
| Transcutol | | 20.0 | 30.0 | 20.0 | 30.0 | |
| Isopropyl palmitate | | 5.0 | 5.0 | 5.0 | 5.0 | |
| HY119 | | 3.0 | 3.0 | 3.0 | 3.0 | |
| Cetyl alcohol | | | | | | 10.0 |
| Isopropyl myristate | | | | | | 10.0 |
| Capric/Caprylic Triglyceride | | | | | | 10.0 |
| Isopropyl palmitate | | | | | | 7.0 |
| Transcutol | | | | | | 7.0 |
| Propylene glycol | | | | | | 7.0 |
| Brij L4 | | | | | | 4.4 |
| Tween 80 | | | | | | 3.1 |
| Xanthum gum | | | | | | 0.2 |

TABLE 2H

Formulations Arct162A, 164A, 164B, and 164C compositions
Feb2118ArcFlx

| Formulation name | Arct162 A | Arct164 A | Arct164 B | Arct164 C |
|---|---|---|---|---|
| Specific gravity | 1.0 | 1.0 | 1.0 | 1.0 |
| Dosing (ul): | 10.0 | 10.0 | 10.0 | 10.0 |
| wt % Donepezil | 1.0 | 1.0 | 1.0 | 1.0 |
| Ingredient | wt/wt % | wt/wt % | wt/wt % | wt/wt % |

TABLE 2H-continued

Formulations Arct162A, 164A, 164B, and 164C compositions
Feb2118ArcFlx

| Formulation name | Arct162 A | Arct164 A | Arct164 B | Arct164 C |
|---|---|---|---|---|
| Cetyl alcohol | 10.0 | 5.0 | 3.0 | 5.1 |
| Isopropyl myristate | 10.0 | | | |
| Capric/Caprylic triglycerides GTCC | 10.0 | 5.0 | 5.0 | |
| Isopropyl palmitate | 7.0 | 7.0 | 7.0 | 7.1 |
| White Wax | | 7.0 | 5.0 | 5.1 |
| Donepezil HCL | 1.0 | 1.0 | 1.0 | 1.0 |
| Transcutol | 7.0 | 7.0 | 7.0 | 7.1 |
| Propylene glycol | 7.0 | 7.0 | 7.0 | 7.1 |
| Brij L4 | 4.4 | | | |
| Tween 80 | 3.1 | | | |
| Water | 40.3 | 55.5 | 59.5 | 56.6 |
| Xanthum gum | 0.2 | | | |
| Span 20 | | 2.9 | 3.0 | 2.9 |
| Tween 20 | | 2.1 | 2.0 | 2.3 |
| HPMC | | 0.5 | 0.5 | 0.5 |
| Mineral oil | | | | 5.2 |

TABLE 2I

Formulations Arct165 composition

| Ingredients | wt % | Arctic F165 Function |
|---|---|---|
| Donepezil HCl | 1 | Active |
| Transcutol | 7 | Penetration enhancer |
| Propylene glycol | 7 | Cosolvent |
| Cetyl alcohol | 3 | Oil phase |
| Capric/Caprylic triglycerides GTCC | 5 | Oil phase |
| Isopropyl palmitate | 7 | Penetration enhancer |
| Bee wax | 5 | Thickener |
| Span 20 | 4.9 | Emulsifier |
| Tween 20 | 3.3 | Emulsifier |
| Water | 56.9 | Water phase |

Example 3: General Procedure for Porcine Skin Permeation Screening Measurement in an Array Format A block comprising 24 or 48 miniature diffusion cells arranged in a matrix format, as taught by U.S. Pat. No. 8,277,762, is used for initial screening of skin permeation and retention. A single contiguous piece of porcine skin, trimmed to a uniform thickness of 1.2 mm is introduced between two 48-well plates (porcine skin is more readily available in the sizes required and is less costly than human skin. Porcine skin is generally slightly less permeable than human skin, but permeation results with porcine skin are usually predictive of human skin performance).

Each formulation composition is applied, typically at a pseudo-finite dose of 20 µL, to an addressed skin area of 0.30 cm² in 6-fold replicates across the donor wells in a suitable set of 24- or 48-well diffusion cell plates.

Phosphate-buffered saline solution at pH 7.4 ("PBS") containing 0.01% 0.01% sodium azide (a preservative) is used for the receptor well fluid, this fluid having been verified as providing sink conditions for donepezil through-out the experiments. The receptor well plate is maintained at 32 (±0.5)° C. during the experiments and each receptor well is stirred and agitated using a magnetic stirrer bar. At the 24h mark, each addressed skin area is washed and then dried with a Q-tip. The 24- or 48-well plate is disassembled, each receptor well sampled, and the extent of retention of donepezil in the skin assessed by extraction into DMSO, followed by analysis using the verified high-performance liquid chromatography ("HPLC") method with ultraviolet ("UV") detection at 270 nm.

This screening method using porcine skin was utilized to test for permeation of formulation represented in Table 2A through Table 2E Aug2417ArctFlx table.

Example 4: General Procedure for Human and Porcine Skin Permeation Measurements Using Vertical Diffusion Cells Franz diffusion cell experiments were used to analyze flux rates of donepezil from compositions taught under the present invention across human skin. Franz diffusion cells are a common and well known method for measuring transdermal flux rates. The general Franz cell procedure is described by Franz {Franz, 1975 #108}.

In the examples described herein, Franz diffusion cells ("FDC"s) with a 3.3 mL receptor well volume were used, with either porcine skin or human cadaver skin.

For porcine skin, by-product dorsal skin from approximately 10-week old female Yorkshire pigs (sacrificed for purposes unrelated to this permeation study) was supplied by Thomas D Morris (Reistertown, MD). The porcine skin arrived on dry ice and was maintained at –20° C. until the morning of the study. On the day of the study, the porcine skin was removed from the freezer and allowed to thaw to room temperature on the benchtop. The porcine skin was then dermatomed to a set thickness of ~1 mm using a skin skiving system.

For human cadaver skin, split thickness human cadaver skin (0.015"-0.018") was obtained from AlloSource (Centennial, CO) or Skin Bank New York Firefighters (New York, NY). The skin tissue was dermatomed by the tissue bank to a thickness of some 250 µm and shipped frozen on dry ice. All information available from the cadaver skin supplier pertaining to the source of the tissue, donor information, the part of the body, the condition of the tissue, and the duration of storage prior to receipt were maintained in study files Upon receipt of the donor skin, the skin pieces were stored at –20° C. until used. Prior to use, the skin pieces were removed from the freezer and allowed to thaw fully at ambient temperature.

The donor well addresses a skin area of about 0.55 cm². The receptor wells were filled with PBS containing 0.01% sodium azide (a preservative) (the "Receptor Fluid"), this fluid having been verified as providing sink conditions for donepezil throughout the experiments. The receptor wells of the FDCs were maintained at 37° C. (the temperature on the surface of the skin is 32 (±0.5° C.)) in a stirring dry block with continual agitation of the Receptor Fluid in the receptor well using a magnetic stir bar. Donor and receptor chambers were clamped about the skin piece under uniform pressure using a pinch clamp (SS #18 VWR 80073-350).

After the FDCs were assembled, the skin was allowed to hydrate for 20 minutes in contact with the receptor fluid. Any FDCs that evidenced any leakage during this period were discarded.

The integrity and quality of each skin piece was tested prior to application of the test formulations through measurement of the transdermal flux of tritiated water or of the transepidermal electrical resistance ("TEER") (skin integrity was usually not tested on porcine skin pieces). The TEER measurements were performed as follows. An aliquot of 150 µl of PBS was introduced into each FDC donor well. After 10 minutes, a blunt electrode probe is placed into the donor well to rests lightly on the surface of the skin under its own weight. A second electrode is then inserted into receptor fluid via the sample port on the receptor chamber of the FDC. An alternating current ("AC") signal, 100 mV root mean square ("RMS") at 100 Hz, is applied across the skin using a waveform generator and the impedance is then measured with a digital multimeter and the results recorded in kΩ. Any FDC showing anomalously low impedance (nominally <2 kΩ) was discarded and the FDCs were ranked according to the magnitudes of the measured impedance readings. Test articles were then assigned to the batch of FDCs such that the replicates for each test article are each applied to a skin piece with nearly equivalent average transepidermal electrical resistance values.

After the membrane integrity tests were complete and the cells appropriately sorted, samples of the test articles were then applied to the stratum corneum of the skin. A one-time dosing regimen was used for the studies. Six replicates of each of the test formulations are examined, typically in a batch of some 36 FDCs in total.

Doses were applied using a Nichiryo positive displacement pipettor. The doses were dispensed from the pipettor to the skin and spread across the surface using the blunt end of a glass rod. The typical aspirated dose was 10 µL of the formulation per cell for most experiments. The formulations themselves were typically made at 1 wt %. Assuming a 10 µL dose applied to the skin, no loss to the glass rod when spreading the formulation, 1 wt % of the active in the formulation, a specific gravity of 1.0 for the formulation and a surface area of 0.55 cm² per cell, then each FDCs was dosed at ~181.8 µg/cm² of donepezil.

A sample was abstracted from each receptor well at preset times, typically 24 h. Using a graduated Hamilton type injector syringe, a 300 µl aliquot was abstracted from the sampling port of each FDC at 24 hours. Each abstracted aliquot was introduced into a well in a 96-well microtiter plate. Samples were stored in a refrigerator at 4-8° C. prior to HPLC analysis. Samples were analyzed within 5 days of collection.

At 24 hours, the skin was then tape stripped three times with cellophane tape, each tapestripping consisting of applying a piece of cellophane tape to the skin with light pressure and peeling off the tape, thereby systematically removing the upper most layers of the stratum corneum. The tape strips were discarded.

After tape tripping was complete, the remaining skin was split into epidermal and dermal compartments by using a pair of spatulas. If necessary, the skin was placed on a hot plate set at 60° C. for one minute to help facilitate the separation of the skin. The epidermal and dermal compartments were then separately placed into glass vials, into which 3 mL of DMSO was added. The skin pieces were then incubated at 40° C. for 24 hours with gentle agitation. After the 24 hour incubation period, samples were collected.

The samples abstracted from receptor wells and skin extractions were then analyzed by the verified HPLC method using Chemstation software. The AUCs of the donepezil were recorded and converted to µg/mL values using a calibration curve developed from the calibration standards' AUC values and known concentration values. These ug/mL values were imported into the study results Excel workbook. These concentrations were then multiplied by the receptor volume (3.3 mL), or skin extraction volume (3 mL) and divided by the surface area of the skin exposed to the receptor fluid (0.55 cm²) for an end cumulative amount in µg/cm². The concentrations of the Active were assayed and reported in each case.

This screening method using human cadaver skin was utilized to test for permeation of formulations represented in Table 2E Aug3017ArctFlx Q95 through Table 2H.

Material and Reagents

The following materials and reagents were used for the study.

TABLE 3

Materials used.

| # | Ingredient | Supplier |
|---|---|---|
| 1 | Ammonium lauryl sulfate | Aldrich |
| 2 | Benzyl alcohol | Spectrum |
| 3 | Brij L23 | Croda |
| 4 | Brij L4 | Croda |
| 5 | Brij S20 | Croda |
| 6 | Capmul GMO | Abitec |
| 7 | Capric Triglyceride | Spectrum |
| 8 | Caprol 3GO | Abitec |
| 9 | Castor oil | Spectrum |
| 10 | Ceraphyl 41 | ISP |
| 11 | Cetyl alcohol | Spectrum |
| 12 | Cocamide DEA | Spectrum |
| 13 | Cremephor EL | BASF |
| 14 | Crodamol GTCC | Croda |
| 15 | Diethyl sebacate | Aldrich |
| 16 | Diethylene glycol | Alfa Aesar |
| 17 | Diisopropyl adipate | spectrum |
| 18 | Dimethyl isosorbide | Croda |
| 19 | Dimethyl sulfone | Fluka |
| 20 | Dimethyl sulfoxide | Sigma |
| 21 | Dipropylene glycol | Sigma |
| 22 | Disodium lauryl sulfosuccinate | Mcintire |
| 23 | Donepezil | Arctic |
| 24 | Donepezil HCl | Arctic |
| 25 | Ethanol | Sigma Aldrich |
| 26 | Ethyl lactate | Sigma |
| 27 | Ethyl oleate | Spectrum |
| 28 | Glycerin | Sigma |
| 29 | Glyceryl ricinoleate | Phoenix |
| 30 | Hexylene glycol | Spectrum |
| 31 | HPMC | Methocel |
| 32 | HY119 | Spectrum |
| 33 | IPA | VWR |
| 34 | Isopropyl myristate | Spectrum |
| 35 | Isopropyl palmitate | Spectrum |
| 36 | Isostearyl alcohol | Croda |
| 37 | Lactic acid | Spectrum |
| 38 | Lauric diethanolamide | Sigma |
| 39 | Lauryl lactate | Lubrizol |
| 40 | Levulinic acid | Penta Manufacturing |
| 41 | Limonene | Sigma |
| 42 | Menthol | Spectrum |
| 43 | Methyl laurate | TCI |
| 44 | Methyl salicylate | Spectrum |
| 45 | Mineral oil | Sigma |
| 46 | Myristyl alcohol | Sigma |
| 47 | Octyldodecanol | Spectrum |
| 48 | Oleic acid | Sigma |
| 49 | Oleyl alcohol | Pfizer |
| 50 | Oleyl oleate | Alzo |
| 51 | PEG 1450 | Spectrum |
| 52 | PEG 300 | Spectrum |
| 53 | PEG 400 | Spectrum |
| 54 | PEG 600 | Emerald BioSystems |
| 55 | PEG-7 methyl ether | Sigma |
| 56 | Polyglyceryl-3 Oleate | Abitec |
| 57 | Propylene carbonate | JT Baker |
| 58 | Propylene glycol | Sigma |
| 59 | Propylene glycol monolaurate | MP Bio |
| 60 | PVP 40 | ISP |
| 61 | Span 20 | Sigma |
| 62 | Transcutol P | Gattefosse |

TABLE 3-continued

Materials used.

| # | Ingredient | Supplier |
|---|---|---|
| 63 | Tween 40 | Spectrum |
| 64 | Tween 60 | Spectrum |
| 65 | Tween 80 | Fluka |
| 66 | Urea | JT Baker |
| 67 | Water | Distilled |

Results

Several conclusions were made from the first rounds of screening shown in FIGS. 1-6.

Figure 1:
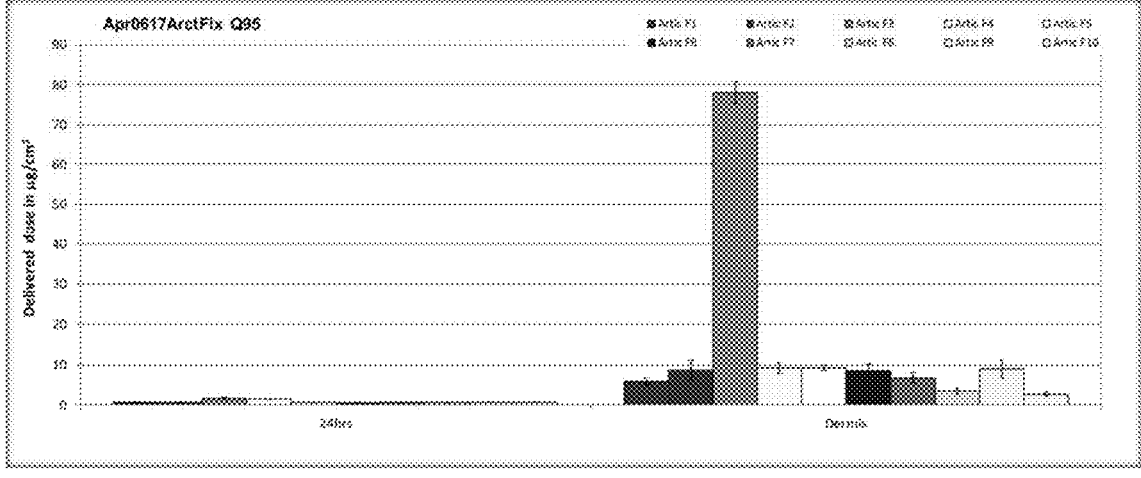
FIG. 1 shows bar graphs that represent data obtained from screening in pure solvent mixtures at 1 wt %. Pure DMSO (Arctic F3) delivered the highest amount of active.
Figure 2:
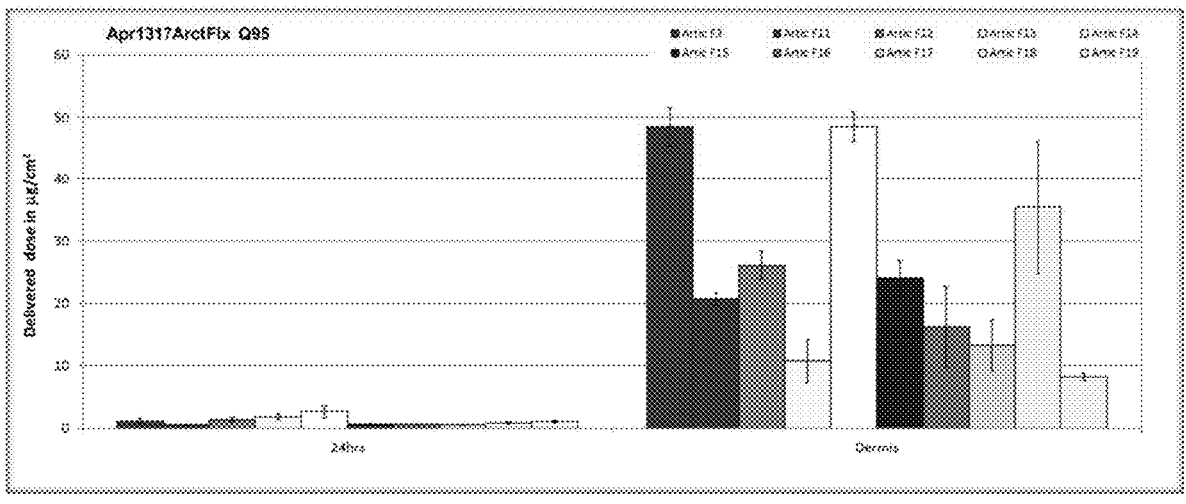
FIG. 2 shows bar graphs that represent data obtained from screening in DMSO+other solvents.
Figure 3:
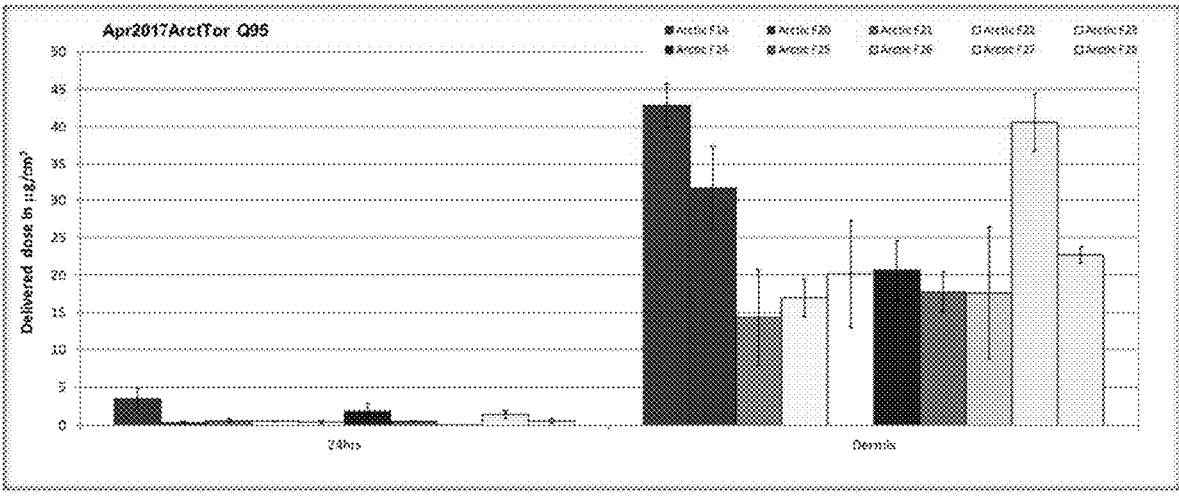
FIG. 3 shows bar graphs that represent data obtained from screening in DMSO+other solvents and other solvent mixtures.
Figure 4:
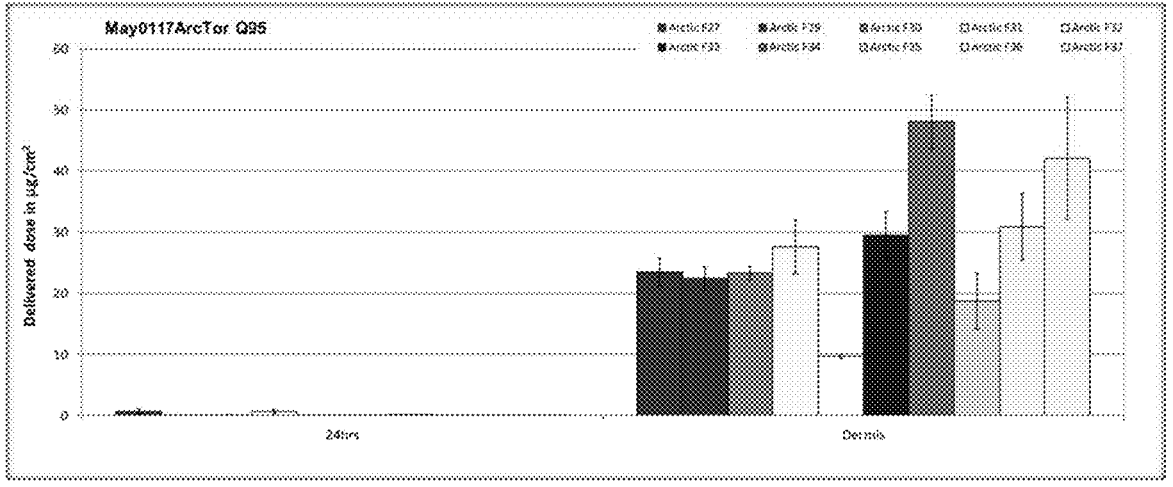
FIG. 4 shows bar graphs that represent data obtained from screening in DMSO+multiple solvents and other solvent mixtures.
Figure 5:
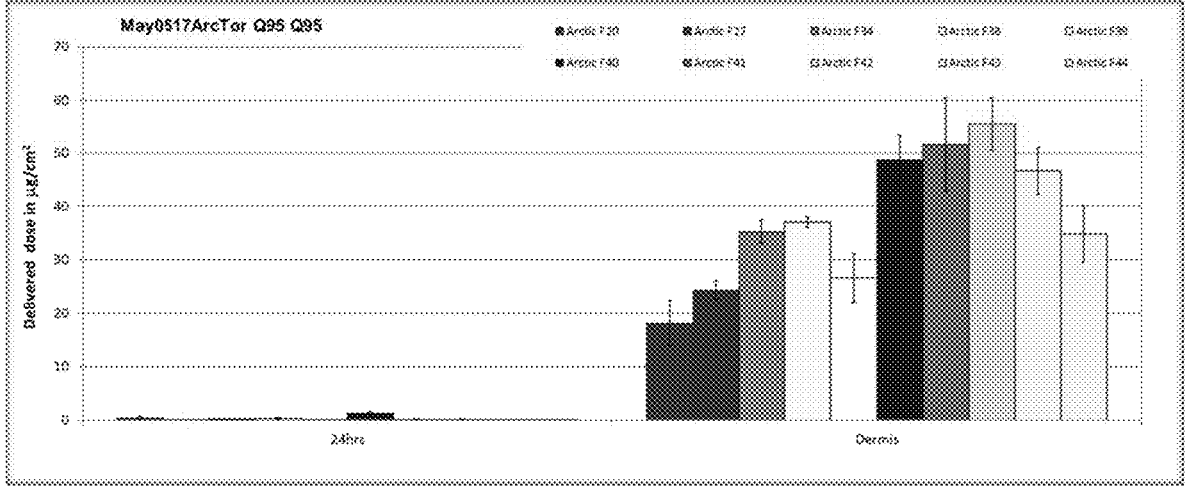
FIG. 5 shows bar graphs that represent data obtained from screening Donepezil HCl and donepezil base in similar solvent chassis.
Figure 6:
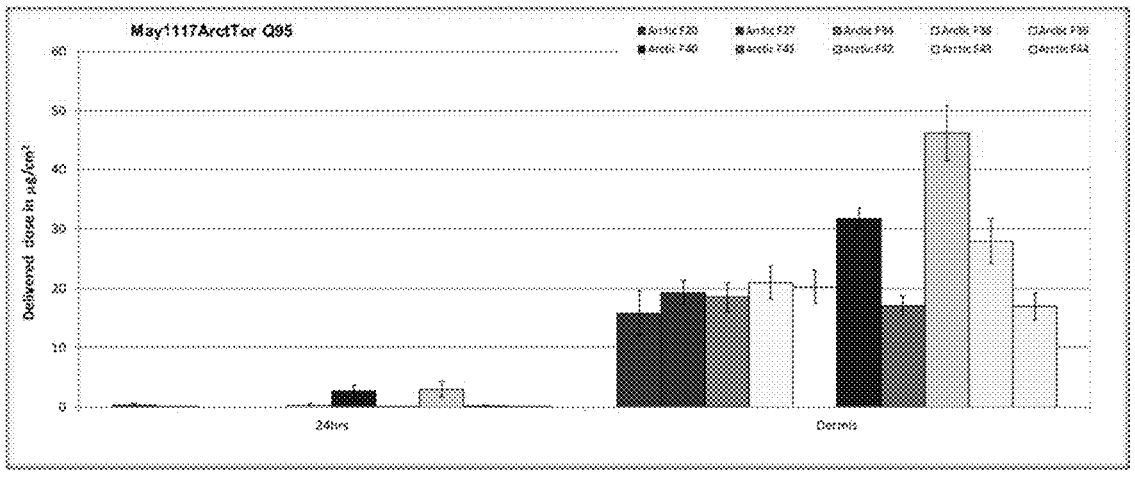
FIG. 6 shows bar graphs that represent data obtained from screening Donepezil HCl and donepezil base in similar solvent chassis.
Figure 7:
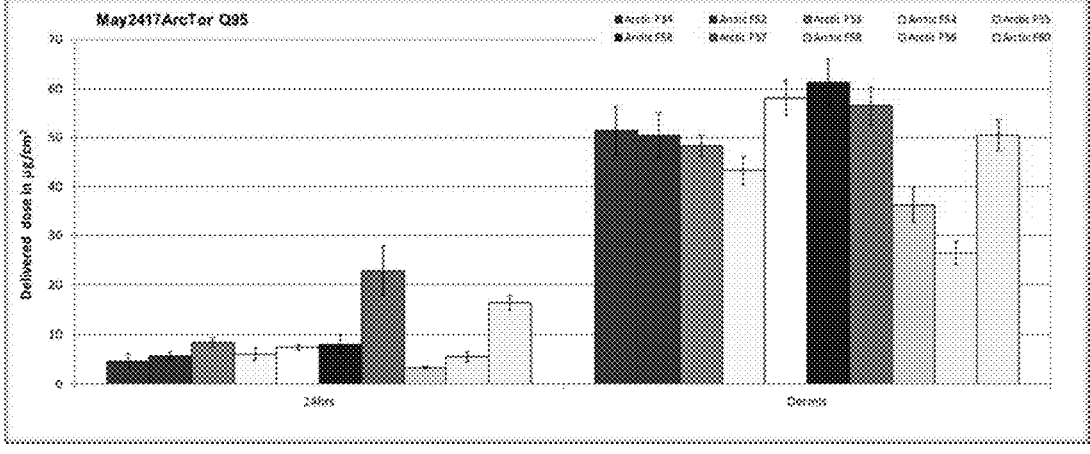
FIG. 7 shows bar graphs that represent data obtained from screening Donepezil base in an ethanol/propylene glycol chassis.
Figure 8:
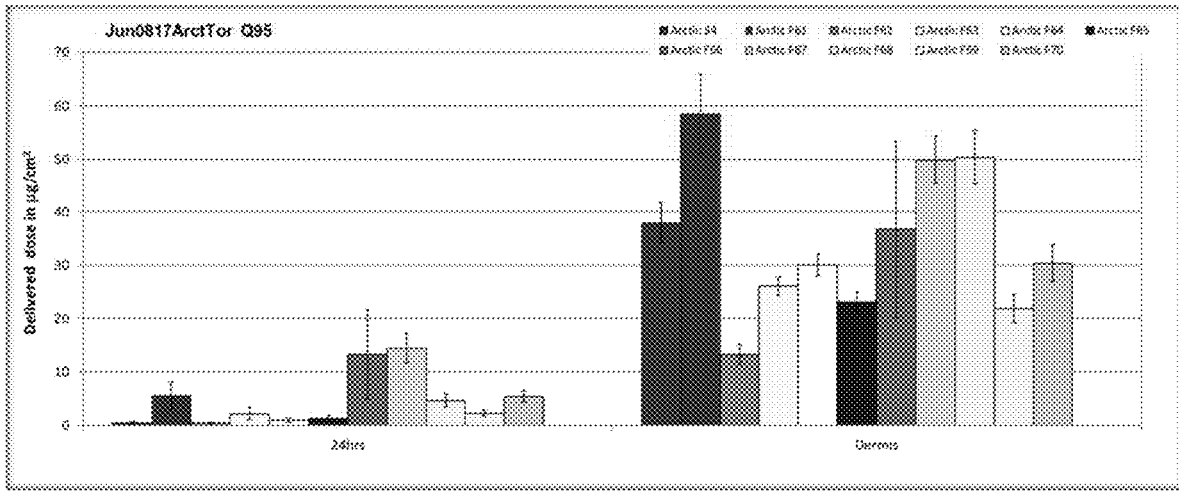
FIG. 8 shows bar graphs that represent data obtained from screening Donepezil base in an ethanol/propylene glycol chassis.
Figure 9:
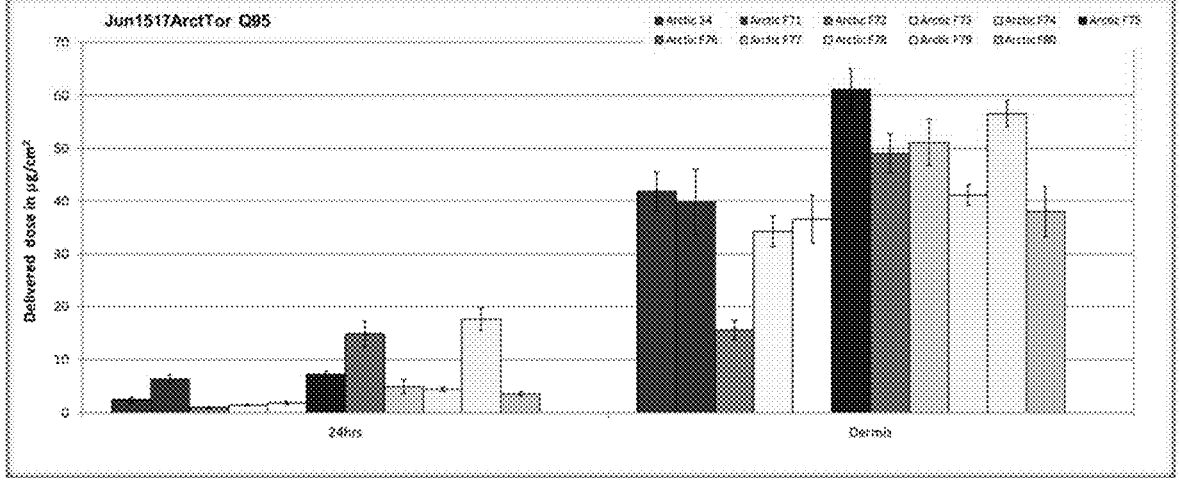
FIG. 9 shows bar graphs that represent data obtained from screening Donepezil base in an ethanol/propylene glycol chassis.
Figure 10:
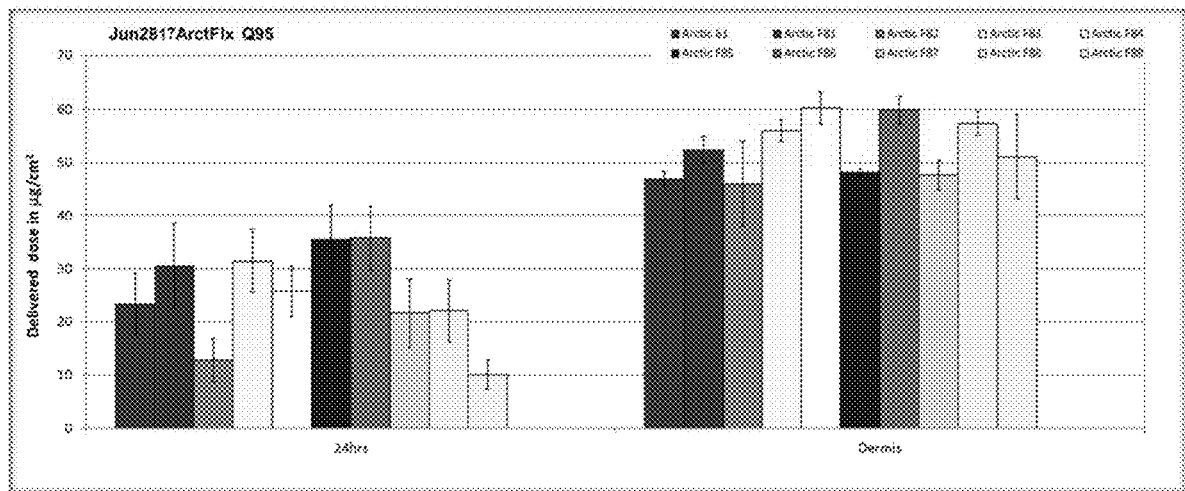
FIG. 10 shows bar graphs that represent data obtained from screening Donepezil base in an ethanol/propylene glycol/Transcutol chassis.
Figure 11:
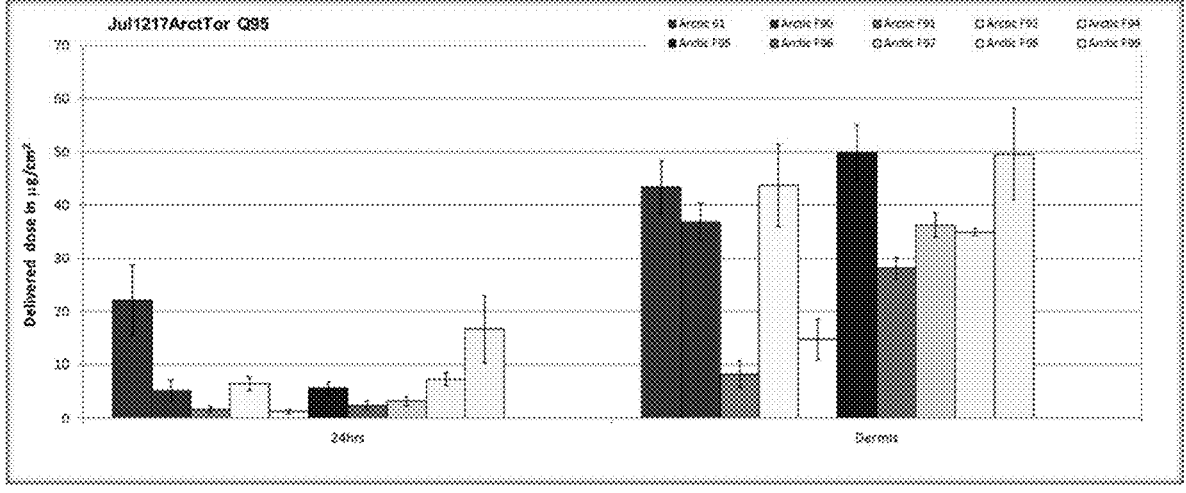
FIG. 11 shows bar graphs that represent data obtained from screening Donepezil base in an ethanol/propylene glycol/Transcutol chassis.
Figure 12:
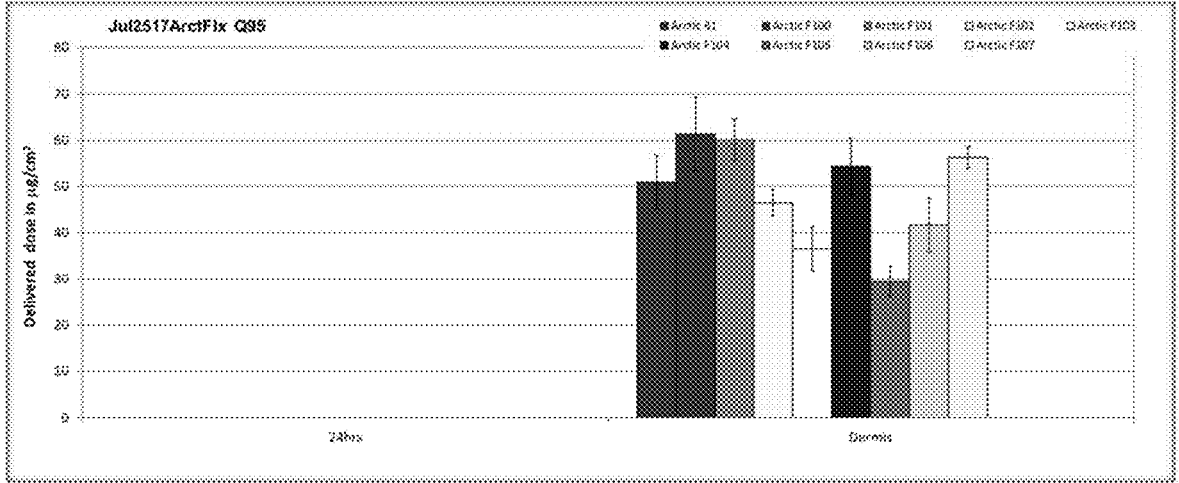
FIG. 12 shows bar graphs that represent data obtained from screening Donepezil base in an ethanol/propylene glycol/Transcutol chassis.
Figure 13:
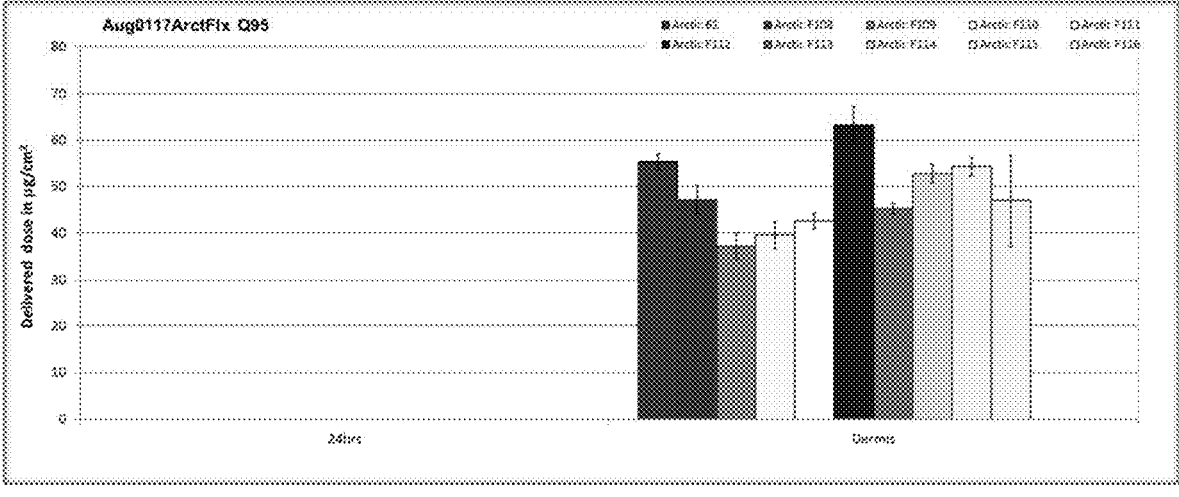
FIG. 13 shows bar graphs that represent data obtained from screening Donepezil base in an ethanol/propylene glycol/Transcutol chassis.
Figure 14:
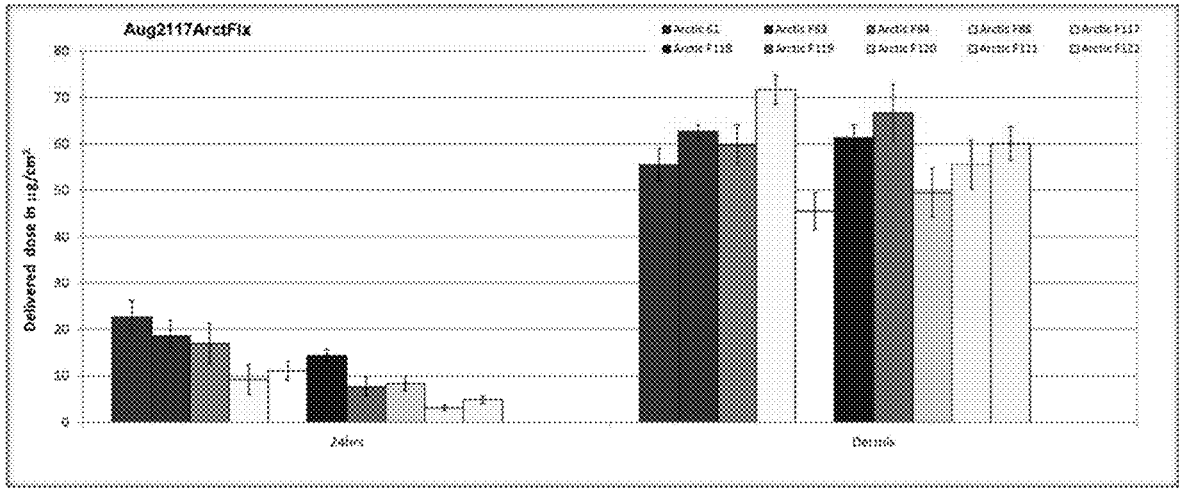
FIG. 14 shows bar graphs that represent data obtained from screening Donepezil base in an ethanol/propylene glycol/Transcutol chassis.
Figure 15:
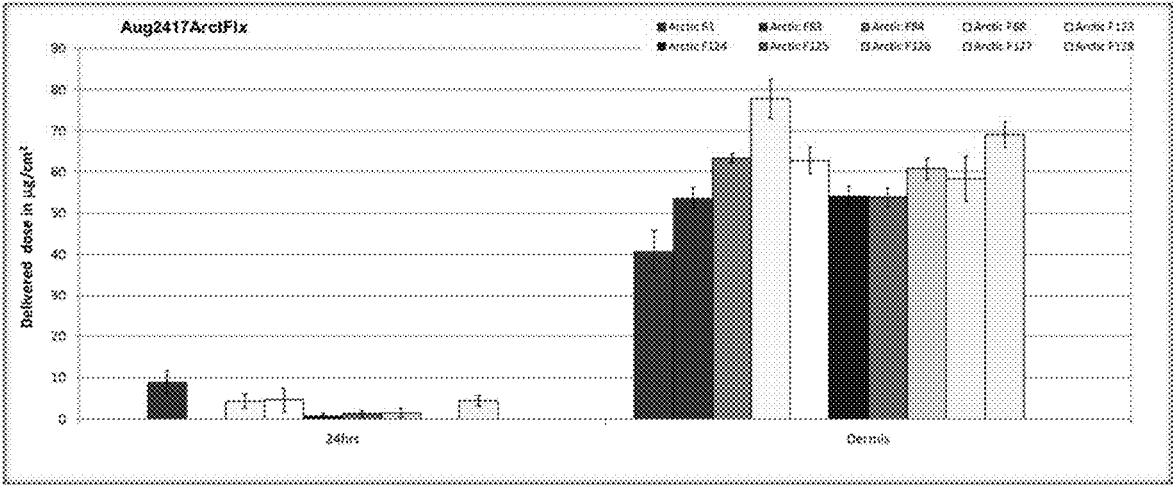
FIG. 15 shows bar graphs that represent data obtained from screening Donepezil base in an ethanol/propylene glycol/Transcutol chassis.
Figure 16:
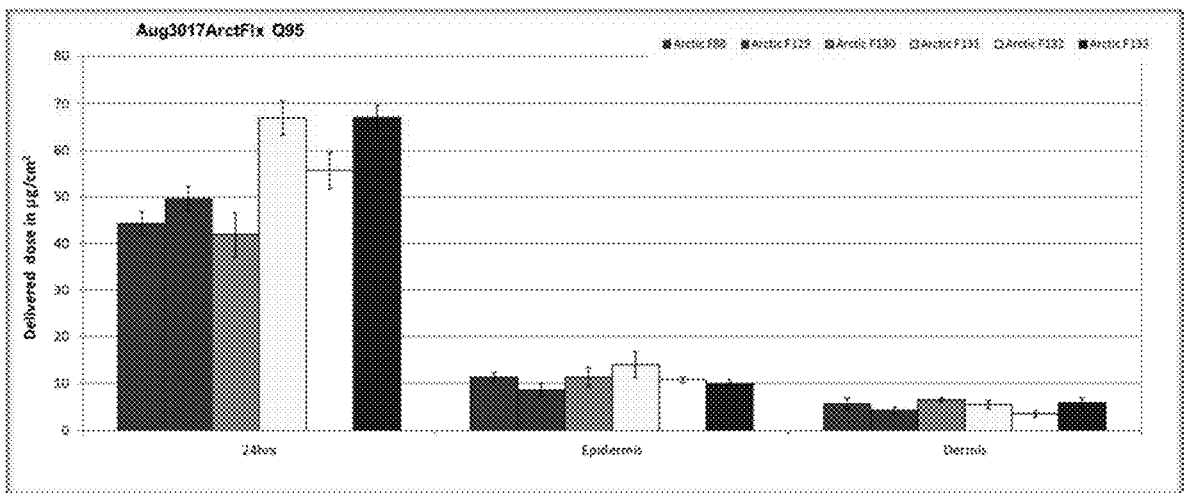
FIG. 16 shows bar graphs that represent data obtained from screening Donepezil base in an ethanol/propylene glycol/Transcutol chassis with isopropyl palmitate. The flux study was done using cadaver skin as the substrate.

Pure DMSO work best as an enhancer when used by itself (Arctic F3-FIG. 1).

Mixtures of DMSO with other solvents (FIGS. 3 & 4) did not significantly outperform non DMSO solvent mixtures (F20 vs. F14)

An ethanol/propylene glycol mixture (Arctic F20—with donepezil HCL, and later Arctic F34—with donepezil base) was chosen as a base control chassis to improve.

Donepezil base tended to cross the skin more readily than donepezil HCL (FIGS. 4-6) shown with F34 vs F20.

Based on additional rounds of screening in the Phase 1 studies (shown in FIGS. 7-15), a few more alterations were made to the base formulation:

The chassis was changed to an ethanol/propylene glycol/Transcutol mixture (based on F61 vs F34) Isopropyl palmitate was further added (based on F88 vs F61)

The lead formulation was identified as Arctic F88 for further optimization

Based on the results of studies using human skin cadaver and the Franz cell procedure (FIGS. 16-24), detailed herein, the following observations were made:

An ethanol/PEG/Transcutol/isopropyl palmitate formulation could deliver approximately 5× more donepezil into the skin (with retention in the dermis) than the control formulation. A lead F160 gel formulation was identified.

At 24 hrs, approximately 10× more of the Active remained in the epidermis or dermis rather than penetrating all the way through the skin for the F160 formulation.

A donepezil HCL cream was also formulated that delivered some ~3× more through into the skin than the Control.

TABLE 4

Data from studies of formulations in Table 2H:
Arct162A, 164A, 164B, and 164C

Delivered dose in μg/cm²

| Time (hrs) | Arct162 A | Arct164 A | Arct164 B | Arct164 C |
|---|---|---|---|---|
| 24 hrs | 3.96 | 2.06 | 2.11 | 2.57 |
| Epidermis | 15.35 | 19.24 | 11.53 | 18.13 |
| Dermis | 3.19 | 2.20 | 5.22 | 3.07 |

| Time (hrs) | StdErr | StdErr | StdErr | StdErr |
|---|---|---|---|---|
| 24 hrs | 0.75 | 0.19 | 0.17 | 0.36 |
| Epidermis | 2.17 | 0.80 | 2.57 | 1.41 |
| Dermis | 0.40 | 0.51 | 1.60 | 0.68 |

Percent delivered

| Time (hrs) | Arct162 A | Arct164 A | Arct164 B | Arct164 C |
|---|---|---|---|---|
| 24 hrs | 2.18 | 1.13 | 1.16 | 1.41 |
| Epidermis | 8.44 | 10.58 | 6.34 | 9.97 |
| Dermis | 1.76 | 1.21 | 2.87 | 1.69 |
| Time (hrs) | StdErr | StdErr | StdErr | StdErr |
| 24 hrs | 0.41 | 0.11 | 0.09 | 0.20 |
| Epidermis | 1.19 | 0.44 | 1.41 | 0.78 |
| Dermis | 0.22 | 0.28 | 0.88 | 0.38 |

Flux in $\mu g/cm^2/hr$

| Time (hrs) | Arct162 A | Arct164 A | Arct164 B | Arct164 C |
|---|---|---|---|---|
| 0-24 hrs | 0.16 | 0.09 | 0.09 | 0.11 |
| Time (hrs) | StdErr | StdErr | StdErr | StdErr |
| 0-24 hrs | 0.03 | 0.01 | 0.01 | 0.01 |

Example 5: Plaque Psoriasis Treatment of Psoriasis with Preferred Gel and Cream Formulations The Current Formulations are Tested Against Control Formulation:
Control
  HPMC (hydroxypropyl methyl cellulose) 3%
  PVP-40 (polyvinylpyrrolidone) 1%
  Donepezil HCl 0.1 or 1.0%
  H2O balance
Patients for the treatment of psoriasis are chosen from diagnosis of plaque type psoriasis vulgaris with silvery scales covering the surface of the lesion. None of these patients had arthritis.

Psoriasis is a hyper proliferative disease with altered differentiation of the keratinocytes. The keratinocytes in psoriatic skin lesions have an increase in the rate of maturation and it takes 3 to 4 days for a psoriatic basal cell to reach the horny layer, compared with the normal 3-4 weeks.

Topical treatment, which can vary from two weeks to one month, can improve both scaling, size, thickness and erythematous appearance of the lesions. The lesions in these patients are all symmetric and each patient can be treated with the formulation of the present invention on one side and with the control on the other.

The treatment consists of topically applying either the gel formulations F160 or F161, or the cream formulations F162, F165, F164A, F164B, or F164C. The gel formulation F160, and the cream formulation F162 and F165 are preferred.

Example 6

Wrinkles
Similar trials to Example 5a are carried out to treat wrinkles. Subjects between fifty and sixty years of age can be treated once a day three times a week for eight weeks. Then patients can be observed for improvement in skin texture and reduction of fine lines and this view was shared by their dermatologist.

Example 7: Wound Healing

Similar trials to Example 5a are carried out for wound healing. Patients who had chronic ulcers or wounds that did not heal became considerably can be treated for up to four weeks.

The treatment consists of topically applying either the gel formulations F160 or F161, or the cream formulations F162, F165, F164A, F164B, or F164C. The gel formulation F160, and the cream formulation F162 and F165 are preferred.

Example 8: Itching

Similar trials to Example 5a are carried out in a group of people with severe sunburn to determine effectiveness in controlling pain, erythema and itching.

The treatment consists of topically applying either the gel formulations F160 or F161, or the cream formulations F162, F165, F164A, F164B, or F164C. The gel formulation F160, and the cream formulation F162 and F165 are preferred.

Example 9: Edema

Similar trials to Example 5a are carried out in subjects with edema produced by trauma. The topical treatment is expected to lessen the edema produced by trauma, especially in the acute phase of the inflammation.

The treatment consists of topically applying either the gel formulations F160 or F161, or the cream formulations F162, F165, F164A, F164B, or F164C. The gel formulation F160, and the cream formulation F162 and F165 are preferred.

Example 10: Treatment of Acne

As shown in FIG. 25, panel A) (FIG. 25A) there is marked improvement observed in the pustulopapular acne distribution and size in this 26 year old male with grade 3 acne on his left shoulder and back resistant to other therapies, including accutane (top panels before therapy with F162 and bottom panels following 10 day therapy with F162. Panels B) and C) demonstrate similar improvement in facial pustulopapular acne in a 26 and 28 year old females, respectively, both with grade 3 acne resistant to other therapies, including Accutane (FIG. 25A and FIG. 25B). Both women had improved to grade 1 acne following ten days of therapy with F162, also with significant improvement in scars developed from previous acne.

F-162 cream formulation was locally applied over the acne area 2x daily for 10 days for each of the 3 patients.

Example 11: Atopic Dermatitis in Dogs

Safety and Efficacy of a Donepezil HCl in Client-Owned Dogs with Atopic Dermatitis
Study Goal:
  To evaluate the efficacy and safety of a piperidine-based, reversible inhibitor of acetylcholinesterase for the treatment of dogs with atopic dermatitis.
Study Criteria:
Inclusion Criteria.
  Client-owned dogs with short hair coat.
  12 months of age or older.
  3-80 kg
  Non-seasonal environmental-induced atopic dermatitis.
    Dogs with partial food-induced atopic dermatitis can be enrolled if other inclusion criteria are met.
  Any level of itching (i.e. chewing, scratching, licking, rubbing or rolling).
  Dogs must have been withdrawn from any medications for the treatment of dermatitis (listed below) with the exception of medicated shampoos and ear cleaners not containing glucocorticoids that have been used for at least 8 weeks prior to enrollment and maintained unchanged during the study.

Oral glucocorticoids—2 weeks

Injectable glucocorticoids—6 weeks

Oral cyclosporine—2 weeks

Oclacitinib—2 weeks

IL—31 monoclonal antibody-2 weeks

Oral antihistamines—1 week

Essential fatty acids—1 week

Topical glucocorticoids—1 week

Dogs with concurrent conditions would be allowed as long as treatment did not differ in the 6 weeks previous to enrollment and until the end of the study period.

Dogs should be on the same diet for at least 8 weeks prior to the study and remain on this diet throughout the study.

Exclusion Criteria.

Malignant neoplasia, demodicosis, flea bite allergy, conditions that could have affected immune function (e.g. hypothyroidism, hyperadrenocorticism, rickettsial disease, idiopathic thrombocytopenia, Von Willebrand's disease).

Dogs receiving, systemic antimicrobial therapy for bacterial folliculitis or fungal dermatitis, and lactating bitches or dogs (male or female) intended for use as breeding animals.

Dogs with clinically relevant abnormalities in their pretreatment complete blood count, serum chemistry or urinalysis tests were withdrawn from the study.

Withdrawal Criteria

Owner can choose to withdraw their pet from the study at any time.

Lack of owner compliance with treatment administration and evaluation visits.

Significant worsening of clinical signs that require intervention.

Side effects presumed to be related with treatment or that require medication not allowed during the study period.

Study

A 1% piperidine-based, reversible inhibitor of acetylcholinesterase (donepezil HCL) provided in the form of spray and gel.

Study Protocol:

Dogs will be sprayed twice daily with 1% donepezil HCl in water for 14 days. At the study visits, the gel will be applied after the spray. At home, owners may choose to apply the gel after the spray. The dogs will wear an Elizabethan collar (E-collar) for 20-30 minutes after application to prevent the animals from licking. Owners can watch the dogs closely or take them for walks during the 20-30 minutes as an alternative to the E-collar.

Study Visits:

Day 0; enrollment, physical examination, assessments of pruritus and dermatitis, blood and urine collection. A plasma sample will be banked for pharmacokinetics (PK). Study staff will dispense spray and gel. Spray will be mandatory, gel optional.

Day 7: Recheck appointment to complete assessments, blood draw for plasma for PK. Owners will be asked to defer application of spray and gel until the appointment. Study staff will apply spray and gel at the visit. Owners will bring their study spray and gel for accountability and receive more if necessary.

Day 14: Final appointment to complete assessments, blood and urine collection. A plasma sample will be banked for pharmacokinetics (PK). Owners will be asked to defer application of spray and gel until the appointment. Study staff will apply spray and gel at the visit. Owners will return all study spray and gel at this visit.

Study Assessments:

Baseline data (demographic, physical examination, assessments of pruritus and dermatitis) will be collected on enrollment at day 0. CBC, serum chemistry, urinalysis will be collected at days 0 and 14.

Owner Assessments:

1. Pruritus visual analog scale (PVAS)

A PVAS, consisting of a 10 cm line with word descriptors at 2 cm intervals, will be used by dog owners to assess the severity of the 'itch'. Owners will be instructed to place a mark on the PVAS line at the location that best represents the dog's pruritus (itching). At completion, the distance (in centimeters) from the bottom of the line ('normal dog') to the owner's mark on the line will be measured and recorded. Owners will perform a PVAS assessment on days 0, 7, 14.

2. Owner-reported global assessment of treatment efficacy (OGATE)

Owners will be asked on day 28 (study end): How would you rate the overall response to treatment?

0—No response

1—Poor response

2—Fair response

3—Good response

4—Excellent response

Veterinarian Assessments:

CADESI-04 scores will be used by the clinicians to assess dermatitis on days 0, 7 and 14.

Sample Size:

15 dogs

Outcome Measures:

CADESI-04

The percentage of dogs with veterinary-assessed skin lesion scores in the range of normal (i.e. CADESI 0 to 9) dogs or those with mild AD (i.e. CADESI 10 to 35) at the study end will be recorded for the standard of current therapy and our treatment groups.

PVAS

The percentage of dogs with owner assessed pruritus scores in the range of normal (0.0 to 1.9) dogs or those with mild AD (i.e. PVAS 2.0 to 3.5) at the study end.

OGATE

The percentage of dogs whose owner rated the overall response to treatment as "good" or "excellent" (i.e. scores 3 or 4, respectively).

Example 12: Analysis of Jan0919ArctFlx

Jan0919ArctFlx was analyzed for following parameters using QTest (95%):

Donepezil Transdermal

Donepezil Skin Retention

Donepezil Percent Delivery

Donepezil Flux

Time Elapsed 24 hrs

TABLE 5A

| General Information of Jan0919ArctFlx | |
| --- | --- |
| ID#: | Jan0919ArctFlx |
| Active: | Donepezil |
| Cell type: | 3 ml |
| Skin type: | Cadaver |

TABLE 5A-continued

| General Information of Jan0919ArctFlx | |
|---|---|
| Receptor fluid: | PBS + 0.01 wt % NaN3 |
| # of Timepoints: | 6 |
| # of Formulations: | 4 |
| # of Replicates: | 6 |
| Receptor volume (ml): | 3.30 |
| Surface area (cm$^2$): | 0.55 |

TABLE 5B

| Timepoints | |
|---|---|
| 1st timepoimt (hr): | 2.0 |
| 2nd timepoint (hr): | 4.0 |

TABLE 5B-continued

| Timepoints | |
|---|---|
| 3rd timepoint (hr): | 8.0 |
| 4th timepoint (hr): | 24.0 |
| 5th timepoint (hr): | Epidermis |
| 6th timepoint (hr): | Dermis |
| 7th timepoint (hr): | |
| 8th timepoint (hr): | |
| 9th timepoint (hr): | |
| 10th timepoint (hr): | |
| 11th timepoint (hr): | |
| 12th timepoint (hr): | |

TABLE 5C

| Skin Integrity Testing | | | | |
|---|---|---|---|---|
| Skin integrity testing | HPMC Gel (Control) | Arctic F183 | Arctic F186 | Arctic F187 |
| replicate 1 (kOhm) | 21.2 | 20.7 | 20.6 | 20.1 |
| replicate 2 (kOhm) | 18.5 | 19.1 | 19.6 | 20.1 |
| replicate 3 (kOhm) | 18.3 | 17.7 | 16.2 | 15.9 |
| replicate 4 (kOhm) | 12.6 | 12.9 | 13.9 | 14.2 |
| replicate 5 (kOhm) | 12.4 | 12.1 | 11.7 | 11.7 |
| replicate 6 (kOhm) | 5.4 | 6.8 | 6.9 | 10.1 |
| replicate 7 (kOhm) | | | | |
| replicate 8 (kOhm) | | | | |
| Values below in ug/ml | | | | |
| 1st timepoint (hr) | 2 | 2 | 2 | 2 |
| replicate 1 | 0.040 | 0.042 | 0.168 | 0.065 |
| replicate 2 | 0.142 | 0.041 | 0.053 | 0.077 |
| replicate 3 | 0.076 | 0.084 | 0.137 | 0.066 |
| replicate 4 | 0.076 | 0.051 | 0.075 | 0.084 |
| replicate 5 | 0.665 | 0.154 | 0.055 | 0.057 |
| replicate 6 | 0.051 | 0.025 | 0.069 | 0.027 |
| replicate 7 | | | | |
| replicate 8 | | | | |
| 2nd timepoint (hr) | 4 | 4 | 4 | 4 |
| replicate 1 | 0.039 | 0.090 | 3.587 | 0.038 |
| replicate 2 | 0.321 | 0.044 | 0.062 | 0.204 |
| replicate 3 | 0.180 | 0.089 | 0.087 | 0.081 |
| replicate 4 | 0.333 | 0.154 | 0.054 | 0.000 |
| replicate 5 | 1.250 | 0.338 | 0.057 | 0.142 |
| replicate 6 | 0.076 | 0.112 | 0.137 | 0.047 |
| replicate 7 | | | | |
| replicate 8 | | | | |
| 3rd timepoint (hr) | 8 | 8 | 8 | 8 |
| replicate 1 | 0.049 | 0.070 | 4.657 | 0.074 |
| replicate 2 | 0.584 | 0.024 | 0.109 | 0.253 |
| replicate 3 | 0.288 | 0.228 | 0.200 | 0.189 |
| replicate 4 | 0.748 | 0.390 | 0.058 | 0.071 |
| replicate 5 | 1.588 | 0.559 | 0.033 | 0.229 |
| replicate 6 | 0.078 | 0.353 | 0.262 | 0.097 |
| replicate 7 | | | | |
| replicate 8 | | | | |
| 4th timepoint (hr) | 24 | 24 | 24 | 24 |
| replicate 1 | 0.268 | 0.611 | 5.125 | 0.624 |
| replicate 2 | 0.852 | 0.642 | 0.095 | 0.293 |
| replicate 3 | 0.318 | 1.185 | 0.938 | 0.522 |
| replicate 4 | 1.291 | 2.111 | 0.803 | 0.720 |
| replicate 5 | 2.300 | 1.874 | 0.400 | 0.587 |
| replicate 6 | 0.286 | 1.404 | 1.486 | 0.803 |
| replicate 7 | | | | |
| replicate 8 | | | | |

TABLE 5C-continued

| Skin Integrity Testing | | | | |
|---|---|---|---|---|
| Epidermis | Epidermis | Epidermis | Epidermis | Epidermis |
| replicate 1 | 0.337 | 2.427 | 0.481 | 1.664 |
| replicate 2 | 0.466 | 4.126 | 1.532 | 0.977 |
| replicate 3 | 0.050 | 2.517 | 3.301 | 2.247 |
| replicate 4 | 1.015 | 2.967 | 2.976 | 2.438 |
| replicate 5 | 0.878 | 2.884 | 0.045 | 2.017 |
| replicate 6 | 0.464 | 2.722 | 3.790 | 2.098 |
| replicate 7 | | | | |
| replicate 8 | | | | |
| Dermis | Dermis | Dermis | Dermis | Dermis |
| replicate 1 | 0.157 | 0.200 | 0.249 | 0.142 |
| replicate 2 | 0.244 | 0.134 | 0.588 | 0.747 |
| replicate 3 | 0.098 | 0.182 | 0.352 | 0.214 |
| replicate 4 | 0.651 | 0.586 | 0.245 | 0.268 |
| replicate 5 | 0.394 | 0.331 | 0.822 | 0.433 |
| replicate 6 | 0.129 | 0.523 | 1.176 | 0.289 |
| replicate 7 | | | | |
| replicate 8 | | | | |

TABLE 5D

| Calculations ($\mu g/cm^2$). | | | | |
|---|---|---|---|---|
| 1st timepoint (hr) | 2 | 2 | 2 | 2 |
| replicate 1 | 0.242 | 0.251 | 1.010 | 0.393 |
| replicate 2 | 0.853 | 0.246 | 0.316 | 0.462 |
| replicate 3 | 0.455 | 0.501 | 0.822 | 0.396 |
| replicate 4 | 0.455 | 0.307 | 0.448 | 0.505 |
| replicate 5 | 3.989 | 0.927 | 0.328 | 0.343 |
| replicate 6 | 0.303 | 0.153 | 0.416 | 0.162 |
| replicate 7 | | | | |
| replicate 8 | | | | |
| 2nd timepoint (hr) | 4 | 4 | 4 | 4 |
| replicate 1 | 0.255 | 0.563 | 21.616 | 0.265 |
| replicate 2 | 2.005 | 0.289 | 0.399 | 1.267 |
| replicate 3 | 1.119 | 0.580 | 0.595 | 0.520 |
| replicate 4 | 2.039 | 0.955 | 0.367 | 0.046 |
| replicate 5 | 7.863 | 2.115 | 0.369 | 0.884 |
| replicate 6 | 0.484 | 0.683 | 0.858 | 0.295 |
| replicate 7 | | | | |
| replicate 8 | | | | |
| 3rd timepoint (hr) | 8 | 8 | 8 | 8 |
| replicate 1 | 0.339 | 0.492 | 29.988 | 0.501 |
| replicate 2 | 3.759 | 0.192 | 0.719 | 1.673 |
| replicate 3 | 1.867 | 1.463 | 1.322 | 1.214 |
| replicate 4 | 4.713 | 2.451 | 0.416 | 0.473 |
| replicate 5 | 10.570 | 3.623 | 0.256 | 1.484 |
| replicate 6 | 0.535 | 2.193 | 1.685 | 0.622 |
| replicate 7 | | | | |
| replicate 8 | | | | |
| 4th timepoint (hr) | 24 | 24 | 24 | 24 |
| replicate 1 | 1.678 | 3.774 | 35.339 | 3.840 |
| replicate 2 | 5.681 | 3.914 | 0.694 | 2.049 |
| replicate 3 | 2.205 | 7.326 | 5.861 | 3.313 |
| replicate 4 | 8.377 | 12.989 | 4.922 | 4.403 |
| replicate 5 | 15.708 | 11.816 | 2.481 | 3.753 |
| replicate 6 | 1.830 | 8.690 | 9.174 | 4.911 |
| replicate 7 | | | | |
| replicate 8 | | | | |
| Epidermis | Epidermis | Epidermis | Epidermis | Epidermis |
| replicate 1 | 1.836 | 13.237 | 2.621 | 9.079 |
| replicate 2 | 2.543 | 22.504 | 8.356 | 5.331 |
| replicate 3 | 0.271 | 13.729 | 18.003 | 12.256 |

TABLE 5D-continued

| Calculations ($\mu g/cm^2$). | | | | |
|---|---|---|---|---|
| replicate 4 | 5.537 | 16.184 | 16.235 | 13.298 |
| replicate 5 | 4.788 | 15.730 | 0.244 | 11.000 |
| replicate 6 | 2.530 | 14.847 | 20.672 | 11.443 |
| replicate 7 | | | | |
| replicate 8 | | | | |
| Dermis | Dermis | Dermis | Dermis | Dermis |
| replicate 1 | 0.856 | 1.089 | 1.361 | 0.773 |
| replicate 2 | 1.328 | 0.729 | 3.205 | 4.076 |
| replicate 3 | 0.537 | 0.993 | 1.920 | 1.168 |
| replicate 4 | 3.553 | 3.194 | 1.335 | 1.462 |
| replicate 5 | 2.149 | 1.804 | 4.482 | 2.360 |
| replicate 6 | 0.703 | 2.851 | 6.417 | 1.578 |
| replicate 7 | | | | |
| replicate 8 | | | | |

TABLE 5E

| Delivery Dose in $\mu g/cm^2$. | | | | |
|---|---|---|---|---|
| Time (hrs) | HPMC Gel (Control) | Arctic F183 | Arctic F186 | Arctic F187 |
| 2 hrs | 1.05 | 0.40 | 0.56 | 0.38 |
| 4 hrs | 2.29 | 0.86 | 4.03 | 0.55 |
| 8 hrs | 3.63 | 1.74 | 5.73 | 0.99 |
| 24 hrs | 5.91 | 8.08 | 9.74 | 3.71 |
| Epidermis | 2.92 | 16.04 | 11.02 | 10.40 |
| Dermis | 1.52 | 1.78 | 3.12 | 1.90 |
| Time (hrs) | StdErr | StdErr | StdErr | StdErr |
| 2 hrs | 0.59 | 0.12 | 0.12 | 0.05 |
| 4 hrs | 1.15 | 0.26 | 3.52 | 0.19 |
| 8 hrs | 1.56 | 0.53 | 4.86 | 0.22 |
| 24 hrs | 2.24 | 1.58 | 5.25 | 0.40 |
| Epidermis | 0.79 | 1.37 | 3.48 | 1.17 |
| Dermis | 0.47 | 0.42 | 0.83 | 0.48 |

TABLE 5F

| | Flux in µg/cm²/hr. | | | |
|---|---|---|---|---|
| Time (hrs) | HPMC Gel (Control) | Arctic F183 | Arctic F186 | Arctic F187 |
| 0-2 hrs | 0.52 | 0.20 | 0.28 | 0.19 |
| 2-4 hrs | 0.62 | 0.23 | 1.74 | 0.08 |
| 4-8 hrs | 0.33 | 0.22 | 0.42 | 0.11 |
| 8-24 hrs | 0.14 | 0.40 | 0.25 | 0.17 |
| Time (hrs) | StdErr | StdErr | StdErr | StdErr |
| 0-2 hrs | 0.30 | 0.06 | 0.06 | 0.02 |
| 2-4 hrs | 0.29 | 0.09 | 1.71 | 0.09 |
| 4-8 hrs | 0.12 | 0.08 | 0.34 | 0.02 |
| 8-24 hrs | 0.05 | 0.07 | 0.07 | 0.04 |

TABLE 6A

Ttest Results for 2 hr (Two-tailed with unequal variance)-
Values shown are probability values.

| Formulations | HPMC Gel (Control) | Arctic F183 | Arctic F186 | Arctic F187 |
|---|---|---|---|---|
| HPMC Gel (Control) | 1.00 | | | |
| Arctic F183 | 0.33 | 1.00 | | |
| Arctic F186 | 0.45 | 0.36 | 1.00 | |
| Arctic F187 | 0.31 | 0.87 | 0.20 | 1.00 |

TABLE 6B

Ttest Results for 4 hr (Two-tailed with unequal variance)-
Values shown are probability values.

| Formulations | HPMC Gel (Control) | Arctic F183 | Arctic F186 | Arctic F187 |
|---|---|---|---|---|
| HPMC Gel (Control) | 1.00 | | | |
| Arctic F183 | 0.28 | 1.00 | | |
| Arctic F186 | 0.65 | 0.41 | 1.00 | |
| Arctic F187 | 0.19 | 0.35 | 0.37 | 1.00 |

TABLE 6C

Ttest Results for 8 hr (Two-tailed with unequal variance)-
Values shown are probability values.

| Formulations | HPMC Gel (Control) | Arctic F183 | Arctic F186 | Arctic F187 |
|---|---|---|---|---|
| HPMC Gel (Control) | 1.00 | | | |
| Arctic F183 | 0.29 | 1.00 | | |
| Arctic F186 | 0.69 | 0.45 | 1.00 | |
| Arctic F187 | 0.15 | 0.24 | 0.37 | 1.00 |

TABLE 6D

Ttest Results for 24 hr (Two-tailed with unequal variance)-
Values shown are probability values.

| Formulations | HPMC Gel (Control) | Arctic F183 | Arctic F186 | Arctic F187 |
|---|---|---|---|---|
| HPMC Gel (Control) | 1.00 | | | |
| Arctic F183 | 0.45 | 1.00 | | |

TABLE 6D-continued

Ttest Results for 24 hr (Two-tailed with unequal variance)-
Values shown are probability values.

| Formulations | HPMC Gel (Control) | Arctic F183 | Arctic F186 | Arctic F187 |
|---|---|---|---|---|
| Arctic F186 | 0.52 | 0.77 | 1.00 | |
| Arctic F187 | 0.38 | 0.04 | 0.30 | 1.00 |

TABLE 6E

Ttest Results for Epidermis (Two-tailed with unequal variance)-
Values shown are probability values.

| Formulations | HPMC Gel (Control) | Arctic F183 | Arctic F186 | Arctic F187 |
|---|---|---|---|---|
| HPMC Gel (Control) | 1.00 | | | |
| Arctic F183 | 0.00 | 1.00 | | |
| Arctic F186 | 0.07 | 0.22 | 1.00 | |
| Arctic F187 | 0.00 | 0.01 | 0.87 | 1.00 |

TABLE 6F

Ttest Results for Dermis (Two-tailed with unequal variance)-
Values shown are probability values.

| Formulations | HPMC Gel (Control) | Arctic F183 | Arctic F186 | Arctic F187 |
|---|---|---|---|---|
| HPMC Gel (Control) | 1.00 | | | |
| Arctic F183 | 0.69 | 1.00 | | |
| Arctic F186 | 0.13 | 0.19 | 1.00 | |
| Arctic F187 | 0.58 | 0.85 | 0.24 | 1.00 |

Example 13: Analysis of Jan0919ArctFlx Q95

Jan0919ArctFlx was analyzed for following parameters using QTest (95%):
Donepezil Transdermal
Donepezil Skin Retention
Donepezil Percent Delivery
Donepezil Flux
Time Elapsed 24 hrs

TABLE 7A

| General Information of Jan0919ArctFlx Q95. | |
|---|---|
| ID#: | Jan0919ArctFlx Q95 |
| Active: | Donepezil |
| Cell type: | 3 ml |
| Skin type: | Cadaver |
| Receptor fluid: | PBS + 0.01 wt % NaN3 |
| # of Timepoints: | 6 |
| # of Formulations: | 4 |
| # of Replicates: | 6 |
| Receptor volume (ml): | 3.30 |
| Surface area (cm²): | 0.55 |

TABLE 7B

| Timepoints. | |
|---|---|
| 1st timepoimt (hr): | 2.0 |
| 2nd timepoint (hr): | 4.0 |
| 3rd timepoint (hr): | 8.0 |
| 4th timepoint (hr): | 24.0 |
| 5th timepoint (hr): | Epidermis |

TABLE 7B-continued

| Timepoints. | |
| --- | --- |
| 6th timepoint (hr): | Dermis |
| 7th timepoint (hr): | |
| 8th timepoint (hr): | |
| 9th timepoint (hr): | |
| 10th timepoint (hr): | |
| 11th timepoint (hr): | |
| 12th timepoint (hr): | |

TABLE 7C

| | Skin Integrity Testing. | | | |
| --- | --- | --- | --- | --- |
| Skin integrity testing | HPMC Gel (Control) | Arctic F183 | Arctic F186 | Arctic F187 |
| replicate 1 (kOhm) | 21.2 | 20.7 | 20.6 | 20.1 |
| replicate 2 (kOhm) | 18.5 | 19.1 | 19.6 | 20.1 |
| replicate 3 (kOhm) | 18.3 | 17.7 | 16.2 | 15.9 |
| replicate 4 (kOhm) | 12.6 | 12.9 | 13.9 | 14.2 |
| replicate 5 (kOhm) | 12.4 | 12.1 | 11.7 | 11.7 |
| replicate 6 (kOhm) | 5.4 | 6.8 | 6.9 | 10.1 |
| replicate 7 (kOhm) | | | | |
| replicate 8 (kOhm) | | | | |

Values below in ug/ml

| 1st timepoint (hr) | 2 | 2 | 2 | 2 |
| --- | --- | --- | --- | --- |
| replicate 1 | 0.040 | 0.042 | | 0.065 |
| replicate 2 | 0.142 | 0.041 | 0.053 | 0.077 |
| replicate 3 | 0.076 | 0.084 | 0.137 | 0.066 |
| replicate 4 | 0.076 | 0.051 | 0.075 | 0.084 |
| replicate 5 | | 0.154 | 0.055 | 0.057 |
| replicate 6 | 0.051 | 0.025 | 0.069 | 0.027 |
| replicate 7 | | | | |
| replicate 8 | | | | |

| 2nd timepoint (hr) | 4 | 4 | 4 | 4 |
| --- | --- | --- | --- | --- |
| replicate 1 | 0.039 | 0.090 | | 0.038 |
| replicate 2 | 0.321 | 0.044 | 0.062 | 0.204 |
| replicate 3 | 0.180 | 0.089 | 0.087 | 0.081 |
| replicate 4 | 0.333 | 0.154 | 0.054 | 0.000 |
| replicate 5 | | | 0.057 | 0.142 |
| replicate 6 | 0.076 | 0.112 | 0.137 | 0.047 |
| replicate 7 | | | | |
| replicate 8 | | | | |

| 3rd timepoint (hr) | 8 | 8 | 8 | 8 |
| --- | --- | --- | --- | --- |
| replicate 1 | 0.049 | 0.070 | | 0.074 |
| replicate 2 | 0.584 | 0.024 | 0.109 | 0.253 |
| replicate 3 | 0.288 | 0.228 | 0.200 | 0.189 |
| replicate 4 | 0.748 | 0.390 | 0.058 | 0.071 |
| replicate 5 | | 0.559 | 0.033 | 0.229 |
| replicate 6 | 0.078 | 0.353 | 0.262 | 0.097 |
| replicate 7 | | | | |
| replicate 8 | | | | |

| 4th timepoint (hr) | 24 | 24 | 24 | 24 |
| --- | --- | --- | --- | --- |
| replicate 1 | 0.268 | 0.611 | | 0.624 |
| replicate 2 | 0.852 | 0.642 | 0.095 | 0.293 |
| replicate 3 | 0.318 | 1.185 | 0.938 | 0.522 |
| replicate 4 | 1.291 | 2.111 | 0.803 | 0.720 |
| replicate 5 | | 1.874 | 0.400 | 0.587 |
| replicate 6 | 0.286 | 1.404 | 1.486 | 0.803 |
| replicate 7 | | | | |
| replicate 8 | | | | |

| Epidermis | Epidermis | Epidermis | Epidermis | Epidermis |
| --- | --- | --- | --- | --- |
| replicate 1 | 0.337 | 2.427 | 0.481 | 1.664 |
| replicate 2 | 0.466 | | 1.532 | 0.977 |
| replicate 3 | 0.050 | 2.517 | 3.301 | 2.247 |

TABLE 7C-continued

| | Skin Integrity Testing. | | | |
| --- | --- | --- | --- | --- |
| replicate 4 | 1.015 | 2.967 | 2.976 | 2.438 |
| replicate 5 | 0.878 | 2.884 | 0.045 | 2.017 |
| replicate 6 | 0.464 | 2.722 | 3.790 | 2.098 |
| replicate 7 | | | | |
| replicate 8 | | | | |

| Dermis | Dermis | Dermis | Dermis | Dermis |
| --- | --- | --- | --- | --- |
| replicate 1 | 0.157 | 0.200 | 0.249 | 0.142 |
| replicate 2 | 0.244 | 0.134 | 0.588 | 0.747 |
| replicate 3 | 0.098 | 0.182 | 0.352 | 0.214 |
| replicate 4 | 0.651 | 0.586 | 0.245 | 0.268 |
| replicate 5 | 0.394 | 0.331 | 0.822 | 0.433 |
| replicate 6 | 0.129 | 0.523 | 1.176 | 0.289 |
| replicate 7 | | | | |
| replicate 8 | | | | |

TABLE 7D

| | Calculations (μg/cm$^2$). | | | |
| --- | --- | --- | --- | --- |
| 1st timepoint (hr) | 2 | 2 | 2 | 2 |
| replicate 1 | 0.242 | 0.251 | | 0.393 |
| replicate 2 | 0.853 | 0.246 | 0.316 | 0.462 |
| replicate 3 | 0.455 | 0.501 | 0.822 | 0.396 |
| replicate 4 | 0.455 | 0.307 | 0.448 | 0.505 |
| replicate 5 | | 0.927 | 0.328 | 0.343 |
| replicate 6 | 0.303 | 0.153 | 0.416 | 0.162 |
| replicate 7 | | | | |
| replicate 8 | | | | |

| 2nd timepoint (hr) | 4 | 4 | 4 | 4 |
| --- | --- | --- | --- | --- |
| replicate 1 | 0.255 | 0.563 | | 0.265 |
| replicate 2 | 2.005 | 0.289 | 0.399 | 1.267 |
| replicate 3 | 1.119 | 0.580 | 0.595 | 0.520 |
| replicate 4 | 2.039 | 0.955 | 0.367 | 0.046 |
| replicate 5 | | | 0.369 | 0.884 |
| replicate 6 | 0.484 | 0.683 | 0.858 | 0.295 |
| replicate 7 | | | | |
| replicate 8 | | | | |

| 3rd timepoint (hr) | 8 | 8 | 8 | 8 |
| --- | --- | --- | --- | --- |
| replicate 1 | 0.339 | 0.492 | | 0.501 |
| replicate 2 | 3.759 | 0.192 | 0.719 | 1.673 |
| replicate 3 | 1.867 | 1.463 | 1.322 | 1.214 |
| replicate 4 | 4.713 | 2.451 | 0.416 | 0.473 |
| replicate 5 | | 3.439 | 0.256 | 1.484 |
| replicate 6 | 0.535 | 2.193 | 1.685 | 0.622 |
| replicate 7 | | | | |
| replicate 8 | | | | |

| 4th timepoint (hr) | 24 | 24 | 24 | 24 |
| --- | --- | --- | --- | --- |
| replicate 1 | 1.678 | 3.774 | | 3.840 |
| replicate 2 | 5.681 | 3.914 | 0.694 | 2.049 |
| replicate 3 | 2.205 | 7.326 | 5.861 | 3.313 |
| replicate 4 | 8.377 | 12.989 | 4.922 | 4.403 |
| replicate 5 | | 11.631 | 2.481 | 3.753 |
| replicate 6 | 1.830 | 8.690 | 9.174 | 4.911 |
| replicate 7 | | | | |
| replicate 8 | | | | |

| Epidermis | Epidermis | Epidermis | Epidermis | Epidermis |
| --- | --- | --- | --- | --- |
| replicate 1 | 1.836 | 13.237 | 2.621 | 9.079 |
| replicate 2 | 2.543 | | 8.356 | 5.331 |
| replicate 3 | 0.271 | 13.729 | 18.003 | 12.256 |

TABLE 7D-continued

| Calculations ($\mu g/cm^2$). | | | | |
|---|---|---|---|---|
| replicate 4 | 5.537 | 16.184 | 16.235 | 13.298 |
| replicate 5 | 4.788 | 15.730 | 0.244 | 11.000 |
| replicate 6 | 2.530 | 14.847 | 20.672 | 11.443 |
| replicate 7 | | | | |
| replicate 8 | | | | |

| Dermis | Dermis | Dermis | Dermis | Dermis |
|---|---|---|---|---|
| replicate 1 | 0.856 | 1.089 | 1.361 | 0.773 |
| replicate 2 | 1.328 | 0.729 | 3.205 | 4.076 |
| replicate 3 | 0.537 | 0.993 | 1.920 | 1.168 |
| replicate 4 | 3.553 | 3.194 | 1.335 | 1.462 |
| replicate 5 | 2.149 | 1.804 | 4.482 | 2.360 |
| replicate 6 | 0.703 | 2.851 | 6.417 | 1.578 |
| replicate 7 | | | | |
| replicate 8 | | | | |

TABLE 7E

| Delivery Dose in $\mu g/cm^2$. | | | | |
|---|---|---|---|---|
| Time (hrs) | HPMC Gel (Control) | Arctic F183 | Arctic F186 | Arctic F187 |
| 2 hrs | 0.46 | 0.40 | 0.47 | 0.38 |
| 4 hrs | 1.18 | 0.61 | 0.52 | 0.55 |
| 8 hrs | 2.24 | 1.70 | 0.88 | 0.99 |
| 24 hrs | 3.95 | 8.05 | 4.63 | 3.71 |
| Epidermis | 2.92 | 14.75 | 11.02 | 10.40 |
| Dermis | 1.52 | 1.78 | 3.12 | 1.90 |

| Time (hrs) | StdErr | StdErr | StdErr | StdErr |
|---|---|---|---|---|
| 2 hrs | 0.11 | 0.12 | 0.09 | 0.05 |
| 4 hrs | 0.37 | 0.11 | 0.10 | 0.19 |
| 8 hrs | 0.87 | 0.50 | 0.27 | 0.22 |
| 24 hrs | 1.33 | 1.57 | 1.46 | 0.40 |
| Epidermis | 0.79 | 0.56 | 3.48 | 1.17 |
| Dermis | 0.47 | 0.42 | 0.83 | 0.48 |

TABLE 7F

| Flux in $\mu g/cm^2/hr$. | | | | |
|---|---|---|---|---|
| Time (hrs) | HPMC Gel (Control) | Arctic F183 | Arctic F186 | Arctic F187 |
| 0-2 hrs | 0.23 | 0.20 | 0.23 | 0.19 |
| 2-4 hrs | 0.36 | 0.11 | 0.03 | 0.08 |
| 4-8 hrs | 0.27 | 0.27 | 0.09 | 0.11 |
| 8-24 hrs | 0.11 | 0.40 | 0.23 | 0.17 |

| Time (hrs) | StdErr | StdErr | StdErr | StdErr |
|---|---|---|---|---|
| 0-2 hrs | 0.05 | 0.06 | 0.05 | 0.02 |
| 2-4 hrs | 0.15 | 0.06 | 0.06 | 0.09 |
| 4-8 hrs | 0.13 | 0.08 | 0.05 | 0.02 |
| 8-24 hrs | 0.03 | 0.07 | 0.08 | 0.04 |

TABLE 8A

| Ttest Results for 2 hr (Two-tailed with unequal variance)- Values shown are probability values. | | | | |
|---|---|---|---|---|
| Formulations | HPMC Gel (Control) | Arctic F183 | Arctic F186 | Arctic F187 |
| HPMC Gel (Control) | 1.00 | | | |
| Arctic F183 | 0.69 | 1.00 | | |
| Arctic F186 | 0.97 | 0.65 | 1.00 | |
| Arctic F187 | 0.50 | 0.87 | 0.43 | 1.00 |

TABLE 8B

| Ttest Results for 4 hr (Two-tailed with unequal variance)- Values shown are probability values. | | | | |
|---|---|---|---|---|
| Formulations | HPMC Gel (Control) | Arctic F183 | Arctic F186 | Arctic F187 |
| HPMC Gel (Control) | 1.00 | | | |
| Arctic F183 | 0.21 | 1.00 | | |
| Arctic F186 | 0.15 | 0.52 | 1.00 | |
| Arctic F187 | 0.18 | 0.76 | 0.90 | 1.00 |

TABLE 8C

| Ttest Results for 8 hr (Two-tailed with unequal variance)- Values shown are probability values. | | | | |
|---|---|---|---|---|
| Formulations | HPMC Gel (Control) | Arctic F183 | Arctic F186 | Arctic F187 |
| HPMC Gel (Control) | 1.00 | | | |
| Arctic F183 | 0.61 | 1.00 | | |
| Arctic F186 | 0.20 | 0.19 | 1.00 | |
| Arctic F187 | 0.23 | 0.24 | 0.75 | 1.00 |

TABLE 8D

| Ttest Results for 24 hr (Two-tailed with unequal variance)- Values shown are probability values. | | | | |
|---|---|---|---|---|
| Formulations | HPMC Gel (Control) | Arctic F183 | Arctic F186 | Arctic F187 |
| HPMC Gel (Control) | 1.00 | | | |
| Arctic F183 | 0.08 | 1.00 | | |
| Arctic F186 | 0.74 | 0.14 | 1.00 | |
| Arctic F187 | 0.87 | 0.04 | 0.57 | 1.00 |

TABLE 8E

| Ttest Results for Epidermis (Two-tailed with unequal variance)- Values shown are probability values. | | | | |
|---|---|---|---|---|
| Formulations | HPMC Gel (Control) | Arctic F183 | Arctic F186 | Arctic F187 |
| HPMC Gel (Control) | 1.00 | | | |
| Arctic F183 | 0.00 | 1.00 | | |
| Arctic F186 | 0.07 | 0.34 | 1.00 | |
| Arctic F187 | 0.00 | 0.01 | 0.87 | 1.00 |

TABLE 8F

| T-test Results for Dermis (Two-tailed with unequal variance)- Values shown are probability values. | | | | |
|---|---|---|---|---|
| Formulations | HPMC Gel (Control) | Arctic F183 | Arctic F186 | Arctic F187 |
| HPMC Gel (Control) | 1.00 | | | |
| Arctic F183 | 0.69 | 1.00 | | |
| Arctic F186 | 0.13 | 0.19 | 1.00 | |
| Arctic F187 | 0.58 | 0.85 | 0.24 | 1.00 |

Example 13: Safety and Efficacy of a
Piperidine-Based, Reversible Inhibitor of
Acetylcholinesterase in Client-Owned Dogs with
Atopic Dermatitis The study described in Example 13 is a principal-of-concept open label clinical trial where the primary goal was to evaluate the efficacy of a piperidine-based, reversible inhibitor of acetylcholinesterase in improving the clinical signs (i.e., skin inflammation and pruritus) associated with canine atopic dermatitis. Eleven client-owned dogs with atopic dermatitis were enrolled in the study. The investigator evaluated the severity and extent of skin lesions on days 0, 7, and 14 using a validated scoring system (Canine Atopic Dermatitis Extent and Severity Index-4 iteration; CADESI-4). At the same study visits, owners evaluated the dogs' pruritus level using a validated pruritus visual analog scale (PVAS). In addition, on day 14 (study end) the owners did a global assessment of treatment efficacy (OGATE) using a five-point scale (i.e., 0=no response; 1=poor response; 2=fair response; 3=good response; 4=excellent response).

The average CADESI-4 scores on days 0, 7 and 14 were 252, 119 and 139. The average PVAS scores on days 0, 7 and 14 were 71.6, 59.2 and 55.4. Paired Student's t-tests and 95% confidence intervals of average differences for the CADESI-4 and PVAS scores are shown in the Table 9. There was significant decrease in skin inflammation (CADESI: P<0.00048, PVAS: P<0.0108) and pruritus level (PVAS: P<0.009, PVAS: P<0.012) between days 0 and 14. Three dog owners assessed the clinical improvement of their dogs as excellent, five as good, one as fair, one as poor and one as no response.

TABLE 9

Paired Student's T-tests and 95% Confidence Intervals of Average Differences for the CADESI-4 and PVAS Scores (*P < 0.05 was considered significant)

| Comparisons | 95% Confidence Intervals | *P Value |
| --- | --- | --- |
| CADESI 0-7 | 6.78-17.40 | 0.00048 |
| CADESI 0-14 | 3.06-17.49 | 0.00996 |
| PVAS 0-7 | 0.32-1.93 | 0.01088 |
| PVAS 0-14 | 0.40-2.55 | 0.01225 |

Despite the fact that there was a significant reduction in the PVAS scores during the trial most owners commented that the itching (pruritus) level did not decrease.

There was no adverse reaction during the 14-day application of the ointment.

In summary, the study results indicate that the piperidine-based, reversible inhibitor of acetylcholinesterase tested in this open-label clinical trial can be beneficial to control the clinical signs associated with canine atopic dermatitis. A double-blinded, placebo controlled trial is also conducted to further corroborate these results.

The invention claimed is:

1. A composition prepared for topical administration comprising
  (i) donepezil or a pharmaceutically acceptable salt thereof,
  (ii) 2-(2-ethoxyethoxy) ethan-1-ol,
  (iii) a fatty acid ester, and
  (iv) cetyl alcohol,
  wherein the composition is formulated to deliver donepezil intradermally.

2. The composition of claim 1, wherein the composition is in a form of a cream.

3. The composition of claim 1, wherein the composition further comprises water.

4. The composition of claim 3, wherein water is present in an amount between about 10% (wt/wt) and about 65% (wt/wt).

5. The composition of claim 1, wherein the composition comprises 2-(2-ethoxyethoxy) ethan-1-ol in an amount between about 5% (wt/wt) and about 30% (wt/wt).

6. The composition of claim 1, wherein the fatty acid ester is in an amount between about 5% (wt/wt) and about 13% (wt/wt).

7. The composition of claim 1, wherein the fatty acid ester is selected from the group consisting of isopropyl palmitate, caprylic triglyceride, capric (C10) triglyceride, isopropyl myristate, and combinations thereof.

8. The composition of claim 1, wherein cetyl alcohol is in an amount between about 3% (wt/wt) and about 11% (wt/wt).

9. A composition prepared for topical administration comprising:
  (i) donepezil or donepezil HCl;
  (ii) 2-(2-ethoxyethoxy) ethan-1-ol in an amount between about 5% (wt/wt) to about 30% (wt/wt);
  (iii) a fatty acid ester selected from the group consisting of isopropyl palmitate, caprylic triglyceride, capric (C10) triglyceride, isopropyl myristate, and any combination thereof in an amount between about 5% (wt/wt) to about 13% (wt/wt); and
  (iv) cetyl alcohol in an amount between about 3% (wt/wt) to about 11% (wt/wt);
  wherein the composition is formulated to deliver donepezil intradermally and wherein the composition is in a form of a cream.

10. The composition of claim 1, further comprising ethylene glycol, propylene glycol, or a combination thereof.

11. The composition of claim 10, wherein the composition comprises propylene glycol.

12. The composition of claim 10, wherein propylene glycol is present in an amount of about 7% (wt/wt).

13. The composition of claim 2, wherein the composition comprises donepezil HCl, water, cetyl alcohol, 2-(2-ethoxyethoxy) ethan-1-ol, a mixture of caprylic and capric (C10) triglyceride, and isopropyl palmitate.

14. The composition of claim 2, wherein the composition comprises donepezil HCl, water, cetyl alcohol, 2-(2-ethoxyethoxy) ethan-1-ol, a mixture of caprylic and capric (C10) triglyceride, isopropyl myristate, isopropyl palmitate, and propylene glycol.

15. The composition of claim 13, wherein donepezil HCl is present in an amount of 1% (wt/wt), water is present in amount of about 40.3% (wt/wt), cetyl alcohol is present in an amount of about 10% (wt/wt), isopropyl myristate is present in an amount of about 10% (wt/wt), a mixture of caprylic and capric (C10) triglyceride is present in an amount of about 10% (wt/wt), and isopropyl palmitate is present in an amount of 7% (wt/wt).

16. The composition of claim 13, wherein donepezil HCl is present in an amount of 1% (wt/wt), water is present in an amount of about 56.9% (wt/wt), cetyl alcohol is present in an amount of about 3% (wt/wt), a mixture of caprylic and capric (C10) triglyceride is present in an amount of about 5% (wt/wt), and isopropyl palmitate is present in an amount of about 7% (wt/wt).

17. The composition of claim 13, wherein donepezil HCl is present in an amount of about 1% (wt/wt), water is present in an amount of about 48.9% (wt/wt), cetyl alcohol is present in an amount of about 11% (wt/wt), a mixture of caprylic and capric (C10) triglyceride is present in an amount of about 5% (wt/wt), and isopropyl palmitate is present in an amount of about 7% (wt/wt).

18. The composition of claim 17, wherein the composition further comprises sorbitan monolaurate, a polysorbate, an emollient or a combination thereof.

19. The composition of claim 18, wherein donepezil HCl is present in an amount of about 1% (wt/wt), 2-(2-ethoxy-ethoxy) ethan-1-ol is present in an amount of about 7% (wt/wt), propylene glycol is present in an amount of about 7% (wt/wt), cetyl alcohol is present in an amount of about 11% (wt/wt), a mixture of caprylic and capric (C10) triglyceride is present in an amount of about 5% (wt/wt), isopropyl palmitate is present in an amount of about 7% (wt/wt), bee wax is present in an amount of about 5% (wt/wt), sorbitan monolaurate is present in an amount of about 4.8% (wt/wt), polysorbate 20 is present in an amount of about 3.2% (wt/wt), and water is present in an amount of about 48.9% (wt/wt).

20. The composition of claim 2, wherein donepezil HCl is present in an amount of 1% (wt/wt), water is present in an amount of 51.9% (wt/wt), cetyl alcohol is present in an amount of 9% (wt/wt), a mixture of caprylic and capric (C10) triglyceride is present in an amount of 5% (wt/wt), and isopropyl palmitate is present in an amount of 7% (wt/wt).

\* \* \* \* \*